(12) United States Patent
Starczynowski et al.

(10) Patent No.: US 9,855,273 B2
(45) Date of Patent: *Jan. 2, 2018

(54) COMBINATION THERAPY FOR MDS

(71) Applicant: Children's Hospital Medical Center, Cincinnati, OH (US)

(72) Inventors: Daniel Starczynowski, Cincinnati, OH (US); Garrett W. Rhyasen, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,402

(22) Filed: Oct. 7, 2016

(65) Prior Publication Data

US 2017/0087162 A1     Mar. 30, 2017

Related U.S. Application Data

(63) Continuation of application No. 14/842,049, filed on Sep. 1, 2015, now Pat. No. 9,504,706, which is a continuation of application No. 14/284,521, filed on May 22, 2014, now Pat. No. 9,168,257.

(60) Provisional application No. 61/826,211, filed on May 22, 2013.

(51) Int. Cl.
| | |
|---|---|
| *C07H 21/02* | (2006.01) |
| *C07H 21/04* | (2006.01) |
| *A61K 48/00* | (2006.01) |
| *A61K 31/5377* | (2006.01) |
| *A61K 31/4184* | (2006.01) |
| *A61K 31/519* | (2006.01) |
| *A61K 31/4375* | (2006.01) |
| *A61K 45/06* | (2006.01) |
| *A61K 31/495* | (2006.01) |
| *A61K 31/496* | (2006.01) |
| *A61K 31/404* | (2006.01) |

(52) U.S. Cl.
CPC ........ *A61K 31/5377* (2013.01); *A61K 31/404* (2013.01); *A61K 31/4184* (2013.01); *A61K 31/4375* (2013.01); *A61K 31/495* (2013.01); *A61K 31/496* (2013.01); *A61K 31/519* (2013.01); *A61K 45/06* (2013.01)

(58) Field of Classification Search
CPC ... A61K 48/00; C12N 2310/11; C12N 15/113
See application file for complete search history.

(56) References Cited

U.S. PATENT DOCUMENTS

| | | | |
|---|---|---|---|
| 8,288,377 B2 * | 10/2012 | Storck ................. | C07D 413/14 514/230.5 |
| 9,168,257 B2 | 10/2015 | Starczynowski et al. | |
| 9,382,239 B2 | 7/2016 | Gray et al. | |
| 9,504,706 B2 | 11/2016 | Starczynowski et al. | |
| 2014/0309249 A1 * | 10/2014 | Gray ................... | A61K 31/437 514/275 |

FOREIGN PATENT DOCUMENTS

| | | |
|---|---|---|
| WO | WO 03/030902 | 4/2003 |
| WO | WO 2013/006443 | 1/2013 |
| WO | WO 2013/042137 | 3/2013 |

OTHER PUBLICATIONS

International Search Report and Written Opinion dated Nov. 20, 2014 for Application No. PCT/US2014/039156.
Bar, et al., "Gene expression patterns in myelodyplasia underline the role of apoptosis and differentiation in disease initiation and progression", Translational Oncogenomics, 3, pp. 137-149, 2008.
Barreyro, L., et. al., "Overexpression of interleukin 1 receptor accessory protein in stem and progenitor cells and outcome correlation in AML and MDS," Blood, 2012.
Boldin, M.P., et al., "miR-146a is a significant brake on autoimmunity, myeloproliferation and cancer in mice", J. Exp. Med. 208, pp. 1189-1201, 2011.
Breccia, M., et al., "Nf-kappaB as a potential therapeutic target in myelodysplastic syndromes and acute myeloid leukemia", Expert opinion on therapeutic targets, 14, pp. 1157-1176, 2010.
Camos, M., et al., "Gene expression profiling of acute myeloid leukemia with translocation t(8;16)(p11;p13) and MYST3-CREBBP rearrangement reveals a distinctive signature with a specific pattern of HOX gene expression", Cancer Res, 66, pp. 6947-6954, 2006.
Chen, G, et al., "Distinctive gene expression profiles of CD34 cells from patients with myelodysplastic syndrome characterized by specific chromosomal abnormalities", Blood, 104, pp. 4210-4218, 2004.
Chen, J., et al., "ToppGene Suite for gene list enrichment analysis and candidate gene prioritization", Nucleic Acids Res, 37, pp. W305-311, 2009.
Conze, D.B., et al., "Lys63-linked polyubiquitination of IRAK-1 is required for interleukin-1 receptor- and toll-like receptor mediated NF-kappaB activation", Mol Cell Biol, 28, pp. 3538-3547, 2008.
Corey, S.J., et al., "Myelodysplastic syndromes: the complexity of stem-cell diseases", Nat Rev Cancer, 7, pp. 118-129, 2007.
Durand-Reville, T., et al., "IRAK modulators for treating an inflammatory condition, cell proliferation disorder, immune disorder", In, (Biogen Idec.), 2008.
Ebert, B.L., "The biology and treatment of myelodysplastic syndrome", Hematology/oncology clinics of North America, 24, pp. xiii-xvi, 2010.
Fang, J., et al., "Cytotoxic effects of bortezomib in myelodysplastic syndrome/acute myeloid leukemia depend on autophagy-mediated lysosomal degradation of TRAF6 and repression of PSMA1", Blood, 2012.

(Continued)

*Primary Examiner* — Amy Bowman
(74) *Attorney, Agent, or Firm* — Frost Brown Todd LLC

(57) ABSTRACT

Disclosed are compositions and methods for the treatment of disorders such as myelodysplastic syndrome (MDS) and acute myeloid leukemia (AML). The disclosed methods include administering to an individual in need of such treatment a composition that may include an IRAK1/4 inhibitor. In other aspects, the method may include administration of a BLC2 inhibitor.

10 Claims, 41 Drawing Sheets

(56) References Cited

OTHER PUBLICATIONS

Flannery, S., et al., "The interleukin-1 receptor-associated kinases: critical regulators of innate immune signaling", Biochem Pharmacol, 80, pp. 1981-1991, 2011.
Gondek, L.P., et al., "Chromosomal lesions and uniparental disomy detected by SMP arrays in MDS, MDS/MPD, and MDS-derived AML", Blood, 111, pp. 1534-1542, 2008.
Greenberg, P., et al., "International scoring system for evaluating prognosis in myelodysplastic syndromes", Blood, 89, pp. 2079-2088, 1997.
Greenberg, P.L., "Current therapeutic approaches for patients with myelodysplastic syndromes", Br J Haematol, 150, pp. 131-143, 2010.
Hofmann, W.K., et al., "Characteriszation of gene expression of CD34+ cells from normal and myelodysplastic bone marrow", Blood, 100, pp. 3553-3560, 2002.
Kollewe, C., et al., "Sequential autophosphorylation steps in the interleukin-1 receptor-associated kinase-1 regulate its availability as an adapter in interleukin-1 signaling", J Biol Chem, 279, pp. 5227-5236, 2004.
Kristinsson, S.Y., et al., "Chronic immune stimulation might act as a trigger for the development of acute myeloid leukemia or myelodysplastic syndromes", J. Clin Oncol, 29, pp. 2897-2903, 2011.
Martin, M.G., et al., "Limited engraftment of low-risk myelodysplastic syndrome cells in NOD/SCID gamma-C chain knockout mice", Leukemia, 24, pp. 1662-1664, 2011.
Matsuoka, A., et al., "Lenalidomide induces cell death in an MDS-derived cell line with deletion of chromosome 5q by inhibition of cytokinesis", Leukemia, 24, pp. 748-755, 2010.
Ngo, V.N., et al., "Oncogenically active MYD88 mutations in human lymphoma", Nature, 470, pp. 115-119, 2010.
Nimer, S.D., "Myelodysplastic syndromes", Blood, 111, pp. 4841-4851, 2008.
O'Dwyer, M.E., et al., "ST1571 as a targeted therapy for CML", Cancer Invest, 21, pp. 429-438, 2003.
Park, C., et al., "Hematopoietic Stem Cells Are the Disease-Initiating Cells in the Myelodysplastic Syndromes", Paper presented at: ASH Annual Meeting, (San Diego, CA) 2011. Abstract Only.
Pellagatti, A., et al. "Gene expression profiles of CD34+ cells in myelodysplastic syndromes: involvement of interferon-stimulated genes and correlation to FAB subtype and karyotype", Blood, 108, pp. 337-345, 2006.
Pellagatti, A., et al. "Deregulated gene expression pathways in myelodysplastic syndrome hematopoietic stem cells", Leukemia, 24, pp. 756-764, 2010.
Powers, J.P., et al., "Discovery and initial SAR inhibitors of interleukin-1 receptor-associated kinase-4", Bioorganic & Medicinal Chemistry Letters, Pergamon, Amsterdam, NL, vol. 16, No. 11, Jun. 1, 2006, pp. 2842-2845.
Sekeres, M.A., "Are we nearer to curing patients with MDS?", Best Preact Res Clin Haematol, 23, pp. 481-487, 2010a.
Sekeres, M.A., "The epidemiology of myelodysplastic syndromes", Hematology/oncology clinics of North America, 24, pp. 287-294, 2010b.
Sokol, L., et al., "Identification of a risk dependent microRNA expression signature in myelodysplastic syndromes", Br J Haematol, 153, pp. 24-32, 2011.
Starczynowski, D.T., et al., "Innate immune signaling in the myelodysplastic syndromes", Henatol Oncol Clin North Am, 24, pp. 343-359, 2010.
Starczynowski, D.T., et al., "Identification of miR-145 and miR-146a as mediators of the 5q-syndromw phenotype", Nat Med, 16, pp. 49-58, 2010.
Starczynowski, D.T., et al., "MicroRNA-146a disrupts hematopoietic differentiation and survival", Exp Hematol, 39, pp. 167-178, e164, 2011a.
Starczynowski, D.T., et al., "Genome-wide identification of human microRNAs located in leukemia-associated genomic alterations", Blood, 117, pp. 595-607, 2011b.
Starczynowski, D.T., et al., "TRAF6 is an amplified oncogene bridging the RAS and NF-kappaB pathways in human lung cancer", J Clin Invest, 121, pp. 4095-4105, 2011.
Subramanian, A., et al. "Gene set enrichment analysis: a knowledge-bases approach for interpreting genome-wide expression profiles", Proc Natl Acad Sci USA, 102, pp. 15545-15550, 2005.
Taganov, K.D., et al., "NF-kappaB-dependent induction of microRNA miR-146, an inhibitor targeted to signaling proteins of innate immune responses", Proc Natl Acad Sci USA, 103, pp. 12481-12486, 2006.
Tehranchi, R., et al., "Persistent malignant stem cells in del(5q) myelodysplastic in remission", N. Engl J Med, 363, pp. 1025-1037, 2010.
Thomadaki, H., et al., "Molecular profile of the BCL2 family of the apoptosis related genes in breast cancer cells after treatment with cytotoxic/cytostatic drugs", Connect Tissue Res, 49, pp. 261-264, 2008.
Tohyama, K., et al., "A novel factor-dependent human myelodysplastic cell line, MDS92, contains haemopoietic cells of several lineages", Br J Haimatol, 91, pp.795-799, 1995.
Tse, C., et al., "ABT-263: a potent and orally bioavailable Bcl-2 family inhibitor", Cancer Res, 68, pp. 3421-3428, 2008.
Valk, P.J., et al., Prognostically useful gene-expression profiles in acute myeloid leukemia, N Engl J Med, 350, pp. 1617-1628, 2004.
Vanderwerf, S.M., et al., "TLR8-dependent TNF-(alpha) overexpression in Fanconi anemia group C cells," Blood, 114, pp. 5290-5298, 2009.
Vasikova, A., et al., "A distinct expression of various gene subsets in CD34+cells from patients with early and advanced myelodysplastic syndrome", Leuk Res, 34, pp. 1566-1572, 2010.
Wang, Z., et al., "IRAK-4 Inhibitors for Inflammation", Current Topics in Medicinal Chemistry, May 1, 2009, pp. 727-734.
Wei, Y., et al., "Deregulation of TLR2-JMJD3 Innate Immunity Signaling, Including a Rare TLR2 SNP As a Potential Somatic Mutation, in Myelodysplastic Syndromes (MDS)", In American Society of Hematology, (Atlanta, GA) 2012. Abstract Only.
Wunderlich, M, et al. "AML xenograft efficiency is significantly improved in NOD/SCID-IL2RG mice constitutively expressing human SCF, GM-CSF and IL-3," Leukemia, 2010, 24:1785-1788.
Yang, Y.F., et al., "Interleukin-1 receptor associated kinases-1/4 inhibition protects against acute hypoxia/ischemia-induced neuronal injury in vivo and in vitro", Neuroscience, 196, pp. 25-34, 2011.
Zhao, J.L., et al., "NF-kappaB dysregulation in micro-RNA-146a-deficint mice drives the development of myeloid malignancies", Proc Natl Acad Sci USA, 108, pp. 9184-9189, 2011.

\* cited by examiner

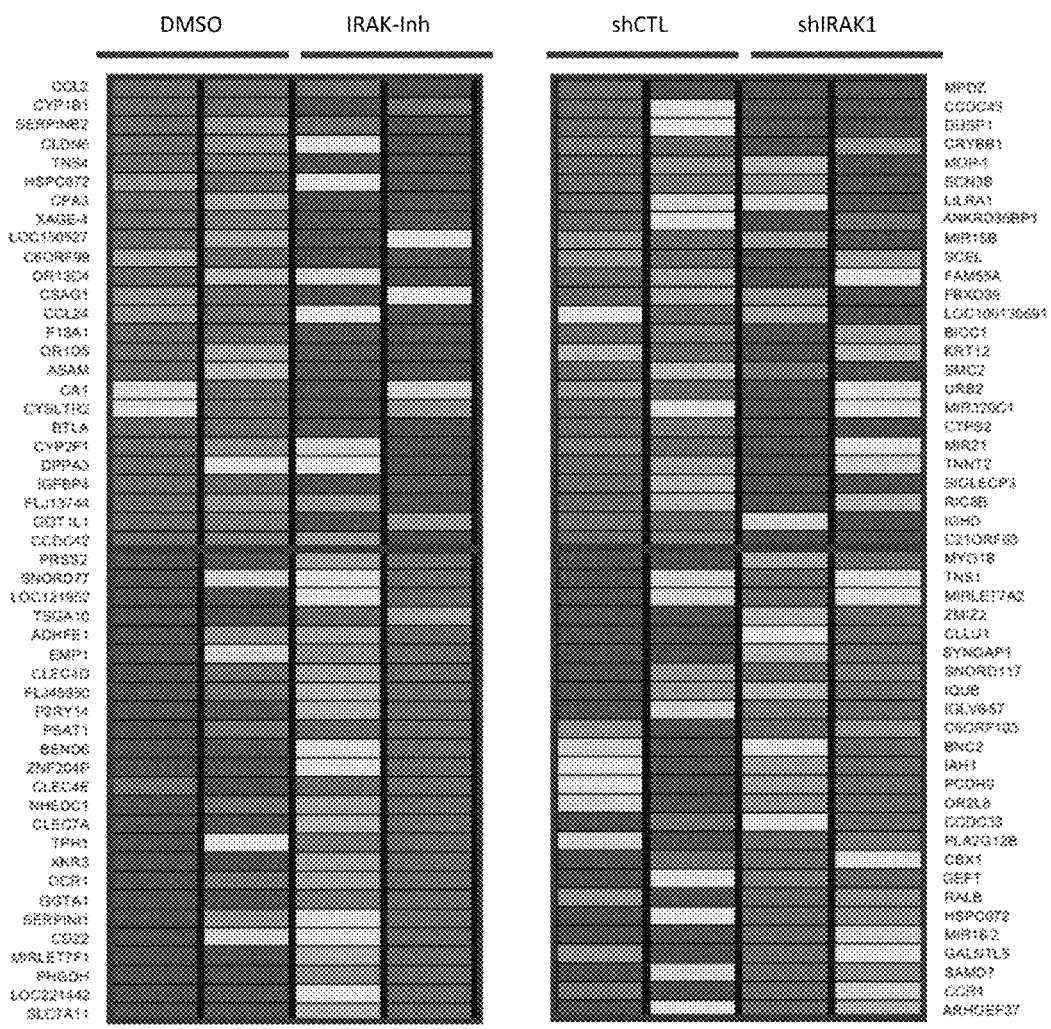

FIG 6B

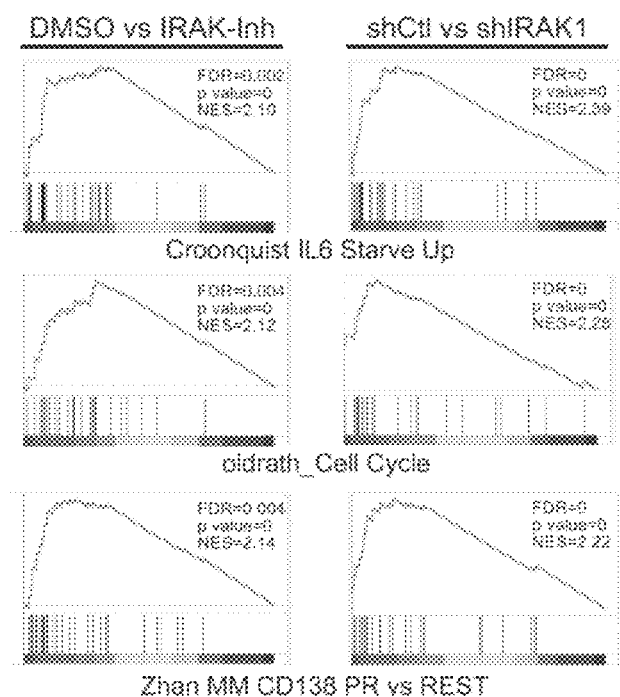

FIG 6C

IRAK-Inh Gene Signature

| Pathway Name | GO# | p value | Select genes |
|---|---|---|---|
| cell migration and adhesion | 0016477, 0007155 | .000036 | CD22,CX3CR1,IL8,PTPRM,CYTIP,CYP1B1,SERPIN1,OLR1 |
| inflammatory response | 0006954, 0002376 | .00013 | TLR6,SLC7A11,BMP6,CXCR5,IL8,RAG2,CCL2,OLR1 |
| cytokine-mediated signaling pathway | 0019221 | .0011 | CX3CR1,IL9R,OAS2,CCL2 | shIRAK1 Gene Signature

| Pathway Name | GO# | p value | Select genes |
|---|---|---|---|
| nucleosome and chromatin assembly | 0000334, 0031497 | .000001 | HIST1H1C,HIST1H2BB,HIST1H2AG,HIST1H2AH |
| regulation of DNA binding | 0051101, 0090046 | .00026 | PSMD10,JUN,TNFSF4,ARID5B,FOS,HIPK3,IRAK1 |
| regulation of RNA metabolic process | 0051253 | .0011 | NR1H2,SIRT4,TNFSF4,ARID5B,FOSB,GFI1B |

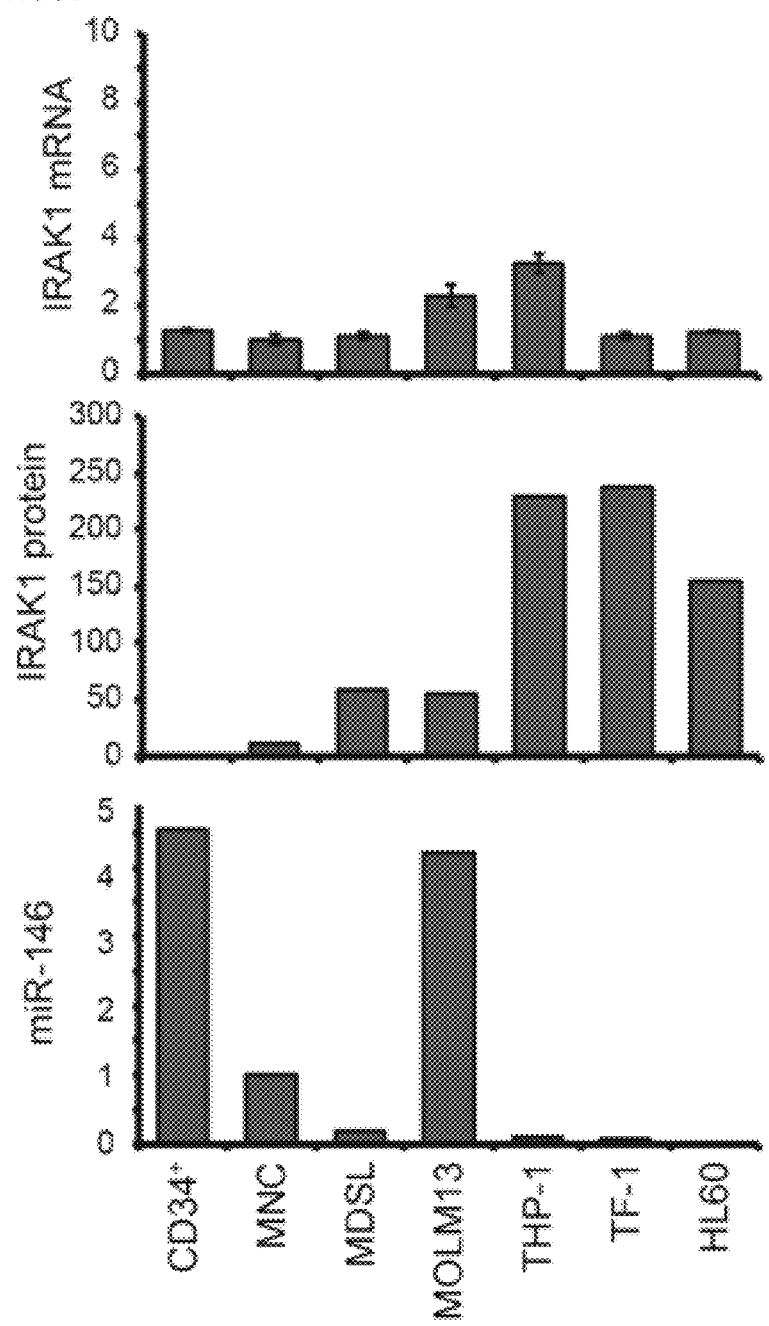

COMBINATION THERAPY FOR MDS

CROSS-REFERENCE TO RELATED APPLICATIONS

This application is a continuation of and claims the benefit of U.S. application Ser. No. 14/842,049 filed Sep. 1, 2015, which is a continuation of and claims the benefit of U.S. application Ser. No. 14/284,521, filed May 22, 2014, which claims the benefit of U.S. Application Ser. No. 61/826,211, filed May 22, 2013, both of which are incorporated herein by reference in their entirety for all purposes.

GOVERNMENT SUPPORT CLAUSE

This invention was made with government support under HL111103 awarded by the national Institutes of Health. The government has certain rights in this invention.

BACKGROUND

Myelodysplastic Syndromes (MDS) are malignant, potentially fatal blood diseases that arise from a defective hematopoietic stem/progenitor cell. MDS are heterogeneous diseases with few treatment options. One of the key challenges facing MDS treatment is the lack of effective medicines capable of providing a durable response.

MDS are hematologic malignancies defined by blood cytopenias due to ineffective hematopoiesis, and a predisposition to acute myeloid leukemia (AML) (Corey et al., 2007; Nimer, 2008). MDS is most prominent in individuals over 60 years of age, and as a result of longer life expectancies, the incidence of MDS has escalated in recent years (Sekeres, 2010b). MDS is fatal in majority of patients as a result of marrow failure, immune dysfunction, and/or transformation to overt leukemia. Current treatment options for MDS include allogeneic HSC transplantation, demethylating agents, and immunomodulatory therapies (Ebert, 2010). At present, the only curative treatment for MDS is (hemopoietic stem cell) HSC transplantation, an option unavailable to many of the older patients. Instead, these patients receive supportive care and transfusions to ameliorate their disease complications. Unfortunately, even with this treatment, the MDS clones persist in the marrow and the disease invariably advances (Tehranchi et al., 2010). For advanced disease or high-risk MDS, patients may also receive immunosuppressive therapy, epigenetic modifying drugs, and/or chemotherapy (Greenberg, 2010). Despite recent progress, most MDS patients exhibit treatment-related toxicities or relapse (Sekeres, 2010a). Overall the efficacy of these treatments is variable, and generally life expectancies are only slightly improved as compared to supportive care.

Approximately 30% of MDS patients also develop aggressive Acute Myeloid leukemia (AML) due to acquisition of additional mutations in the defective hematopoietic stem/progenitor cell (HSPC) (Greenberg et al., 1997). AML is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages. Several risk factors and chromosomal abnormalities have been identified, but the specific cause is not clear. As an acute leukemia, AML progresses rapidly and is typically fatal within weeks or months if left untreated. The prognosis for AML that arises from MDS has a worse as compared to other types of AML.

Consequently, there is an urgent need to develop targeted therapies capable of eliminating the MDS-initiating clones, and for treatments and method of treating MDS and AML. Identification of molecular targets is essential to improve outcome and eliminate the MDS-causing clones and/or AML. Herein, therapeutic targets and agents for treating MDS and/or AML are described.

BRIEF SUMMARY

Disclosed are compositions and methods for the treatment of disorders such as myelodysplastic syndrome (MDS) and acute myeloid leukemia (AML). The disclosed methods include administering to an individual in need of such treatment an IRAK1 inhibitor. In other aspects, the treatment may include administration of a BLC2 inhibitor.

BRIEF DESCRIPTION OF THE DRAWINGS

(FIG. 1A) IRAK1 expression is obtained from two gene expression studies on $CD34^+$ cells isolated from control and MDS marrows (Hofmann et al., 2002; Pellagatti et al., 2010): Pellagatti (p=0.036), Hoffmann (p=0.05) (FIG. 1B) Mononuclear marrow cells from 3 control (MNC) and 5 MDS patients were examined for total and phosphorylated (p)-T209 IRAK1 by immunoblotting. (FIG. 1C) MNC from 2 controls, 3 AML patients, and 1 MDS patient were examined for total and pIRAK1T209 IRAK1 by immunoblotting. (FIG. 1D) MNC and the indicated MDS/AML cell lines were examined for total, pIRAK1T209, and pIRAK1 S376 by immunoblotting. pIRAK1 and IRAK1 were run on parallel gels (left panel). Densitometric values for pIRAK1 protein relative to GAPDH are summarized in the right panel. (FIG. 1E) Normal CD34+ cells, MDSL, and MDS patient marrow cells (MDS-02; same as in [B]) were examined for total and pIRAK1T209 IRAK1 by immunoblotting. (FIG. 1F-FIG. 1G) THP1 cells were treated with 1 μg/ml LPS (F) or 10 ng/ml IL-1β(G) for the indicated time points and analyzed by immunoblotting for total and pIRAK1T209 (left panels). Densitometric values for pIRAK1 protein relative to IRAK1 are summarized in the right panel. Error bars represent ±SD. See also FIG. 8 and Table 1.

(FIG. 2A) Schematic of IRAK1/TRAF6/NF-κB signaling. IRAK-Inh (red line) inhibits IRAK1 kinase function and prevents TRAF6-mediated canonical NF-κB activation. (FIG. 2B) Protein lysates from THP1 cells and (FIG. 2C-FIG. 2D) MDS and AML marrow cells treated with IRAK-Inh for 24 hrs were evaluated by immunoblotting for total and pIRAK1T209. Densitometric values for pIRAK1 protein relative to GAPDH or IRAK1 are shown below. (FIG. 2E) THP1 cells were treated with 10 μM IRAK-Inh for 24 hrs were isolated for immunoprecipitation (IP) of IRAK1. Immunoblot for ubiquitin (Ub) and pIRAK1T209 was performed on the IP lysate. Shown is a representative image from 3 independent replicates. Densitometric values for Ub-IRAK1 protein relative to GAPDH are shown below. (FIG. 2F) Empty vector- and TRAF6-transduced THP1 cells were treated with IRAK-Inh (10 μM) for 24 hrs and examined by immunoblotting. (FIG. 2G) Nuclear lysates from THP1 and HL60 cell-lines treated with IRAK-Inh (10 μM) for 24 hrs were evaluated for p65 DNA binding activity. Shown is the mean of 3 independent replicates. Error bars represent+/−SEM. (FIG. 2H) THP1 cells were treated with 10 μM IRAK-Inh for 24 hrs were isolated for IP of TRAF6. Immunoblot for ubiquitin (Ub) and TRAF6 was performed on the IP lysate. Shown is a representative image from 3 independent replicates. Densitometric values for Ub-TRAF6 protein relative to GAPDH are shown below.

(FIG. 3A) Viable cell growth of the indicated cell lines and normal CD34+ cells was assayed by trypan blue exclusion in the presence of IRAK-Inh (0-10 μM) for up to 6 days. (FIG. 3B) Relationship between IRAK-Inh sensitivity (IC50) and pIRAK1 levels (densitometric values of immunoblotted pIRAK1) was calculated for the indicated cell lines. (FIG. 3C) AnnexinV staining of the indicated cells was determined after 48 hr treatment with IRAK-Inh (10 μM). (FIG. 3D) Cell cycle analysis of MDSL cells treated with 10 μM IRAK-Inh for 6 days was determined by BrdU/7AAD incorporation. (FIG. 3E) Colony formation in methylcellulose was determined for the indicated cell lines treated with IRAK-Inh. Total colonies were scored after 10 days. (FIG. 3F-FIG. 3G) Marrow cells from MDS patients were evaluated for growth (trypan blue exclusion, FIG. 3F) and for apoptosis (AnnexinV staining, FIG. 3G) in the presence of IRAK-Inh.

(FIG. 4A) Two experiment schemes were used to test the efficacy of IRAK-Inh in an MDS xenograft model: (left arm) MDSL cells were pre-treated for 24 hr followed by transplantation into either NSG or NSGS mice; or (right arm) NSG mice were transplanted with MDSL cells and at day 6 mice were given IRAK-Inh (2.12 mg/kg i.p. 3×/week). (FIG. 4B) Overall survival was determined for NSG (n=4-5/group) and NSGS (n=3-5/group) mice transplanted with MDSL cells treated with IRAK-Inh. (FIG. 4C) Complete blood counts were performed at 68 (NSG) and 28 (NSGS) weeks post xenograftment of NSG and NSGS mice. Shown are red blood cells (RBC), hemoglobin (Hb), hematocrit (HCT), and platelets (PLT) for mice receiving control- or IRAK-Inh-treated MDSL cells. (FIG. 4D) Flow cytometric analysis examining peripheral human graft in representative DMSO and IRAK-Inh NSG mice 28 days post-transplant. (FIG. 4E) Wright-Giemsa marrow cytospins and blood smears from represented mice transplanted with control or IRAK-Inh-treated MDSL cells. Smears on all mice were performed at time of death of the control group. MDSL cells are indicated by arrowheads. Blood scale bar, 30 μm; BM scale bar, 5 μm. (FIG. 4F) NSG animals were transplanted with 1×10$^6$ cells/mouse. Six days post transplant, mice were injected with IRAK-Inh (2.12 mg/kg, 3×/week). Hematocrit (HCT) and hemoglobin (Hg) counts were performed on the indicated days (>4 mice per group). Error bars represent+/−SD. (FIG. 4G) Human MDSL engraftment was determined by flow cytometry by measuring hCD45 in peripheral blood. (FIG. 4H) Summary of MDSL engraftment in mice receiving IRAK-Inh (n=5 per group). *, $p<0.05$; **, $p<0.01$.

(FIG. 5A) IRAK1 knockdown was confirmed by qRT-PCR in cells expressing a control or shIRAK1-expressing lentiviral vector. (FIG. 5B) AnnexinV staining by flow cytometry was measured after transduction with a shIRAK1-expressing lentiviral vector. (FIG. 5C-FIG. 5D) The indicated cell lines and primary MDS cells were transduced with shRNA-expressing lentiviral vectors (GFP+), sorted for GFP, and then plated in methylcellulose for progenitor colony formation. Colonies were scored 10-14 days after plating. (FIG. 5E) THP1 cells were transduced with a lentiviral vector containing a doxycycline (DOX)-inducible promoter, which drives the expression of an IRAK1-targeting shRNA. Immunoblotting and qRT-PCR confirm knockdown of IRAK1 upon addition of DOX. (FIG. 5F-FIG. 5G) MDSL cells transduced with the inducible shIRAK1 were transplanted into NSG mice (5×10$^6$/mouse). Half the mice received DOX-containing chow 7 days post engraftment. Human MDSL engraftment was determined by flow cytometry by measuring hCD45 in peripheral blood (FIG. 5F) and marrow (FIG. 5G). (Day 60: n=7-8; Day 77: n=7-8). (FIG. 5H) Spleen size is shown from a representative experiment at time of death. (FIG. 5I) Overall survival was determined for NSG (n=12/group) mice transplanted with MDSL cells transduced with the inducible shIRAK1 (with our without DOX-containing chow). *, $p<0.05$. Error bars represent+/−SD.

FIG. 6A-F. Integrated gene expression profiling of MDS cells following IRAK1 inhibition or deletion. (FIG. 6A) Microarray analysis was performed on MDSL cells transduced with shIRAK1 (or shRNA control) or treated for 48 hr with IRAK-Inh (or DMSO). Only the top 50 differentially expressed genes are shown. GSEA was performed for both experiments in order to determine an overlapping gene signature for IRAK1 depletion. (FIG. 6B) Shown are the three overlapping GSEA profiles (from the top 10) generated from shIRAK1 and IRAK-Inh MDSL gene signatures. (FIG. 6C) Shown are enriched GO pathways generated by Toppgene for shIRAK1 and IRAK-Inh MDSL cells. P values are shown only for the top GO pathway in each group. (FIG. 6D) BCL2 mRNA expression in MDSL treated with IRAK1 inhibitor (10 μm) or transduced with shIRAK1 adapted from the microarray analysis. Error bars represent ±SD. (FIG. 6E) MDSL cells were treated with IRAK1 inhibitor (10 μM) or shIRAK1 expression induced with DOX for 24 hr. Immunoblot analysis was performed to measure BCL2-family protein levels. (FIG. 6F) Densitometric values for BCL2 protein relative to GAPDH are summarized for the indicated cell lines treated with 10 μM IRAK-Inh.

(FIG. 7A) Viable cell growth of the indicated cell lines was assayed by trypan blue exclusion in the presence of IRAK-Inh (10 μM), ABT-263 (0.1 μM) or with the combination of both drugs. (FIG. 7B) AnnexinV/7AAD staining by flow cytometry after 48 hr treatment with IRAK-Inh (10 μM), ABT-263 (0.1 μM) or the combination of both drugs. (FIG. 7C) The indicated cell lines were evaluated for colony formation in methylcellulose in the presence of IRAK-Inh (10 μM), ABT-263 (0.1 μM) or the combination of both drugs. (FIG. 7D-FIG. 7F) Marrow cells from MDS (MDS-02) and AML patients (AML-01 and AML-02) were plated in methylcellulose containing IRAK-Inh (10 μM), ABT-263 (0.1 μM), or the combination of both drugs. (FIG. 7G) As in FIG. 4A, overall survival was determined for NSGS mice transplanted with MDSL cells treated with IRAK-Inh, ABT-263, or with the combination of both drugs for 72 hrs. To the right, p values are shown for the various experimental combinations. *, $p<0.05$; , $p<0.01$; *, $p<0.001$. Error bars represent ±SD.

FIG. 8A-G. Deregulation of IRAK1 in MDS by miR-146a. (FIG. 8A) RNA isolated from MDS patient marrow cells (n=20) was evaluated for IRAK1 mRNA. Shown is IRAK1 mRNA from MDS patients relative to the median expression from control marrow cells (n=10; dashed line).

MDS patients were divided into low (below 1.0) and high (above 1.0) IRAK1 expression. (FIG. 8B) Overall survival was determined for the MDS patients according to high and low IRAK1 expression. (FIG. 8C) IRAK1 mRNA (qRT-PCR), IRAK1 protein (immunoblot), and miR-146a (qRT-PCR) were determined for the indicated cells and normalized to normal mononuclear cells (MNC). Error bars represent+1–SD. (FIG. 8D) MDSL cells were transduced with a miR-146a decoy (pGK-GFP) as previously described (Starczynowski et al., 2010). Endogenous miR-146a expression was reduced by ~75% (not shown). Expression of IRAK1 and TRAF6 was determined by immunoblotting and compared to vector-transduced cells. (FIG. 8E-FIG. 8F) Total (FIG. 8E) and phosphorylated (FIG. 8F) IRAK1 was quantitated and compared to miR-146a expression in the indicated cells. (FIG. 8G) IRAK1 and miR-146a expression was compared in MDS patient marrow cells (n=20).

(FIG. 9A) Protein lysates from MDSL cells treated with IRAK-Inh (0.1M) for 24 hrs were evaluated by immunoblotting for kinases that can be targeted by IRAK-Inh in non-hematopoietic cells and at higher concentrations: IRAK1 ($IC_{50}$=0.3 µM); IRAK4 ($IC_{50}$=0.2 µM); pp60$^{Src}$ ($IC_{50}$>10 µM); and Lck ($IC_{50}$>10 µM) (Powers et al., 2006). Densitometric values for phosphorylated relative to unphosphorylated proteins and GAPDH are shown to the right. (FIG. 9B) THP1 cells were transduced with empty vector-, IRAK1-, or TRAF6-containing LeGO-iG2 lentiviral vectors. Immunoblots were carried out to confirm IRAK1 and TRAF6 overexpression (FIG. 9C) and to examine pIRAK1 T2(19 and GAPDH when treated with IRAK-Inh (µM) Densitometric values for pIRAK1 relative to GAPDH are shown below and normalized to 0 µM.

(FIG. 10A) Primary AML cells were cultured in the presence of 10 µM IRAK-Inh for 48 hr and assayed for apoptosis by 7AAD and Annexin V staining. (FIG. 10B) Primary AML samples were cultured for the indicated time with 10 µM of IRAK-Inh and assayed for growth by trypan blue exclusion. (FIG. 10C) CD34$^+$ cord blood cells, plated with either DMSO, IRAK-Inh (10 µM), ABT-263 (0.1 µM), or with the combination of both drugs, were evaluated for colony formation in methylcellulose assay (left panel). Colonies were scored as either granulocytic (G), macrocytic (G), mixed granulocytic/macrocytic (GM), erythroid (E), or mixed granulocytic, erythrocytic, macrocytic, megakaryocytic (GEMM) colonies (right panel). (FIG. 10D) Schematic of experimental design: human CD34$^+$ cells and a panel of MDS/AML cell lines were treated with IRAK-Inh (10 µM) for 24 hrs and then plated in methylcellulose. (FIG. 10E) Colony formation was determined after 10 days. (FIG. 10F) As in (FIG. 10E), primary MDS patient marrow cells were treated with DMSO or IRAK-Inh (10 µM) for 24 hrs and then plated in methylcellulose to assay progenitor frequency. (FIG. 10G) Representative cytospins of the MDSL cells exposed to either DMSO or IRAK-Inh (10 µM) for 24 hr. Scale bar, 5 µM. (FIG. 10H-FIG. 10I) TRAF6-expressing cells were treated with IRAK-Inh and assessed for cell viability (H; trypan blue exclusion) and colony formation in methylcellulose (FIG. 10I). (FIG. 10J-FIG. 10K) Colony formation in methylcellulose was determined for 2 AML samples treated with IRAK-Inh. Total colonies were scored after 10 days. *, p<0.05. Error bars represent ±SD.

(FIG. 11A) MDSL cells (1×10$^6$) were transplanted into NSG mice. At time of disease, bone marrow (BM), spleen (SP), and blood (PB) were collected and analyzed for engraftment. In addition, BM, SP, and PB were stained with Wright-Giemsa. Scale bar, 5 µm. (FIG. 11B) Blood counts performed at time of death for NSGS mice (n=3) indicate pancytopenia. As a control, sublethaly (250Gy) irradiated NSGS mice were transplanted with normal umbilical cord blood (UCB) CD34$^+$ cells and blood counts measured at 10 weeks post-transplant (n=8). (FIG. 11C) Bone marrow cellularity was determined for healthy NSG mice (HC) (n=6), irradiated mice transplanted with normal CD34' cells (n=5), and irradiated mice transplanted with MDSL cells (n=5). Cellularity for mice transplanted with MDSL cells was determined when mice became moribund. (FIG. 11D) Marrow engraftment over time was determined at the indicated times by performing a femoral aspirate and calculated by quantifying human CD45+CD33$^+$ cells.

(FIG. 12A) MDSL and CD34$^+$ human cord blood cells were transduced with pLKO.1 lentiviral vectors containing 2 independent shRNAs targeting IRAK1. IRAK1 mRNA levels were quantified by qRT-PCR at day 4 post-transduction. (FIG. 12B) Immunoblots were performed to quantify IRAK1 protein expression levels following lentiviral transduction of THP1 cells with either empty vector or two independent shRNAs targeting IRAK1. (FIG. 12C) Colony forming assays were carried out on MDSL cells transduced with pLKO.1 empty vector, or IRAK1-targeting shRNA containing vectors. (FIG. 12D) Domain architecture of doxycycline (DOX)-inducible TRIPZ shIRAK1 lentiviral construct. TRE, Tet-inducible promoter; RFP, red fluorescent protein; UBC, promoter. The shIRAK1 hairpin targets the 3'-UTR of IRAK1. (FIG. 12E) Viable cell growth of the TF-1 cell line transduced with TRIPZ shIRAK1, in the presence of absence of DOX. (FIG. 12F) Apoptosis was evaluated by flow cytometry of TF-1 cells transduced with TRIPZ shIRAK1 48 hrs after addition of DOX. (FIG. 12G-FIG. 12H) TF1 expressing the TRIPZ shIRAK1 were transduced with vector (pLeGO-iG2) or lRAK1 cDNA that is resistant to the shIRAK1 hairpin (lacks the 3'UTR hairpin binding site). Following transduction and sorting (GFP+), cells were treated with DOX or vehicle control for 5 days and analyzed for IRAK1 expression by immunoblotting (FIG. 12G) and for AnnexinV staining (FIG. 12H). The IRAK1 immunoblot is shown after a short and long exposure. (FIG. 12I) Flow cytometric analysis of bone marrow (BM), spleen (SP) and peripheral blood (PB) of moribund NSG animals injected with TRIPZ shIRAK1-transduced MDSL. Flow plots were initially gated on viable, and then hCD45+ cells. Increase in RFP indicates expression of shIRAK1 in vivo. (FIG. 12J) Parental MDSL cells (1×10$^6$) were transplanted into irradiated NSG mice and administered doxycycline (DOX). Addition of DOX did not alter the disease in mice receiving parental MDSL cells. *, p<0.05. Error bars represent ±SD.

(FIG. 13A) MDSL cells were treated with increasing concentrations of ABT-263 (0, 0.01, 0.1, and 1.0 µM) and IRAK-Inh (0, 0.1, 1.0, 5.0, and 10 µM) alone or in combination for 72 hrs. Surviving fraction of MDSL cells was determined by AnnexinV/Pl staining and the live fraction values are shown inside the box. (FIG. 13B) Cells were treated with 0.1 µM ABT-263 and increasing concentration of IRAK-Inh. Note the cooperative cytotoxic effect of 0.1 µM ABT-263 with increasing concentrations of IRAK-lnh. (FIG. 13C) Cells were treated with 10 µM IRAK-Inh and increasing concentration of ABT-263. Note the cooperative cytotoxic effect of 10 µM IRAK-Inh and 0.1 µM ABT-263. Dotted line represents the dose at which 50% of cells are alive for ABT-263 and in combination with IRAK-Inh.

DETAILED DESCRIPTION

Figure 1A:
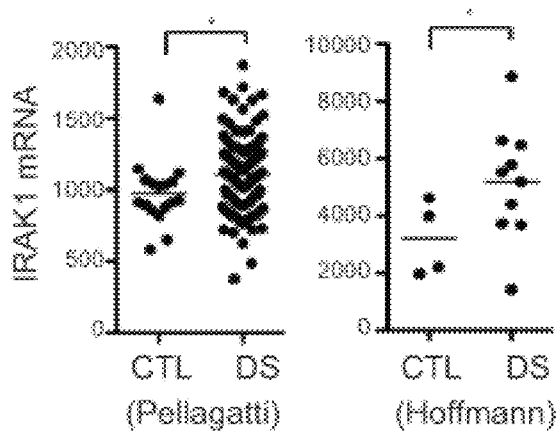
FIG. 1A-1G. IRAK1 is overexpressed and overactivated in MDS.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

The terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation, and may further encompass "pharmaceutically acceptable excipients" as defined herein.

As used herein, "pharmaceutically acceptable excipient" means any other component added to a pharmaceutical formulation other than the active ingredient and which is capable of bulking-up formulations that contain potent active ingredients (thus often referred to as "bulking agents," "fillers," or "diluents") to allow convenient and accurate dispensation of a drug substance when producing a dosage form. Excipients may be added to facilitate manufacture, enhance stability, control release, enhance product characteristics, enhance bioavailability drug absorption or solubility, or other pharmacokinetic considerations, enhance patient acceptability, etc. Pharmaceutical excipients include, for example, carriers, fillers, binders, disintegrants, lubricants, glidants, colors, preservatives, suspending agents, dispersing agents, film formers, buffer agents, pH adjusters, preservatives etc. The selection of appropriate excipients also depends upon the route of administration and the dosage form, as well as the active ingredient and other factors, and will be readily understood by one of ordinary skill in the art.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

Targeted therapies have been effective in other myeloid diseases (O'Dwyer et al., 2003), and may also improve the clinical outcome in MDS by suppressing the malignant clone. Recent sequencing and gene profiling efforts have revealed insight into the underlying molecular and cellular defects in MDS-initiating cells. Despite this progress, one of the key challenges still facing MDS treatment is that molecular-targeted therapies do not exist and AML-like therapies have been disappointing.

MDS are genetically defined by somatic mutations and chromosomal abnormalities not only affecting epigenetic plasticity, ribosome function, spliceosome machinery, or activation of oncogenes but also immune dysfunction. Human miR-146a resides on chromosome 5q33.3, and its deletion occurs in 80% of all del(5q) MDS and AML (Gondek et al., 2008). Low expression of miR-146a, also occurs in >25% of all MDS and in >10% of AML patients (Sokol et al., 2011; Starczynowski et al., 2010; Starczynowski et al., 2011b), and is part of an MDS diagnostic miRNA signature (Sokol et al., 2011). Knockout of miR-146a results in an early onset of myeloid expansion in the marrow, and progression to more aggressive diseases such as lymphomas, marrow failure, and myeloid leukemia (Boldin et al., 2011; Zhao et al., 2011).

TRAF6 and IRAK1 are two immune-related targets of miR-146a (Starczynowski et al., 2010; Starczynowski et al., 2011a; Taganov et al., 2006), and as expected, miR-146a knockout mice have a dramatic increase in TRAF6 and IRAK1 protein within the hematopoietic compartment (Boldin et al., 2011; Zhao et al., 2011). TRAF6, a lysine (K)-63 E3 ubiquitin ligase, and IRAK1, a serine/threonine kinase, are interacting proteins and mediators downstream of Toll-like (TLR) and Interleukin-1 (IL1R) receptors. Activation of TLR or IL1R recruits a series of adaptor proteins resulting in phosphorylation of IRAK1 on Thr209. Phosphorylated IRAK1 binds to and activates TRAF6 resulting in NF-κB activation. Increasing clinical and biological data indicate that innate immune signaling is an important determinant of MDS pathophysiology (Bar et al., 2008; Chen et al., 2004; Hofmann et al., 2002; Vasikova et al., 2010).

Here, Applicant has identified that Interleukin Receptor Associated Kinase-1 (IRAK1) is overexpressed and activated in MDS. Genetic or pharmacological inhibition of IRAK1 induces apoptosis and cell cycle arrest of MDS cells, and prolongs survival outcome in a human MDS xenograft model. In an attempt to understand the mechanism of IRAK1/4-Inh function and potential resistance, Applicant identified a collaborative cytotoxic effect of combined IRAK1 and BCL2 inhibition on MDS cells. Applicant's findings suggest that targeting IRAK1 may be an effective therapeutic strategy in MDS.

In particular, Applicant identified that IRAK1, an immune modulating kinase, is overexpressed and hyperactivated in MDS. MDS clones treated with a small-molecule IRAK1 inhibitor (IRAK1/4-Inh) exhibited impaired expansion and increased apoptosis, which coincided with TRAF6/NF-κB inhibition. Suppression of IRAK1, either by RNAi or with IRAK1/4-Inh, is detrimental to MDS cells while sparing normal CD34+ cells. Based on an integrative gene expression analysis, we combined IRAK1 and BCL2 inhibitors and found that co-treatment more effectively eliminated MDS clones. In summary, these findings implicate IRAK1 as a drugable target in MDS.

Disclosed herein are methods for treating myelodysplastic syndrome (MDS) in an individual. The method may comprise the step of administering to the individual a composition that may comprise an IRAK1 inhibitor.

In one aspect, the IRAK1/4 inhibitor may be selected from N-acyl-2-aminobenzimidazoles, imidazo[1,2-a]pyridino-pyrimidine, imidazo[1,2-a]pyridino-pyridine, benzimidazolo-pyridine, N-(2-morpholinylethyl)-2-(3-nitrobenzoylamido)-benzimidazole, (IRAK1/4), or combinations thereof.

In one aspect, the IRAK1/4 inhibitor may comprise an RNAi sufficient to inhibit IRAK1 expression.

In one aspect, the method may comprise the step of administering to the individual an apoptotic modulator.

In one aspect, the method may comprise the step of administering to said individual an apoptotic modulator. The apoptotic modulator comprises may comprise a BCL2 inhibitor.

In one aspect, the method may comprise the step of administering to the individual an apoptotic modulator, wherein the apoptotic modulator may comprise a BCL2 inhibitor selected from ABT-263 (Navitoclax), ABT-737, ABT-199, GDC-0199, GX15-070 (Obatoclax), and combinations thereof, all available from Abbott Laboratories.

In one aspect, the myelodysplastic syndrome may be selected from Fanconi Anemia, refractory anemia, refractory neutropenia, refractory thrombocytopenia, refractory anemia with ring sideroblasts (RARS), refractory cytopenia with multilineage dysplasia (RCMD), refractory anemia with excess blasts I and II (RAEB), 5q-syndrome, myelodysplasia unclassifiable, refractory cytopenia of childhood, or a combination thereof.

In one aspect, the administering step may be selected from orally, rectally, nasally, topically, parenterally, subcutaneously, intramuscularly, intravenously, transdermally, or a combination thereof.

In one aspect, the administration may decrease the incidence of marrow failure, immune dysfunction, transformation to overt leukemia, or combinations thereof in said individual, as compared to an individual not receiving said composition.

In one aspect, the method may decrease a marker of viability of MDS cells. In one aspect, the method may decrease a marker of viability of MDS and/or AML cells. The marker may be selected from survival over time, proliferation, growth, migration, formation of colonies, chromatic assembly, DNA binding, RNA metabolism, cell migration, cell adhesion, inflammation, or a combination thereof.

In one aspect, a method of treating myelodysplastic syndrome or acute myeloid leukemia in an individual is disclosed. In this aspect, the method may comprise the step of administering to the individual
 a) an IRAK1/4 inhibitor; and
 b) an agent selected from an apoptotic agent, an immune modulating agent, an epigenetic modifying agent, and combinations thereof.

In one aspect, the IRAK1/4 inhibitor may be selected from N-acyl-2-aminobenzimidazoles, imidazo[1,2-a]pyridino-pyrimidine, imidazo[1,2-a]pyridino-pyridine, benzimidazolo-pyridine, N-(2-morpholinylethyl)-2-(3-nitrobenzoylamido)-benzimidazole, (IRAK1/4), or combinations thereof. In one aspect, the IRAK1 inhibitor may comprise an RNAi sufficient to inhibit IRAK1 expression.

In one aspect, the administration may comprise administration of an apoptotic modulator. The apoptotic modulator may comprise a BLC2 inhibitor. In certain aspects, the apoptotic modulator may be selected from ABT-263 (Navitoclax), ABT-737, ABT-199, GDC-0199, GX15-070, (Obatoclax), and combinations thereof.

In one aspect, the administration step may comprise administration of an immune modulator. The immune modulator may comprise, for example, Lenalidomide (Revlamid; Celgene Corporation).

In one aspect, the administration step may comprise administration of an epigenetic modulator. The epigenetic modulator may comprise, for example, a hypomethylating agent such as azacitidine, decitabine, or a combination thereof.

The myelodysplastic syndrome may be selected from Fanconi Anemia, refractory anemia, refractory neutropenia, refractory thrombocytopenia, refractory anemia with ring sideroblasts (RARS), refractory cytopenia with multilineage dysplasia (RCMD), refractory anemia with excess blasts I and II (RAEB), 5q-syndrome, myelodysplasia unclassifiable, refractory cytopenia of childhood, or a combination thereof.

The disclosed methods may decrease the incidence of marrow failure, immune dysfunction, transformation to overt leukemia, or combinations thereof in an individual, as compared to an individual not receiving the disclosed composition.

In one aspect, a method of identifying a compound useful for treatment of a myelodysplastic syndrome is disclosed. In this aspect, the method may comprise the steps of
 a) contacting a MDSL cell with a compound of interest;
 b) transplanting the MDSL cell into a host animal;
 c) assaying a marker of MDS in the host animal;
 wherein a decrease in an incidence of the marker of MDS indicates that said compound of interest is a potential therapeutic agent.

In another aspect, a method of identifying a compound useful for treatment of a myelodysplastic syndrome is disclosed. In this aspect, the method may comprise the steps of a) contacting a host animal comprising MDSL cells with a compound of interest;

b) assaying a marker of MDS in said host animal;

wherein a decrease in an incidence of the marker of MDS indicates that the compound of interest is a potential therapeutic agent.

In certain aspects, the marker may comprise, for example, anemia, thrombocytopenia, hypocellular marrow, extramedullary hematopoiesis, or a combination thereof. In other aspects, the marker may comprise viability or overall health of the host animal.

The host animal may be, for example, a mammal, preferably a rodent, more preferably a mouse. In certain aspects, the host animal may be an NSG or NSGS immunodeficient mouse.

Compositions

In one aspect, a composition is disclosed. The composition may comprise an IRAK1/4 inhibitor and a pharmaceutically acceptable excipient or a pharmaceutically acceptable carrier. In other aspects, the composition may further comprise an agent selected from an apoptotic agent, an immune modulating agent, an epigenetic modifying agent, and combinations thereof.

Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations may contain at least 0.1% of active agent. The percentage of the compositions and preparations can, of course, be varied, and can contain between about 2% and 60% of the weight of the amount administered. The percentage of the compositions and preparations may contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The disclosed active agents may form salts. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

Pharmaceutically acceptable salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The compounds can be formulated in various forms, including solid and liquid forms, such as tablets, gel, syrup, powder, aerosol, etc.

The compositions may contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds may also be used enterally. Orally, the compounds may be administered at the rate of 100 μg to 100 mg per day per kg of body weight. Orally, the compounds may be suitably administered at the rate of about 100, 150, 200, 250, 300, 350, 400, 450, or 500 μg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

The compounds may also be administered parenterally in the form of solutions or suspensions for intravenous or intramuscular perfusions or injections. In that case, the compounds may be administered at the rate of about 10 μg to 10 mg per day per kg of body weight; one method of administration may consist of using solutions or suspensions containing approximately from 0.01 mg to 1 mg of active substance per ml. The compounds may be administered at the rate of about 10, 20, 30, 40, 50, 60, 70, 80, 90, or 100 μg to 1, 2, 3, 4, 5, 6, 7, 8, 9, or 10 mg per day per kg of body weight; in one aspect, solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml may be used.

The compounds can be used in a substantially similar manner to other known anti-cancer agents for treating (both chemopreventively and therapeutically) various cancers. For the anti-cancer dose to be administered, whether a single dose, multiple dose, or a daily dose, will of course vary with the particular compound employed because of the varying potency of the compound, the chosen route of administration, the size of the recipient, the type of cancer, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. For example, an oncologist skilled in the art of cancer treatment will be able to ascertain, without undue experimentation, appropriate protocols for the effective administration of the compounds related to cancer therapy, such as by referring to the earlier published studies on compounds found to have anti-cancer properties.

The active compounds and/or pharmaceutical compositions of the embodiments disclosed herein can be administered according to various routes, such as by injection, for example local or systemic injection(s). Intratumoral injections maybe used for treating existing cancers. Other administration routes can be used as well, such as intramuscular, intravenous, intradermic, subcutaneous, etc. Furthermore, repeated injections can be performed, if needed, although it is believed that limited injections will be needed in view of the efficacy of the compounds.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions may include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The compound may be administered such that a therapeutically effective concentration of the compound is in contact with the affected cells of the body. The dose administered to a subject, particularly a human, may be sufficient to effect a therapeutic response in the subject over a reasonable period of time. The dose may be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds may be therapeutically effective at low doses. The generally useful dose range may be from about 0.001 mM, or less, to about 100 mM, or more. The effective dose range may be from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds may be generally administered in low doses.

The pharmaceutical composition may further comprise a pharmaceutically acceptable carrier. The resulting preparation may incorporate, if necessary, one or more solubilizing agent, buffers, preservatives, colorants, perfumes, flavorings and the like that are widely used in the field of pharmaceutical preparation.

The proportion of the active ingredient to be contained in the disclosed compositions may be determined by one of ordinary skill in the art using art recognized methods.

The disclosed compounds may be formulated into a dosage form selected from the group consisting of tablets, capsules, granules, pills, injections, solutions, emulsions, suspensions, and syrups. The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The disclosed compositions may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The compounds can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds may also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions may also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

EXAMPLES

Materials and Methods

Cell Lines and CD34+ Cells

Acute myeloid leukemic cell lines, HL60, THP1, and TF-1 were purchased from the American Type Culture Collection. MOLM13 were purchased from AddexBio. The myelodysplastic cell line, MDS-L, was provided by Dr. Kaoru Tohyama (Kawasaki Medical School, Okayama, Japan) (Matsuoka et al., 2010). Cell-lines were cultured in RPMI 1640 medium with 10% FBS and 1% penicillin-streptomycin. Additionally, both the MDSL and TF-1 cell lines were cultured in the presence of 10 ng/mL human recombinant IL-3 (Stemcell Technologies). Human CD34+ umbilical cord blood (UCB) and adult marrow-derived mononuclear cells were obtained from the Translational Research Development Support Laboratory of Cincinnati Children's Hospital under an approved Institutional Review Board protocol. Human CD34+ UCB cells and primary MDS/AML cells were maintained in StemSpan Serum-Free Expansion Media (Stemcell Technologies) supplemented with 10 ng/mL of recombinant human stem cell factor (SCF), Flt3 ligand (Flt3L), thrombopoietin (TPO), IL-3, and IL-6 (Stemcell Technologies).

Reagents

The IRAK1 inhibitor (IRAK1/4 inhibitor or IRAK-Inh; Amgen Inc.) was purchased from Sigma-Aldrich (I5409). Lipopolysaccharide was purchased from InvivoGen (TLRL-PEKLPS). ABT-263 (Navitoclax) was purchased from Chemietek (CT-A263) (Tse et al., 2008). Recombinant human IL1-β was purchased from PeproTech (200-01B). LeGO-iG2 lentiviral vectors for expression of IRAK1 and TRAF6 cDNAs are described previously (Fang et al., 2012).

Survival Analysis and Growth Curves

Annexin V analysis was carried out as previously described (Fang et al., 2012). Cells were stained after either drug treatment or lentiviral transduction with Annexin V (eBioscience) and propidium iodide (Sigma-Aldrich), or 7AAD (eBioscience) according to the manufacturer's instructions. Analysis was performed using BD FACSCalibur or FACSCanto flow cytometer with either CellQuest or Diva software. For in vitro growth assays, cell expansion in liquid culture was determined based on trypan blue exclusion using an automated cell counter (BioRad TC10). For experiments beyond 48 hrs, cells were replenished with fresh media and drug every second day. For primary patient marrow cells, cell were treated with a single inhibitor dose and counted 24 and 48 hours later. NF-κB DNA-binding assay Nuclear lysates were isolated from treated cells as previously described (Starczynowski et al., 2011). NF-κB (p65) DNA binding was measured using an ELISA-based assay according to the manufacturer's recommendations (KHO0371, Invitrogen)

Immunoblotting and Immunoprecipitation

Total protein lysates were obtained from cells by lysing the samples in cold RIPA buffer (50 mM Tris-HCl, 150 mM NaCl, 1 mM EDTA, 1% Triton X-100 and 0.1% SDS), in the presence of PMSF, sodium orthovanadate, protease and phosphatase inhibitors. After being re-suspended in RIPA cells were briefly sonicated. Protein concentration was evaluated by a BCA assay (Pierce). For immunoprecipitation, TRAF6 or IRAK1 antibodies (2 μg) were added to cell lysates (10 mg) for 3 h at 4° C. and captured by the addition of Protein A/G Plus beads (sc-2003; Santa Cruz) as described before (Starczynowski et al., 2011). The immune complexes were washed with lysis buffer followed by the addition of SDS sample buffer. The bound proteins were separated by SDS-polyacrylamide gel electrophoresis, transferred to nitrocellulose membranes, and analyzed by immunoblotting. Western blot analysis was performed with the following antibodies: TRAF6 (sc-7221; Santa Cruz), IRAK1 (sc-7883; Santa Cruz), ubiquitin (sc-8017; Santa Cruz), IKKβ (2370; Cell Signaling Technology), GAPDH (5174; Cell Signaling Technology), p38 MAPK (9212; Cell Signaling Technology), phopho-p38 MAPK (4631; Cell Signaling Technology), phospho-IKKα/β (2697; Cell Signaling Technology), phospho-IRAK1 (S376) (PAB0497; Abnova), phospho-IRAK1 (T209) (A1074; AssaybioTech), phospho-ERK (4695; Cell Signaling Technology), Lck (2752; Cell Signaling Technology), phospho-Lck (Tyr505) (2751; Cell Signaling Technology), IRAK4 (4363; Cell Signaling Technology), phospho-IRAK4 (Thr345/Ser346) (7652; Cell Signaling Technology), Src (2102; Cell Signaling Technology), Phospho-Src (Tyr416) (2113; Cell Signaling Technology), BCL-2 (2870; Cell Signaling Technology) and Actin (4968; Cell Signaling Technology).

qRT-PCR

Total RNA was extracted using Trizol Reagent (Life Technologies) and reverse transcription was carried out using Superscript VILO (Life Technologies). Quantitative PCR was performed with Taqman Master Mix (Life Technologies) for human IRAK1 (Hs01018347_m1), TRAF6 (Hs04185733_m1), GAPDH (Hs02758991_g1) on an Applied Biosystems StepOne Plus Real-Time PCR System.

shRNA-Mediated Knockdown of IRAK1

Lentiviruses were pseudotyped with VSV-G, produced by 293-FT cells, and concentrated by ultracentrifugation at 20,000 rpm for 2 hours at 4° C. Cells at 1×105/mL were transduced with lentivirus at multiplicity of infection (MOI) of 0.5~1 and in the presence of 8 μg/mL of polybrene (No. TR-1003-G; Millipore). At 48 hours post-transduction, GFP positive cells were isolated by fluorescence-activated cell sorting (FACS). The pLKO.1 (OpenBiosystems) constructs were obtained from the Lentiviral core at CCHMC and used to express shCTL (empty or scrambled control) and shIRAK1. Puromycin resistance gene was replaced by green fluorescent protein (GFP). Two independent and validated pLKO.1-shIRAK1 constructs were obtained: TRCN0000000543 and TRCN0000000544. After validation, majority of experiments were performed with clone TRCN0000000544. For inducible knockdown of IRAK1, we used the TRIPZ doxycycline (DOX)-inducible shRNA system (OpenBiosystems) expressing shIRAK1 clone V2THS-132369.

Xenograftment of NOD/SCID-IL2Rγ(NSG) and NSG-hSCF/hGM-CSF/hIL3 (NSGS) MDSL cells ($1 \times 10^6$-$5 \times 10^6$) were injected into the tail veins of 8-week old sublethally irradiated (250 Gy) NSG or NSG animals engineered to express human SCF, GM-CSF, and IL3 (NSGS) as previously described (Wunderlich et al., 2010). Mice were monitored by performing complete blood counts (Drew Hemavet 950FS). Following red cell lysis, human MDSL cells were identified by hCD45-FITC staining. In vivo delivery of IRAK-Inh approach is adapted from previous reports (Yang et al., 2011): IRAK-Inh was diluted in DMSO (5 mM) and further dissolved in sterile phosphate buffered saline (PBS; pH 7.2). Animals were injected i.p. with 2.12 mg/kg IRAK-Inh 3× weekly.

Microarray Analysis

MDSL cells were transduced with lentivirus targeting human IRAK1 or a non-targeting control. At 2.5 days post-transduction, GFP positive populations were isolated by flow cytometry. Total RNA was extracted and purified with Quick-RNA MiniPrep Kit (Zymogen). RNA quality was tested using the Agilent Bioanalyzer 2100 (Hewelett Packard). Total RNA was reverse transcribed and labeled, and hybridized onto the GeneChip Human Gene 1.0 ST Array (Affymetrix). Scanning was performed with the Affymetrix GeneChip Scanner 3000 7G and evaluated with the Genechip Operating Software (Affymetrix). Data mining was performed with GeneSpring software (Agilent). Gene set enrichment analysis was performed on a JAVA-based dataset supported by the Broad Institute (Subramanian et al., 2005). For evaluation of IRAK1 expression in MDS, previously published data sets were used (Pellagatti et al., 2006; Valk et al., 2004). All microarray data files have been deposited in the Gene Expression Omnibus (accession number GSE46346).

Statistical Analysis

Results are depicted as the mean±standard error of the mean. Statistical analyses were performed using Student's t-test. GraphPad Prism (v5, GraphPad) was used for statistical analysis.

Accession Numbers

The gene expression data from IRAK-Inh and IRAK1 RNAi can be found at the GEO database (http://www.ncbi.nlm.nih.gov/geo) using the accession number GSE46346.

Primary Samples

This study was approved by the Cleveland Clinic (Cleveland, Ohio) and at Fondazione IRCCS Ca'Granda Ospedale Maggiore Policlinico, University of Milan (Milan, Italy). Informed consent was obtained according to protocols approved by the review boards of participating institutions. The study conformed to the ethical standards set out in the Declaration of Helsinki. Diagnoses were reviewed at each of the participating centers and adapted, when required, to WHO 2008 criteria. For qRT-PCR analysis, presentation bone marrow aspirates were collected from 20 patients (CC1-CC20; Table 1). For functional studies, MDS mononuclear cells from bone marrow aspirates were obtained at diagnosis as part of a multicenter phase 2 trial based in Italy (MDS01-MDS08; Table 1). AML patient samples were acquired following informed consent and under the direction of IRB approved protocols. Human CD34+ umbilical cord blood (UCB) and adult marrow-derived mononuclear cells were obtained from Cincinnati Children's Hospital.

Results

IRAK1 is Overexpressed and Activated in MDS.

IRAK1 mRNA expression was evaluated in two gene expression studies comparing normal and MDS CD34+ marrow cells (Hofmann et al., 2002; Pellagatti et al., 2010). Both studies revealed that IRAK1 transcript is overexpressed by approximately 2-fold in ~10-30% of MDS patients (FIG. 1A; p=0.036 and p=0.05, respectively). An independent group of MDS patients segregated according to high (top 50%) and low (bottom 50%) IRAK1 expression revealed that high IRAK1 expression correlates with reduced overall survival (p=0.035). IRAK1 protein expression was similarly overexpressed in marrow cells from 5 low/intermediate-risk MDS patients, 3 AML patients, and in 6 MDS/AML cell lines (FIG. 1B-1E, Table 1), suggesting that IRAK1 may be a relevant molecular target in MDS.

TABLE 1

Patient Characteristics

| ID | Disease | Risk | OS MONTHS | Gender | Age | Cytogenetics |
|---|---|---|---|---|---|---|
| CC1 | RCMD | 0 | 8 | Male | 70 | del(20)(q11.2)/46, idem, del(5)(q12q33) |
| CC2 | RCMD | 0 | 51 | Female | 63 | del(5)(q11.2q33), add(7)(q36), −9, der(14; 21)(q10; q10), add(17)(p13), 18, +21, +mar/47, idem, +2mar |
| CC3 | 5q-Syndrome | 0 | 144 | Female | 57 | del(5q) |
| CC4 | RCMD | 1 | 24 | Female | 80 | del(5)(q15q33), del(7)(q22), −22 |
| CC5 | 5q-Syndrome | 0 | 21 | Female | 72 | del(5)(q15q33) |
| CC6 | RCMD-RS | 0 | 5 | Male | 77 | del(5)(q23q34), +6, +8, +9, −11, +19, +21 |
| CC7 | 5q-Syndrome | 0 | 21 | Female | 58 | del(5)(q13) |
| CC8 | RAEB-1 | 0 | 5 | Male | 58 | del(5)(q22q35)[1]/45, idem, −7 |
| CC9 | RAEB-1 | 1 | 22 | Female | 67 | del(3)(p14), −5, −7, +22 |
| CC10 | RCMD | 1 | 17 | Female | 71 | add(4)(q21), −5, add(8)(p23), −13, −16, add(17)(p11.2), −18 |
| CC11 | RAEB-2 | 1 | 11 | Female | 23 | add(3)(q21), −5, t(7; 12)(q22; p13), −8, der(16)t(8; 16)(q13; q11.2) |
| CC12 | RAEB-2 | 1 | 2 | Male | 75 | add(3)(q11.2), del(5)(q13q33), +8, −15, −16 |
| CC13 | RAEB-1 | 0 | 26 | Female | 78 | del(5)(q15q33) |
| CC14 | RCMD | 1 | 8 | Male | 79 | del(1)(p21), del(3)(q21q26.2), inv(3)(q21q26.2), add(5)(q22), −6, add(7)(q22), −10, add(11)(q23), −12, −17 |
| CC15 | 5q-Syndrome | 0 | 46 | Female | 62 | del(5q) |
| CC16 | RAEB-1 | 1 | 4 | Male | 58 | del(1), −3, −5, −7, +9, del(11)(p12) −18 |
| CC17 | RCMD | 1 | 5 | Male | 67 | del(1)(p21), del(3)(q21q26.2), inv(3)(q21q26.2), add(5)(q22), −6, add(7)(q22), −10, add(11)(q23), −12, −17 |
| CC18 | 5q-Syndrome | 0 | 30 | Female | 75 | del(5q) |
| CC19 | RCMD-RS | 0 | 10 | Male | 76 | add(3)(p12), +add(3)(p12), −5, del(5)(q12q33), add(6)(p25), +8, +8, −17, −20, +22 |
| CC20 | RA | 1 | 13 | Female | 72 | del(5)(q12q33), −7, del(7)(q22), del(7)(q22q34), −8, −12, −16, −16, −17, −18, +21 |
| MDS01 | 5q-syndrome | 0 | na | Female | na | del(5q) |
| MDS02 | 5q-syndrome | 0 | na | Female | na | del(5q) |
| MDS03 | RAEB-1 | 0 | na | male | 65 | del(5q) |
| MDS04 | 5q-syndrome | 0 | na | female | 83 | del(5q) |
| MDS05 | RAEB-2 | 1 | na | male | 62 | na |

Figure 1B:
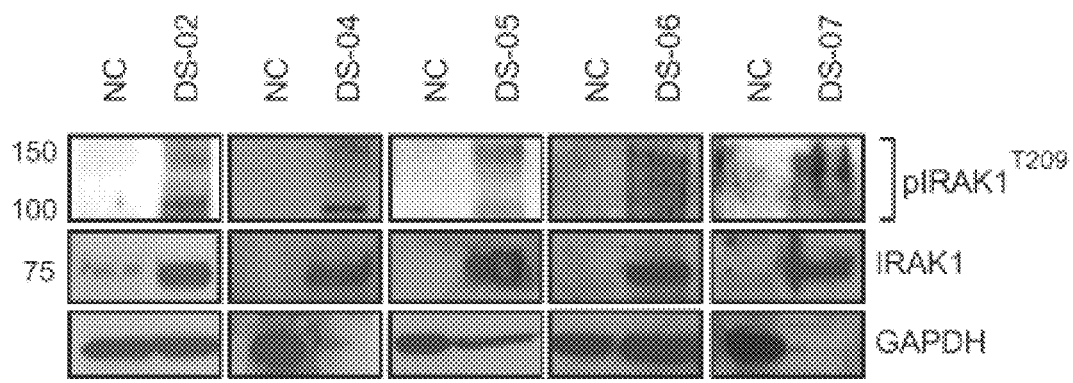
Figure 1C:
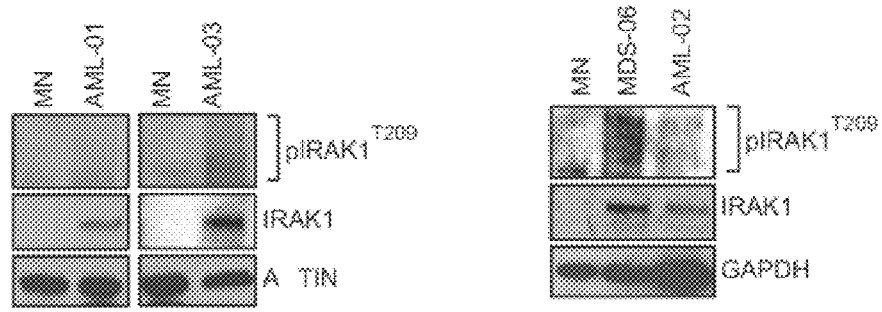
Figure 1D:
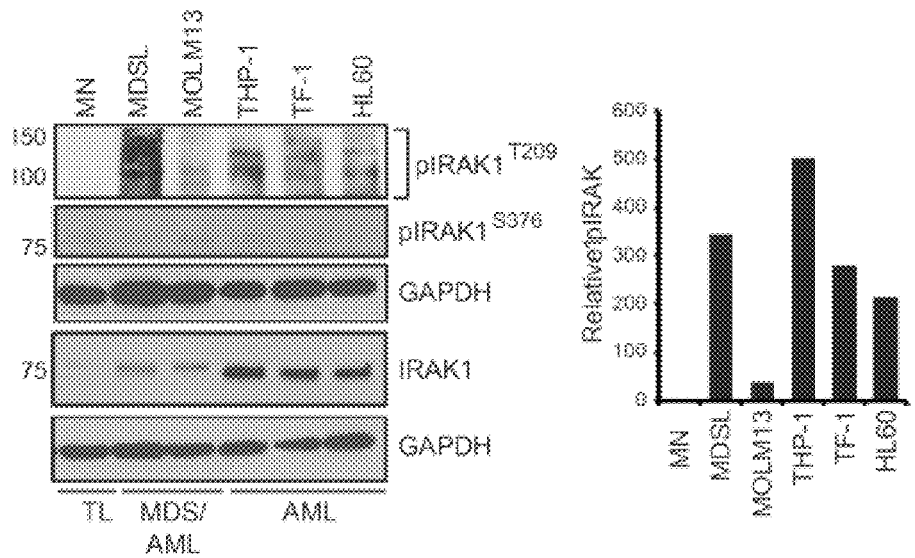
Figure 1E:
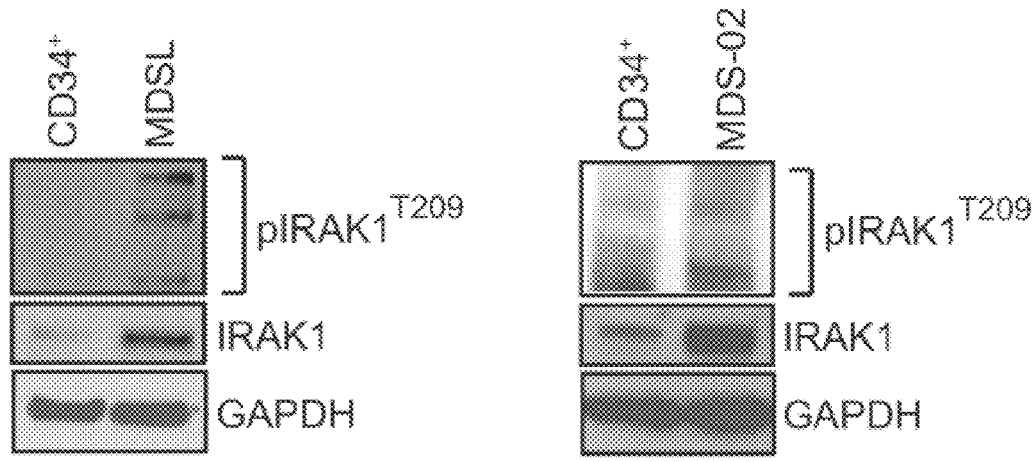
Figure 1F:
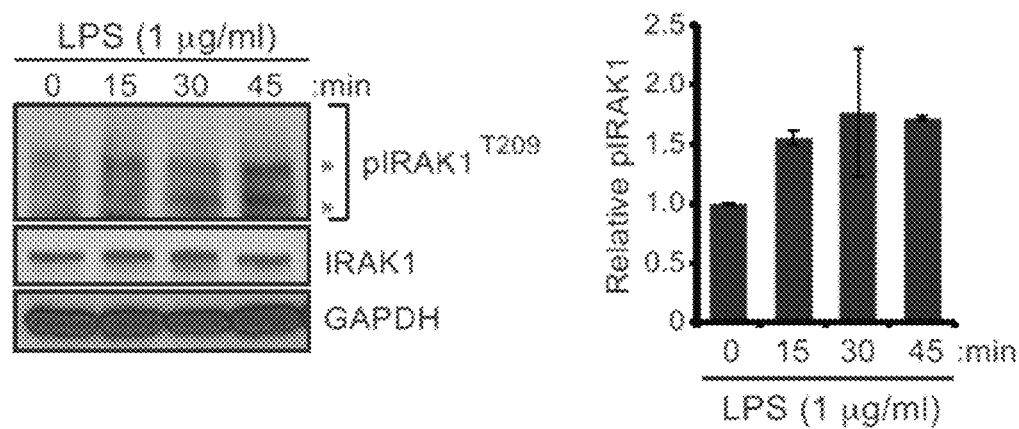
Figure 1G:
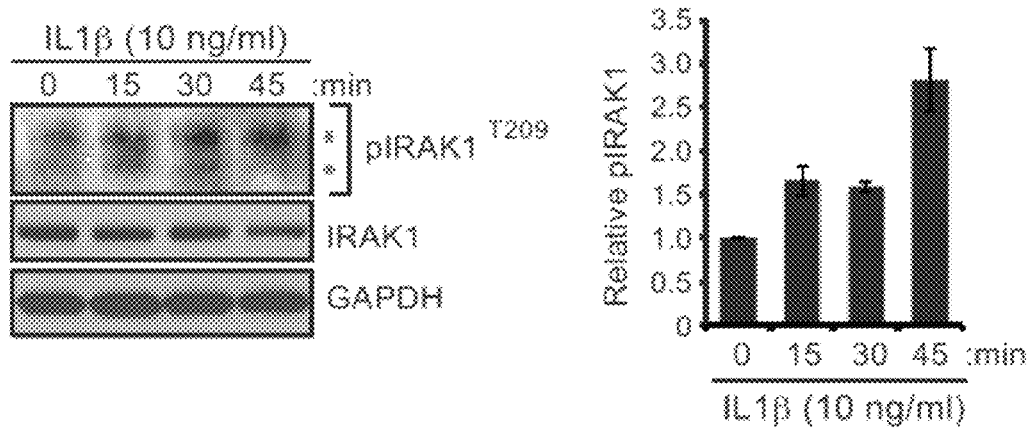

IRAK1 is activated in response to lipopolysaccharide (LPS) or interleukin-1β (IL-1β), and subsequently becomes phosphorylated (p) at threonine-209 (pIRAK1T209) (FIG. 1F, 1G) (Kollewe et al., 2004). To determine the activation status of IRAK1 in MDS, we measured pIRAK1T209 by immunoblotting marrow cells from 5 MDS patients. As shown in FIG. 1B, IRAK1 protein is not only overexpressed but also highly phosphorylated at T209. To confirm these observations, we examined normal mononuclear cells (MNC), cord blood CD34+ cells, and a panel of 6 MDS/AML-derived human cell lines. In accordance with MDS patients, IRAK1 is overexpressed and hyperphosphorylated at T209 in all the MDS/AML cell lines examined, but not in normal MNC or CD34+ cells (FIG. 1D, 1E). In contrast, phosphorylated IRAK1 is observed to a lesser extent in primary AML despite having overexpression of IRAK1 protein (FIG. 1C), suggesting that activated IRAK1 is more pronounced and specific in MDS. Phosphorylation at Serine 376 (S376), a residue not implicated in IRAK1 activation, was not phosphorylated in any of the cell lines (FIG. 1D). These findings indicate that IRAK1 is overexpressed and activated in MDS patients.

The level of IRAK1 protein expression is significantly higher relative to IRAK1 mRNA expression in MDS/AML cells, suggesting that IRAK1 is overexpressed in part through a post-transcriptional effect (FIG. 1A, 1B). Since IRAK1 is a validated target of miR-146a, a miRNA deleted and implicated in the pathogenesis of MDS (Boldin et al., 2011; Starczynowski et al., 2010; Taganov et al., 2006), we evaluated whether loss of miR-146a results in depression of IRAK1 protein in MDS cells. We designed and overexpressed a retroviral miR-146a decoy in MDSL cells, which results in ~80% downregulation of endogenous miR-146a. Knockdown of miR-146a in MDSL cells resulted in ~3-fold increase in IRAK1 and TRAF6 protein (another validated miR-146a target). Furthermore, miR-146a expression inversely correlated with total IRAK1 mRNA/protein and phosphorylated IRAK1 in MDS/AML cell lines and MDS patient cells. Although multiple mechanisms may contribute to increase IRAK1 expression and/or activation, loss of miR-146a may represent a key event in MDS resulting in constitutively active IRAK1. Notwithstanding, overexpression and activation of IRAK1 is a common feature in MDS.

IRAK-Inh Blocks TRAF6 and NF-κB Activation.

A small molecule inhibitor of IRAK1 (IRAK1/4-Inh or IRAK-Inh), which selectively inhibits its kinase activity in a low micromolar range (IC50=0.75 μM), has been initially developed for autoimmune disease (FIG. 2A) (Powers et al., 2006; Wang et al., 2009). To determine whether IRAK-Inh can effectively inhibit active IRAK1 in MDS/AML cell lines and patient cells, we treated cells with an escalating dose of IRAK-Inh (0-10 μM) for 24 hrs. pIRAK1T209 was reduced in a dose-dependent manner in MDS/AML cell lines (FIG. 2B). At 10 μM IRAK-Inh, phosphorylated IRAK1 was reduced by ~70% in cell lines and patient marrow cells (FIG. 2B-2D). Examination of kinases with structural homology to IRAK1 revealed that only IRAK1 is a target of IRAK-Inh in malignant myeloid cells. Lentiviral-mediated IRAK1 or TRAF6 overexpression resulted in increased pIRAK1T209 (without exogenous stimulation), which is also inhibited by IRAK-Inh by ~50%. Upon phosphorylation, IRAK1 simultaneously undergoes TRAF6-mediated K63-linked ubiquitination (FIG. 2A), which is another indicator of its active state (Conze et al., 2008). In the presence of IRAK-Inh, immunoprecipitated (IP) IRAK1 exhibits reduced phosphorylation and K63-linked ubiquitination (FIG. 2E).

Figure 2A:
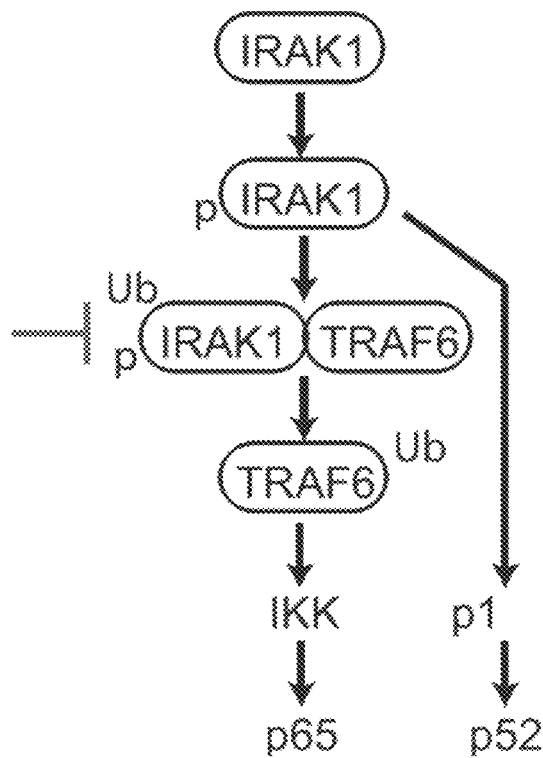
FIG. 2A-2H. IRAK-Inh suppresses TRAF6 and NF-κB activation in MDS/AML.
Figure 2B:
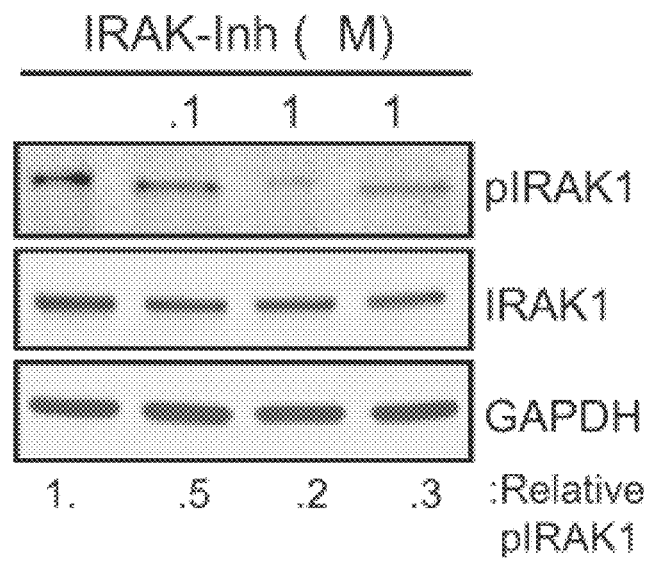
Figure 2C:
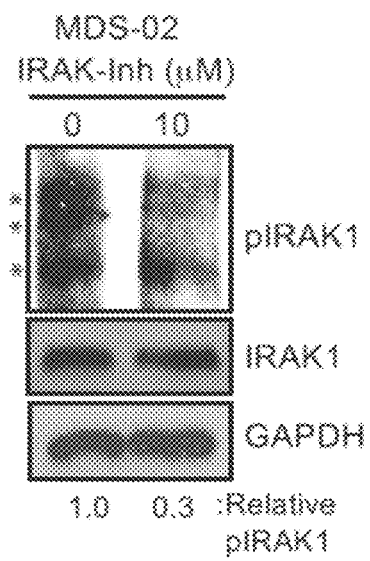
Figure 2D:
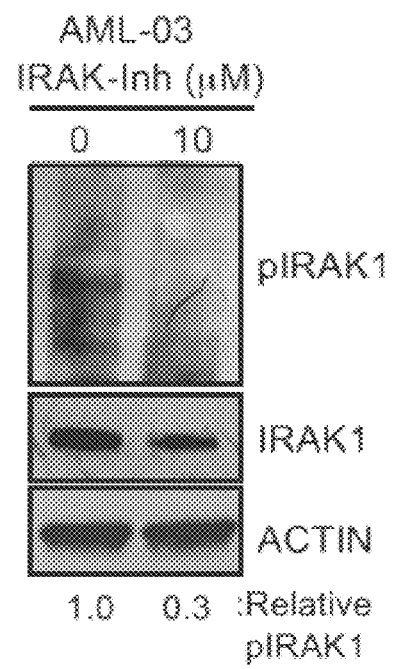
Figure 2E:
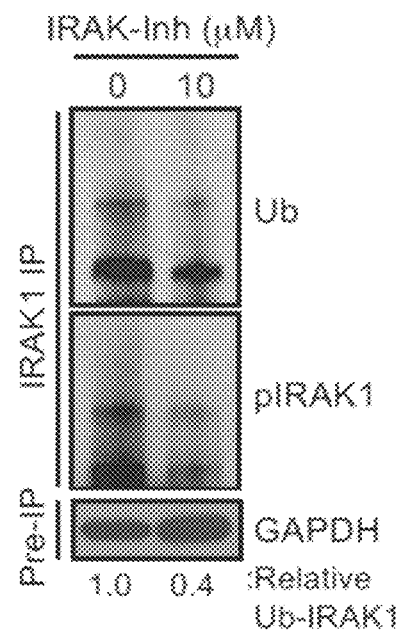
Figure 2F:
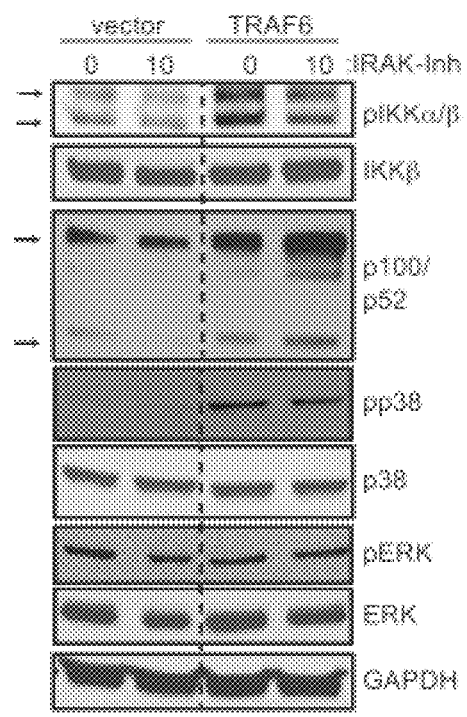
Figure 2G:
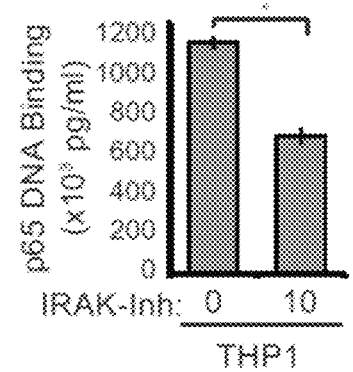
Figure 2G:
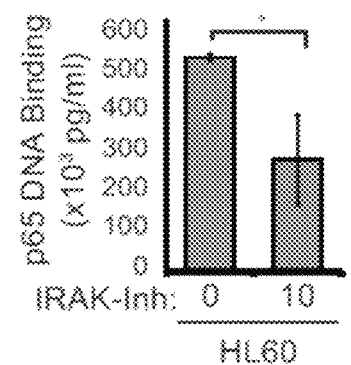
Figure 2H:
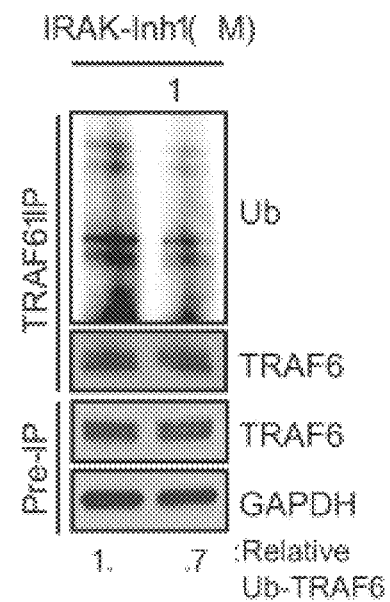

TRAF6 forms a signaling complex with pIRAK1, resulting in IKK complex activation and subsequent NF-κβ (RelA/p65) nuclear DNA-binding (FIG. 2A). As expected, TRAF6 overexpression induces phosphorylation of IKKα/IKKβ, the two catalytic proteins within the IKK complex (FIG. 2F). In the presence of IRAK-Inh (10 μM for 24 hrs), vector- and TRAF6-expressing cells exhibit reduced pIKKα/IKKβ (FIG. 2F), but not relevant MAP kinases (p38 or ERK). Inhibition of p100/p52 processing, which is a measure of non-canonical NF-κβ activation and is independent of TRAF6 (FIG. 2A), was also completely blocked by the IRAK-Inh (FIG. 2A, 2F). In addition, DNA bound and active RelA/p65 was decreased by ~50% in MDS/AML cell lines by IRAK-Inh, indicating that IRAK-Inh effectively blocks IRAK1-mediated activation of NF-κB in MDS/AML cells (FIG. 2G). Lastly, TRAF6 undergoes K63-autoubiquitination, which is a necessary step prior to NF-κB activation (FIG. 2A). Treatment with IRAK-Inh also coincides with reduced polyubiquitinated TRAF6 (FIG. 2H). Taken together, IRAK-Inh effectively blocks IRAK1 function as is evident by reduced levels of phosphorylated and K63-ubiquitnated IRAK1, reduced autoubiquitination of TRAF6, and impaired NF-κβ nuclear DNA binding (FIG. 2A).

Cytostatic Effect of IRAK-Inh on MDS Progenitor Function and Cell Growth.

Figure 3A:
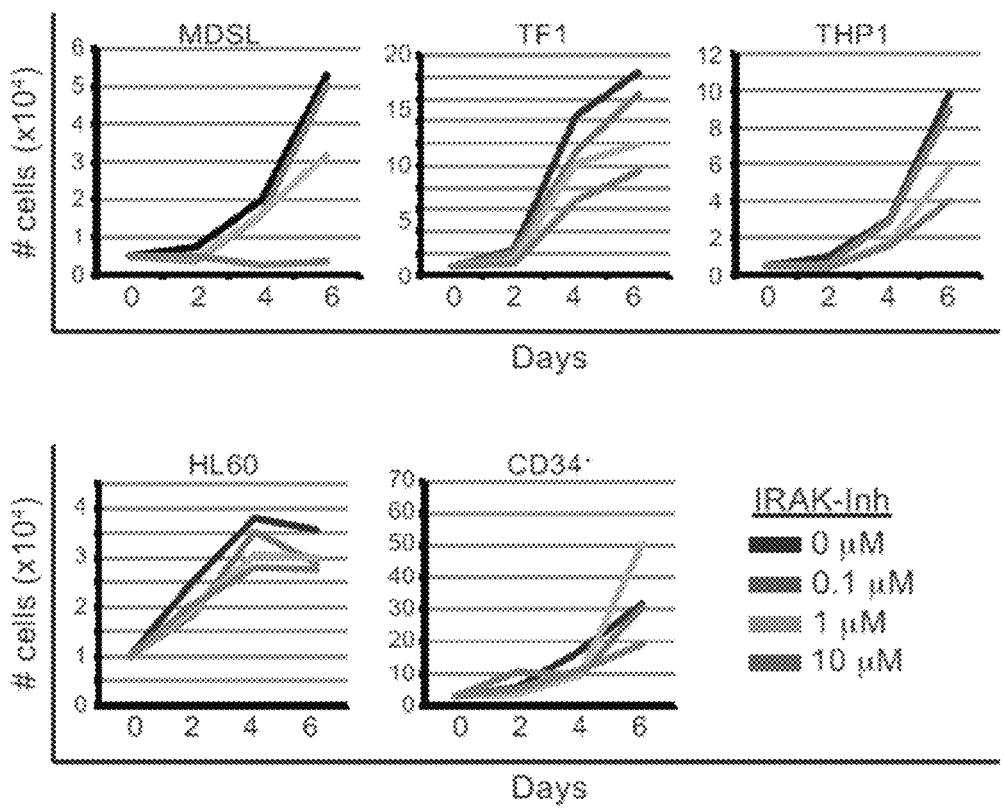
FIG. 3A-G. IRAK-Inh impairs MDS cell viability and progenitor function.
Figure 3B:
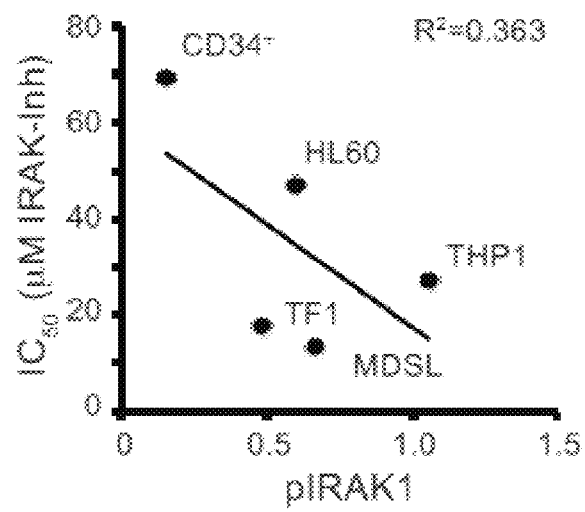
Figure 3C:
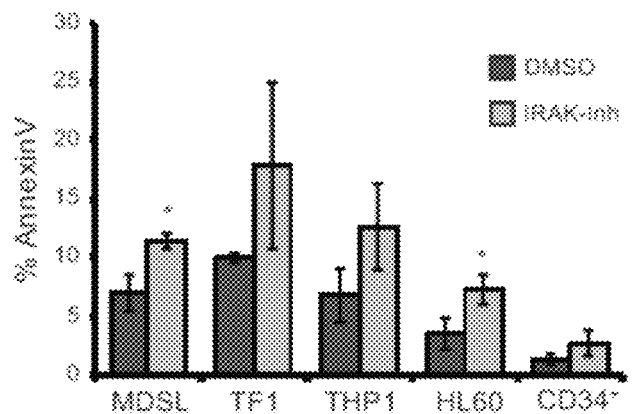
Figure 3D:
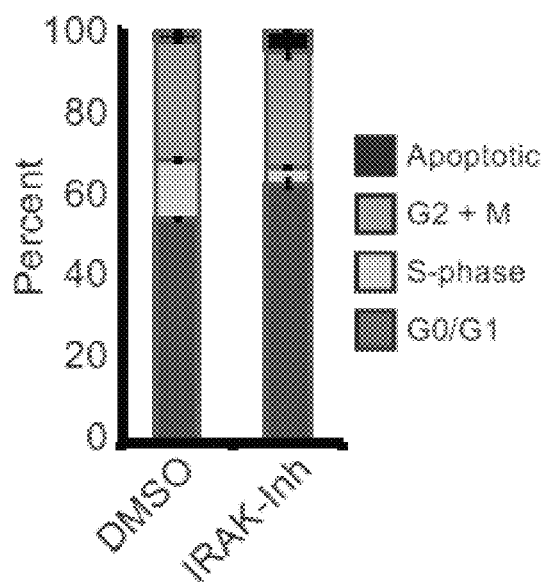

MDS/AML cell lines with hyperphosphorylated IRAK1 (FIG. 1D) were evaluated for sensitivity to IRAK-Inh. MDS/AML cell lines exposed to increasing concentration of IRAK-Inh were cultured for up to 6 days in vitro (FIG. 3A). A significant, dose-dependent impairment of MDSL, TF1, and THP1 cell proliferation was observed in the presence of IRAK-Inh (FIG. 3A). In contrast, the proliferation of normal cord blood-derived $CD34^+$ cells, which do not exhibit activation of IRAK1, was not affected with even high doses of IRAK-Inh (FIG. 3A). Despite having hyperphosphorylated IRAK1 (FIG. 1C, 1D) and exhibiting reduced pIRAK1 after IRAK-Inh treatment (FIG. 2D), the viability of HL60 cells and primary AML marrow cells was only modestly reduced with IRAK-Inh (FIG. 3A). In support of this observation, the inhibitory effect of IRAK-Inh on the cell lines correlated with the level of phosphorylated IRAK1 ($R2=0.36$; FIG. 3B). In parallel, cell viability was examined after 48 hrs of treatment with the IRAK-Inh. All cell lines exhibited a modest increase in apoptosis (FIG. 3C). To investigate whether IRAK-Inh affects cell cycle progression, MDSL cells were treated with 10 μM IRAK-Inh for up to 6 days and evaluated by BrdU/7AAD staining (FIG. 3D). Consistent with reduced proliferation (FIG. 3A), MDSL cells treated with IRAK-Inh have altered cell cycle kinetics: there are fewer viable MDSL cells in S phase (4.3%±0.4 versus 14.2%±0.2; p=0.0002) and increased proportion in G0/G1 (62.7%±1.1 versus 54.5%±0.7; p=0.008) (FIG. 3D). In addition, the proportion of sub-G0 cells was significantly increased in IRAK-Inh-treated cells (5.4%±0.3 versus 1.8%±0.2; p=0.003).

Figure 3E:
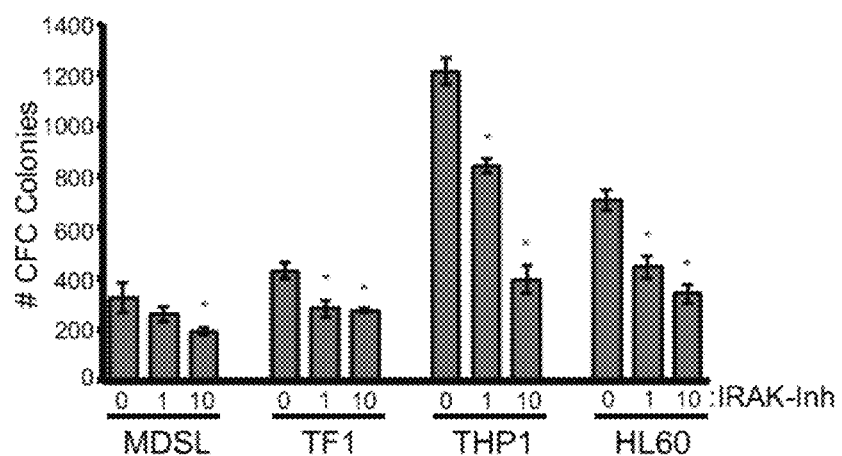

The effect of IRAK-Inh on leukemic progenitor function was evaluated in methylcellulose containing IRAK-Inh. Normal $CD34^+$ formed equivalent number of colonies with moderate skewing of erythroid and granulocytic/macrocytic progenitors (p<0.05) when treated with IRAK-Inh. In stark contrast, all MDS/AML cells formed significantly fewer colonies when treated with IRAK-Inh (FIG. 3E). As an alternative approach, MDS/AML cells were pre-treated with IRAK-Inh for 24 hours and then plated in methylcellulose. After transient exposure (24 hr) to IRAK-Inh (10 μM), MDS/AML cells, but not normal $CD34^+$, formed significantly fewer colonies, suggesting that IRAK-Inh suppresses the function of the disease-propagating cell. Increased apoptosis, impaired cell cycle progression, and reduced progenitor function after IRAK-Inh treatment is not a consequence of induced differentiation, as IRAK Inh-treated MDS/AML cells did not undergo noticeable myeloid differentiation in vitro. To determine whether the effects of IRAK-Inh can be rescued by activating the innate immune pathway downstream of IRAK1 (FIG. 2A), we overexpressed TRAF6 and then measured the cellular toxicity of IRAK-Inh. Although IRAK-Inh partially suppresses NF-κβ in TRAF6-overexpressing cells (FIG. 2F), forced expression of TRAF6 in MDSL cells can overcome the inhibitory effects of IRAK-Inh and restore cell viability and progenitor function in IRAK Inh-treated cells. Collectively, these results suggest that IRAK-Inh is effective in selectively inhibiting the viability and function of MDS progenitor cells while sparing normal $CD34^+$ cells by directly targeting the innate immune pathway.

Figure 3F:
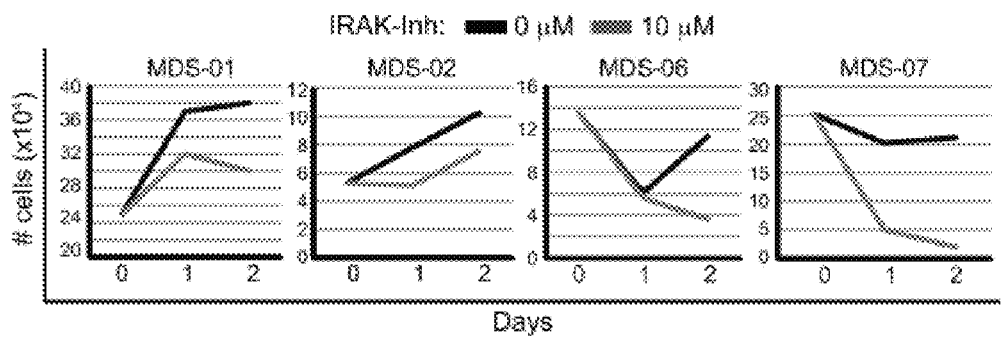
Figure 3G:
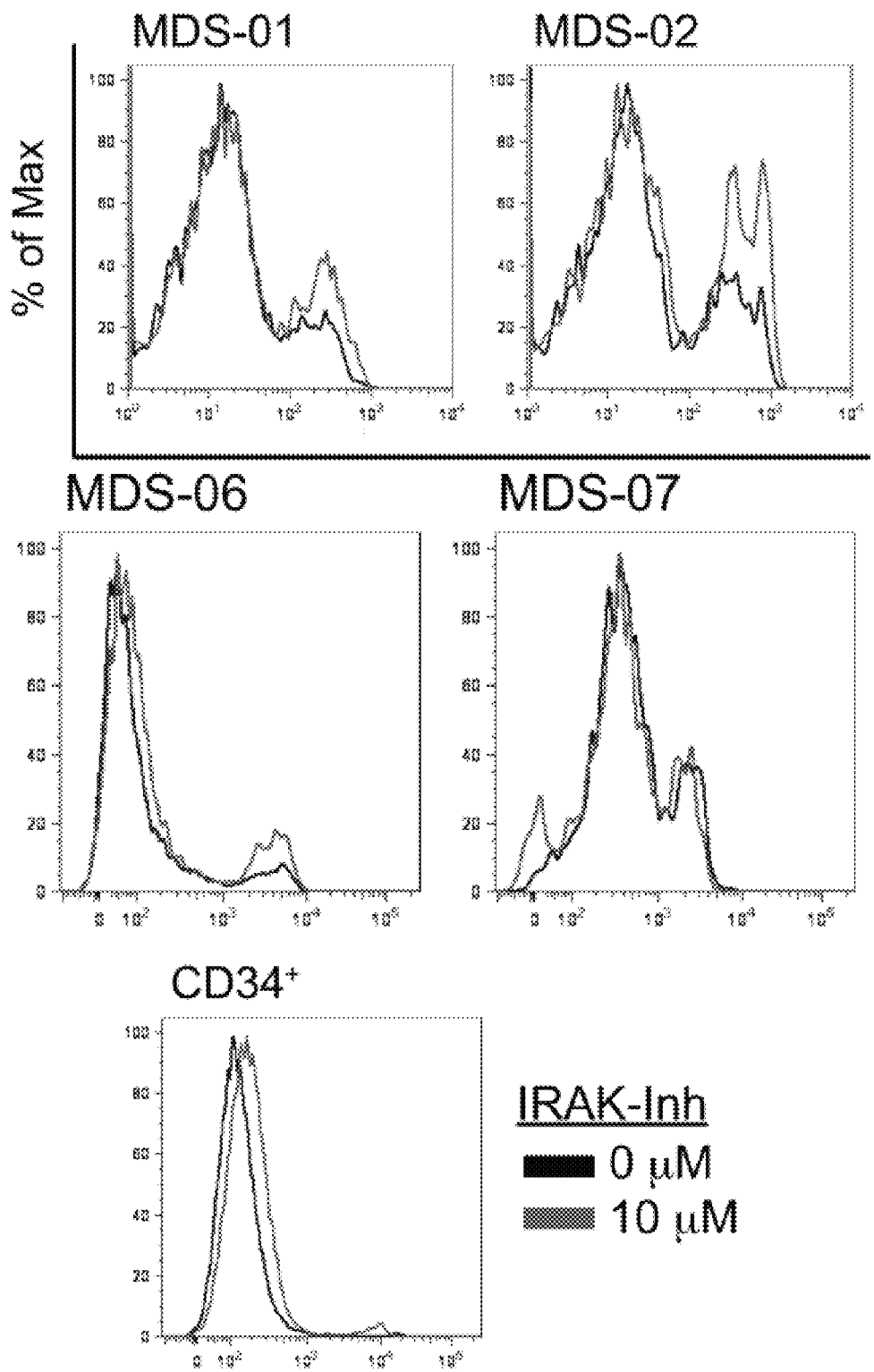
Figure 3H:
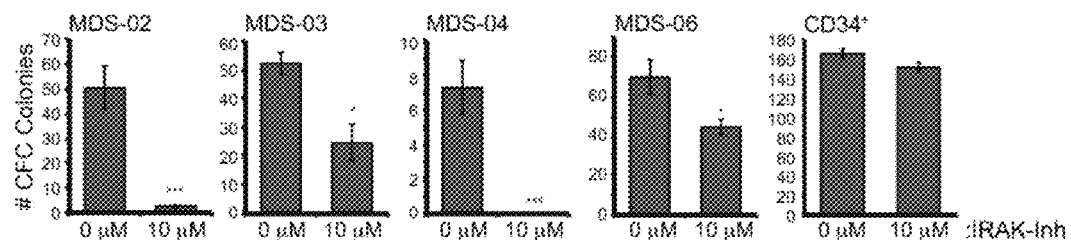
(FIG. 3H) Marrow cells from MDS patients were evaluated for colony formation in methylcellulose containing IRAK-Inh. *, $p<0.05$; , $p<0.01$; *, $p<0.001$. Error bars represent ±SD.

We evaluated marrow cells from 7 MDS and 3 AML patient samples with various cytogenetic features to determine whether IRAK1 inhibition is also effective in primary patient cells (Table S1). MDS marrow cells treated with IRAK-Inh for 48 hrs failed to expand (FIG. 3F) and exhibited increased levels of apoptotic cells, except for MDS-07 (FIG. 3G). In contrast, vehicle control-treated MDS cells expanded nearly 2-fold during this time and had significantly fewer apoptotic cells (FIG. 3F, 3G). AML marrow cells treated with IRAK-Inh continued to grow similar to control-treated cells. Since MDS and AML stem/progenitor cells are clonal and the disease-propagating cells form colonies in methylcellulose, we also evaluated the effects of IRAK-Inh on colony formation. Whether continuously treated (FIG. 3H) or briefly exposed to IRAK-Inh, MDS marrow cells formed significantly fewer colonies in the presence of IRAK-Inh. In contrast, IRAK-Inh did not affect AML or control CD34+ cell progenitor function (FIG. 2H). These findings indicate that IRAK-Inh selectively inhibits growth and progenitor function of primary MDS marrow cells, and that IRAK-Inh sensitivity is a general feature of MDS, independent of existing genetic features.

IRAK-Inh Ameliorates Disease in a Human Xenograft Model Using an MDS-Derived Cell Line.

Primary MDS patient samples remain difficult to engraft into immunodeficient mice, typically with less than 5% marrow engraftment and no evidence of disease (Martin et al., 2011; Park et al., 2011). To circumvent this limitation, we developed a xenograft model using an MDS patient-derived cell line (MDSL), which has retained phenotypic and cellular characteristics of MDS (Matsuoka et al., 2010; Tohyama et al., 1995). Consistent with non-transforming MDS subtypes, the MDSL cell line does not form overt leukemia in NSGS or NSG mice. Instead, MDSL cells engraft into the marrow and gradually expand over time within the marrow, spleen, and peripheral blood as a non-blast/incompletely differentiating myeloid population. Xenografted mice develop progressive anemia, thrombocytopenia, and extramedullary hematopoiesis and eventually succumb to disease. Disease progression and MDSL expansion in the marrow is accompanied by depletion of normal mouse hematopoietic cells and a hypocellular marrow.

Figure 4A:
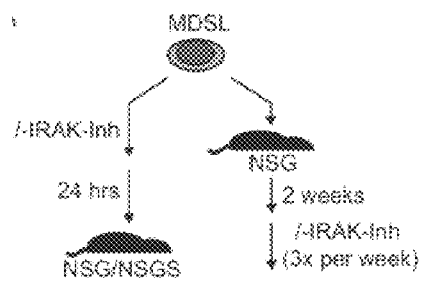
FIG. 4A-H. IRAK-Inh suppresses MDS xenografts.
Figure 4B:
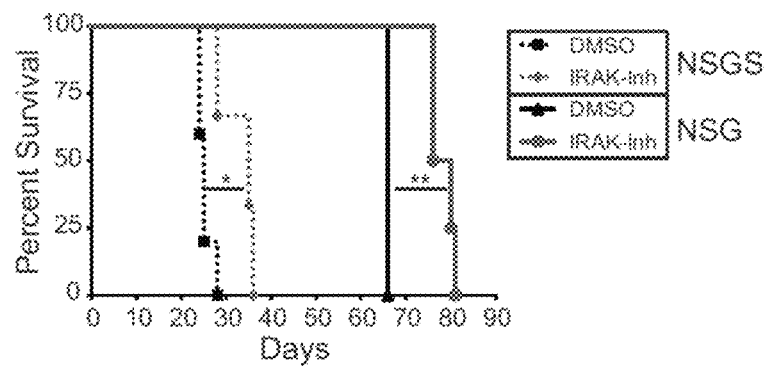
Figure 4C:
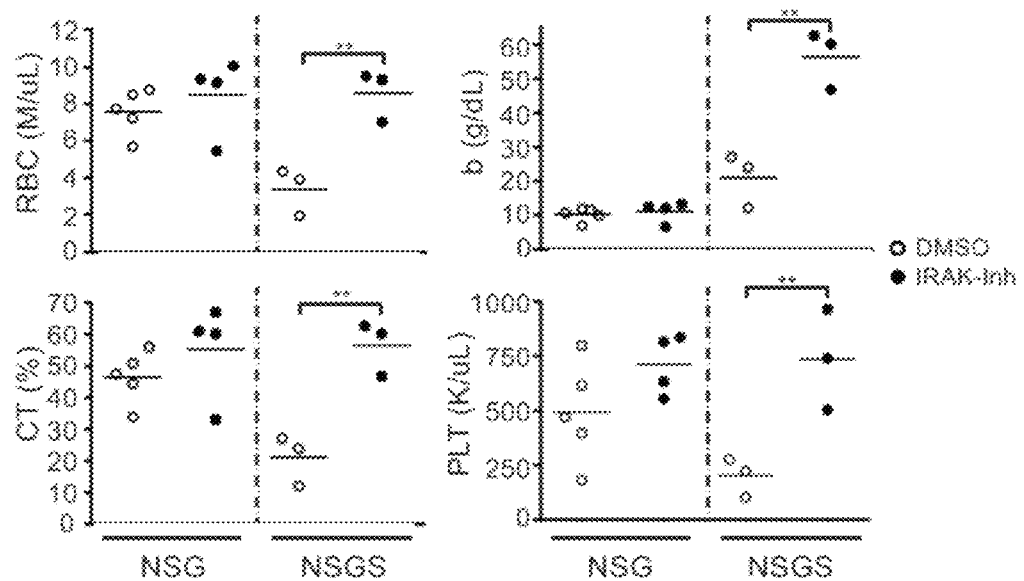
Figure 4D:
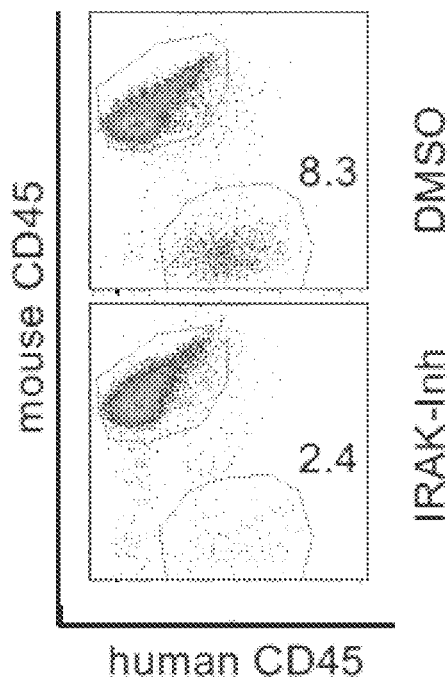
Figure 4E:
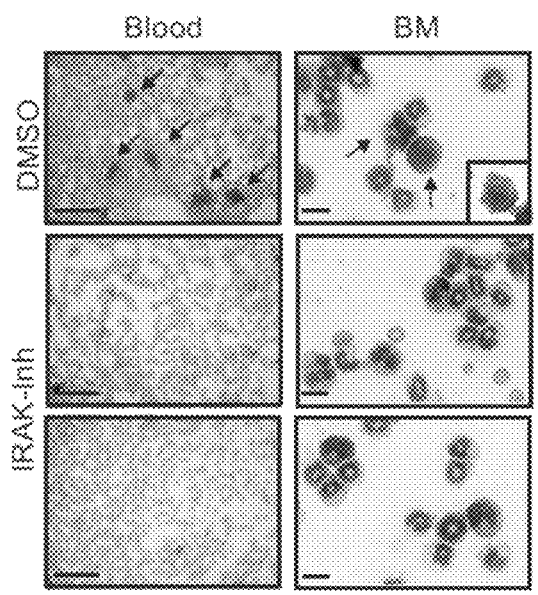
Figure 4F:
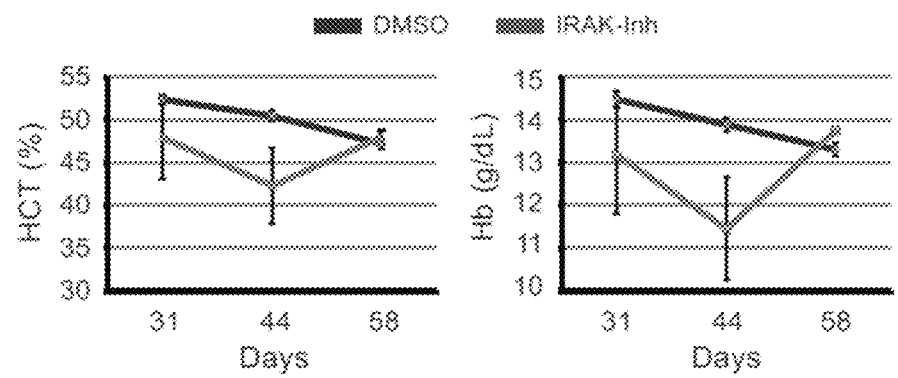
Figure 4G:
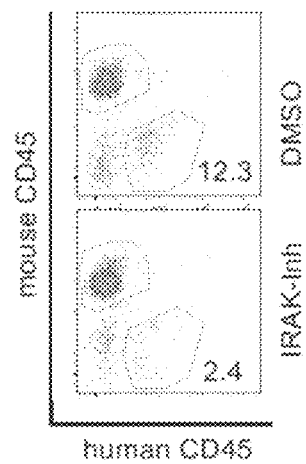
Figure 4H:
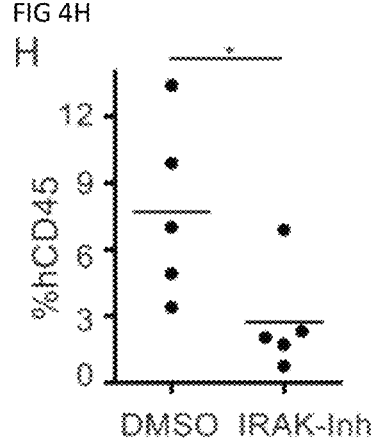

To determine whether IRAK-Inh can delay human MDS-like disease in vivo, MDSL were pre-treated with IRAK-Inh (10 μM) for 24 hrs in vitro and subsequently injected intravenously (i.v.) into NSG ($5 \times 10^6$ cells) and NSGS ($1 \times 10^6$ cells) recipient mice (FIG. 4A). This approach permitted us to evaluate the cell autonomous effect of IRAK-Inh on MDS cell viability and engraftment without altering endogenous IRAK1 function in the mouse. As shown in FIG. 4B, pretreatment with IRAK-Inh significantly delayed the MDS-like disease in NSG mice (median survival=80 days vs 68 days; p=0.0065) and in NSGS mice (median survival=38 days vs 29 days; p=0.028). NSGS mice transplanted with IRAK-Inh-treated MDSL cells also had significantly improved red blood cell numbers (p=0.0085), hemoglobin (p=0.012), hematocrit (p=0.015) and platelets (p=0.02) (FIG. 4C). In addition, the human MDSL graft was reduced from 8% to 2% (FIG. 4D). Morphological assessment confirmed normal RBC and reduced MDS grafts in the peripheral blood and marrow of mice transplanted with IRAK-Inh-treated MDSL cells (FIG. 4E). To demonstrate that the IRAK-Inh can also ameliorate disease after cells have engrafted, MDSL were injected i.v. into NSG mice, followed by intraperitoneal (i.p.) injection of IRAK-Inh (FIG. 4A). Mice receiving IRAK-Inh maintained HCT and Hb levels while control mice exhibited a progressive anemia (FIG. 4F). Within ~7 days of receiving IRAK-Inh, mice had reduced human graft in the peripheral blood (FIG. 4G, 4H). These findings indicate that IRAK-Inh targets the disease-propagating cell and provides a significant survival benefit in a xenograft model of human MDS.

Knockdown of IRAK1 Protein Induces Apoptosis and Impaired Clonal-Progenitor Function.

Figure 5A:
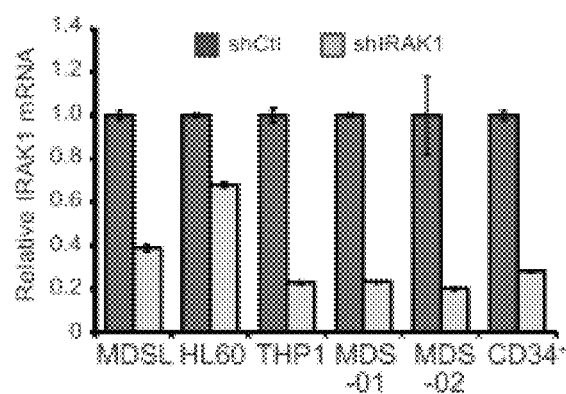
FIG. 5A-I. IRAK1 is essential for MDS progenitor cell survival.
Figure 5B:
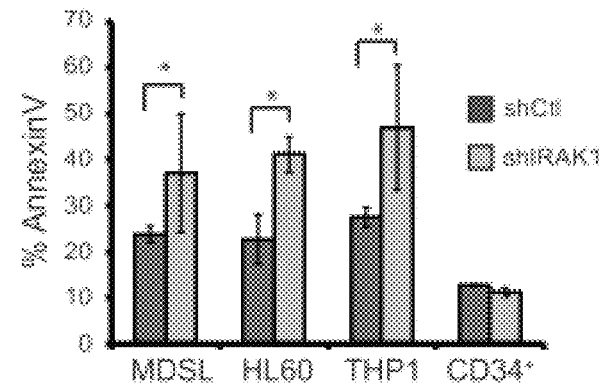
Figure 5C:
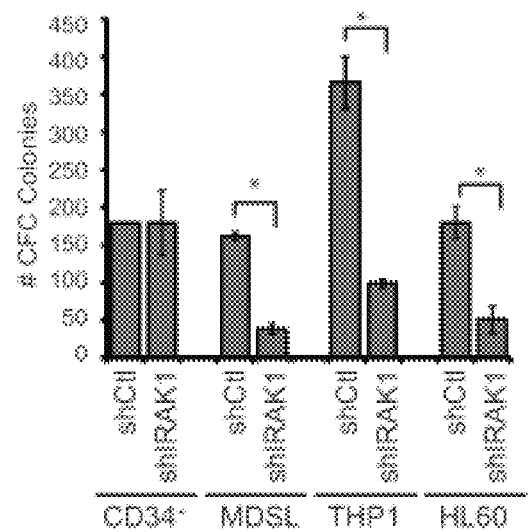
Figure 5D:
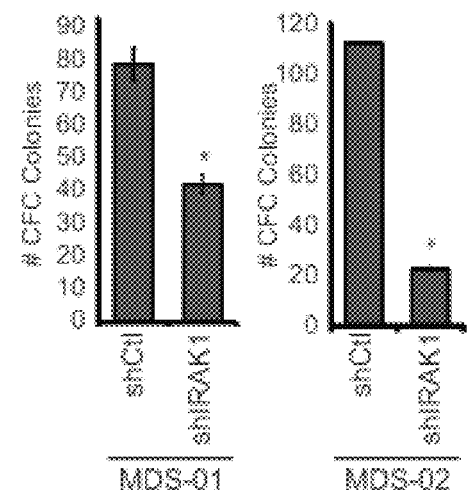
Figure 5E:
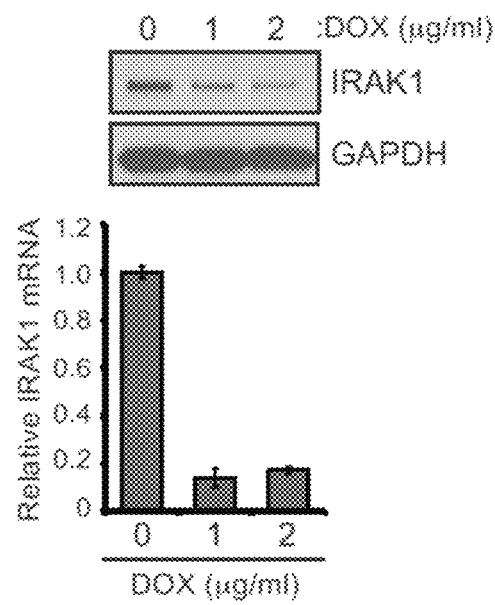
Figure 5F:
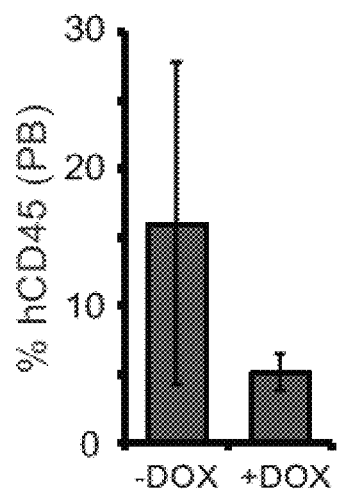
Figure 5G:
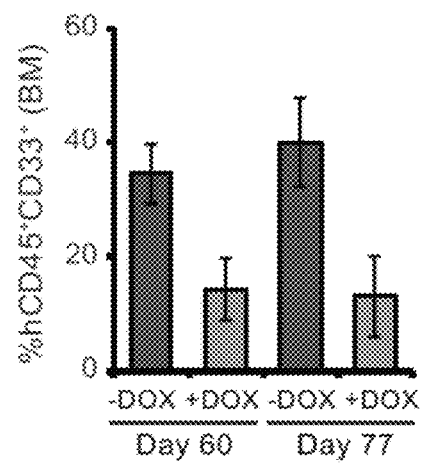
Figure 5H:
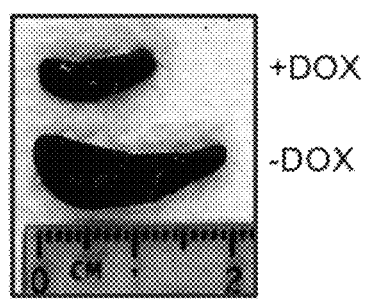
Figure 5I:
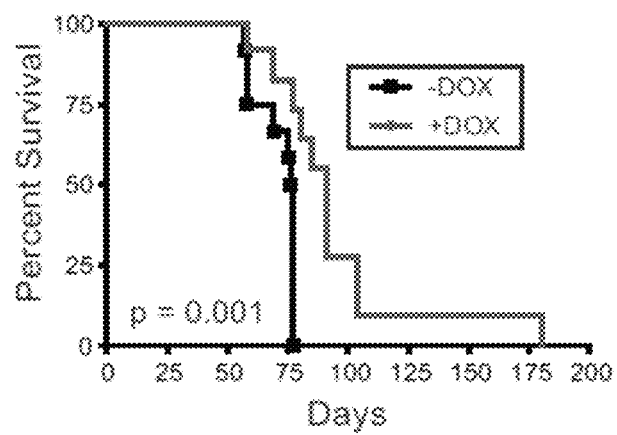

To validate the effects and specificity of the IRAK-Inh, lentiviral vectors encoding independent short hairpin RNAs (shRNA) targeting IRAK1 were transduced into MDS/AML cell lines and MDS patient marrow cells. We confirmed targeting of IRAK1 by immunoblotting and quantitative RT-PCR (qRT-PCR) (FIG. 5A). Although IRAK-Inh induced only a modest apoptotic affect (FIG. 3B), all MDS/AML cell lines with depletion of IRAK1 correlated with a significant increase in apoptosis (FIG. 5B). Knockdown of IRAK1 in CD34$^+$ cells did not induce apoptosis, indicating that IRAK1 is dispensable for normal CD34$^+$ viability (FIG. 5B). MDS/AML cell lines and MDS patient samples with knockdown of IRAK1 also exhibited a significant decrease in progenitor colonies in methylcellulose (FIG. 5C, 5D). Normal CD34$^+$ were not sensitive to loss of IRAK1 and formed colonies at the same level to control-transduced CD34$^+$ cells (FIG. 5C). To examine the effects of IRAK1 depletion in vivo, MDSL cells were transduced with a doxycycline (DOX)-inducible shIRAK1 (pTRIPZ). Increasing amounts of DOX in vitro demonstrated a dose-dependent deletion of IRAK1 mRNA and protein, as well as reduced cell viability (FIG. 5E). The effects of IRAK1 knockdown were rescued by expressing a hairpin-resistant IRAK1 cDNA. Transduced MDSL cells were injected into NSG mice, and six days post-transplant, mice were given chow with or without DOX. Expression of the shRNA is observed in the marrow, spleen, and blood of DOX-treated mice, but not expressed in control mice. Without IRAK1 knockdown (minus DOX or non-transduced parental MDSL cells), mice developed the MDS-like disease (FIG. 5F-5I). In contrast, IRAK1 knockdown (plus DOX) reduced engraftment of MDS cells (PB: ~15% versus 5% [FIG. 5F]; BM: ~40% vs 10% [FIG. 6G]) and spleen size (FIG. 5H), and significantly delayed mortality in mice (p=0.001; FIG. 5I). Collectively these data suggest that genetic depletion of IRAK1 results in reduced viability and growth of MDS/AML progenitor cells in vitro and in vivo. In addition, a more profound effect on MDS/AML survival and progenitor function was observed following depletion of IRAK1 as compared to the IRAK-Inh.

Expression Profiling Following Deletion or Inhibition of IRAK1 Reveals Overlapping Gene Signatures and a Compensatory Increase in BCL2

We performed a gene expression analysis to (1) gain insight into the molecular consequences of inhibiting IRAK1 in MDS cells, and (2) define an underlying mechanism for the discrepancy between IRAK-Inh and shIRAK1 apoptotic threshold in MDS/AML cells. MDSL cells were either transduced with shIRAK1 (or control) or treated with IRAK-Inh (or DMSO) for 48 hours, followed by RNA collection for a microarray analysis (FIG. 6A). At this time point, we observe >50% knockdown of IRAK1 mRNA by the shRNA and minimal effect on cell viability. Inhibition of IRAK1 by either approach in MDSL resulted in ~180 differentially expressed genes (FIG. 6A). We searched for previously defined expression signatures that overlap genes regulated by both IRAK-Inh and shIRAK1 by using gene set enrichment analysis (GSEA) (Subramanian et al., 2005) (FIG. 6A). Of the top 10 significant GSEA sets in each group, 3 gene sets were identical between IRAK-Inh and shIRAK1 MDSL cells (FIG. 6B), indicating that IRAK1 is effectively targeted by both approaches and that inhibition by either approach induced a similar transcriptional response. Of the top GSEA sets, survival (IL6_Starve_Up) and cell cycle/proliferation (Cell_Cycle, and MM_CD138_PR_vs_REST) were the most significant in both IRAK-Inh and shIRAK1 experimental groups (FIG. 6B). To better understand the cellular and molecular consequences following IRAK1 inhibition/deletion, we examined the Gene Ontology categories using ToppGene (Chen et al., 2009). Knockdown of IRAK1 resulted in down regulation of genes involved in chromatic assembly, DNA binding, and RNA metabolism (FIG. 6C). IRAK-Inh treatment resulted in downregulation of genes involved in cell migration and adhesion, inflammatory response, and cytokine-mediated signaling (FIG. 6C).

Figure 6D:
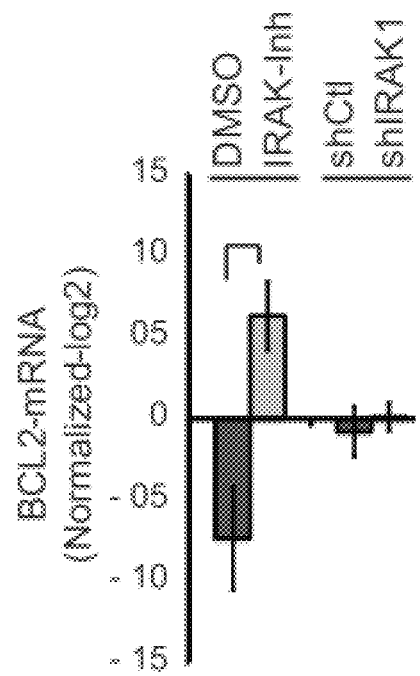
Figure 6E:
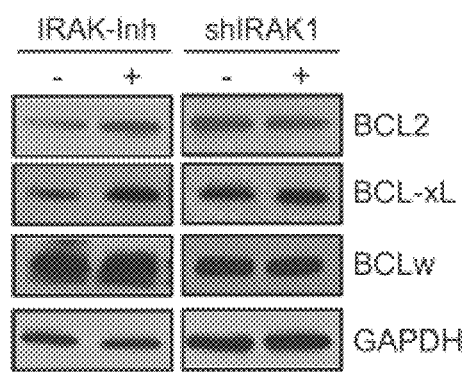
Figure 6F:
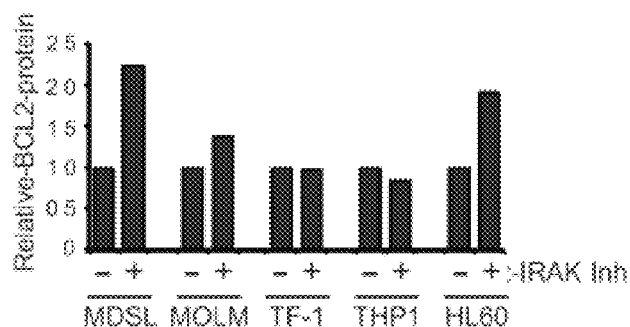

Despite the overlap in gene sets, we examined genes that could explain the discrepancy between IRAK-Inh and shIRAK1 in inducing apoptosis of MDS/AML cells. Although IRAK-Inh upregulated pro-apoptotic genes (e.g., BIM, CASP10, RIPK1), downregulation of anti-apoptotic Bcl2-family genes was not evident. As an example, BCL2 mRNA and protein was not downregulated in IRAK-Inh-treated cells; surprisingly, BCL2 expression was increased in several of the cell lines examined, an effect not observed in shIRAK1-expressing cells (FIG. 6D-6F). This observation prompted us to speculate that a subset of MDS/AML progenitors escape IRAK-Inh induced apoptosis because of a compensatory upregulation or inefficient downregulation of BCL2.

Combined Inhibition of IRAK1 and BCL2 Cooperates to Target MDS Clonal-Progenitor Function.

Figure 7A:
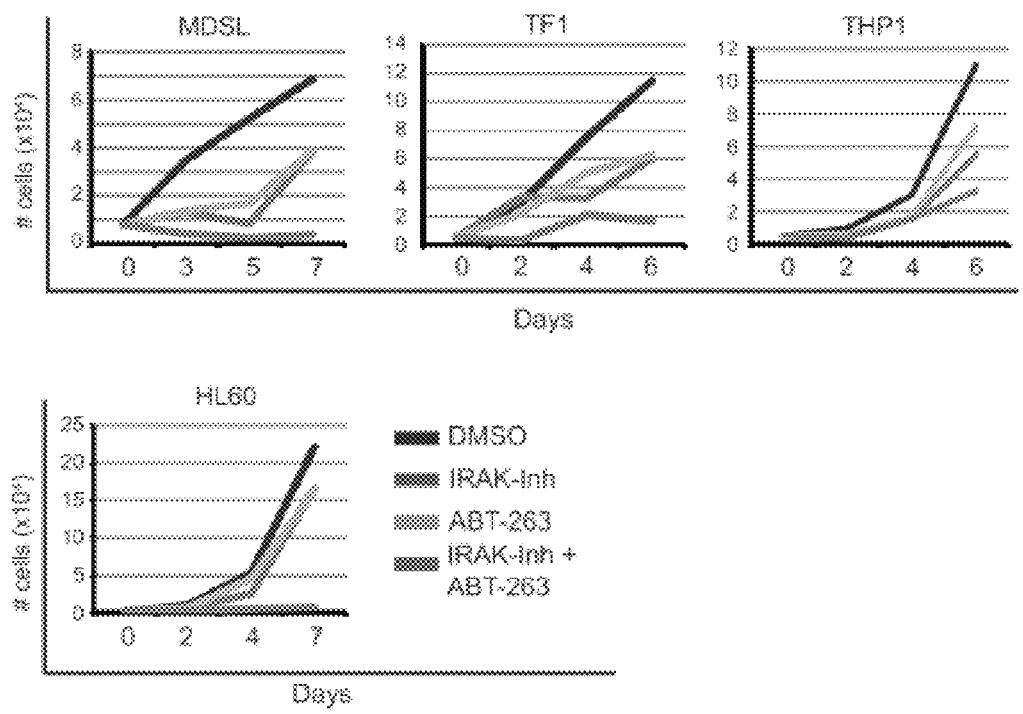
FIG. 7A-G. Combined IRAK1 and Bcl-2 inhibition provides a collaborative cytotoxic effect against MDS and AML cells.
Figure 7B:
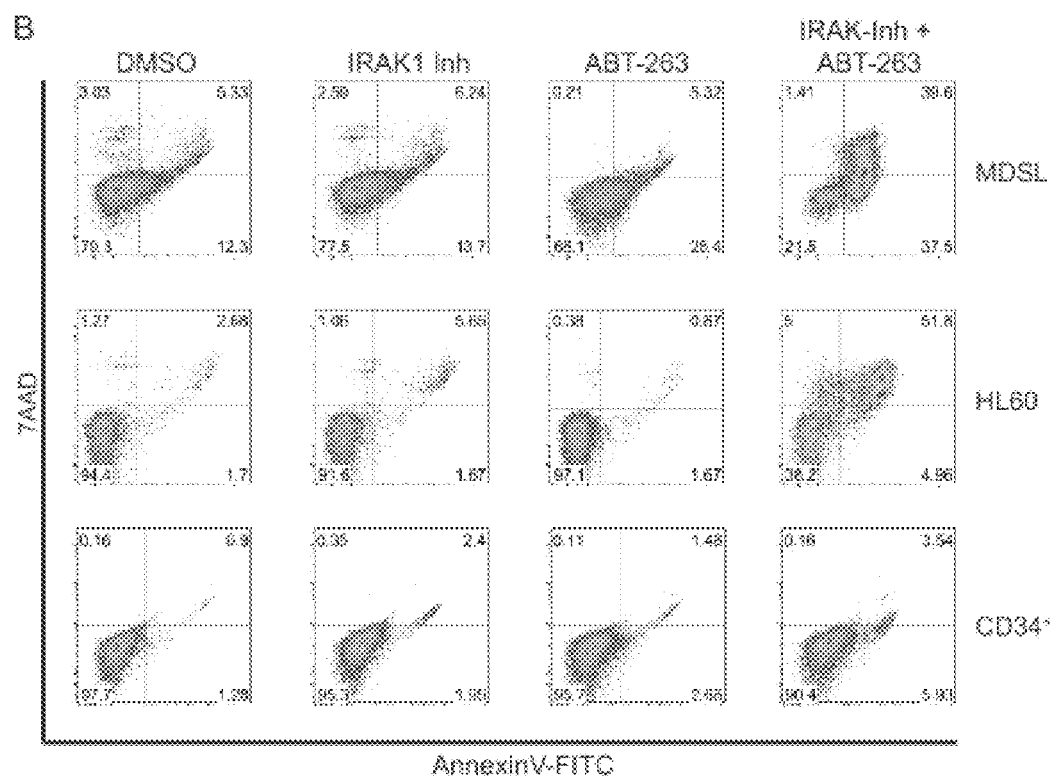
Figure 7C:
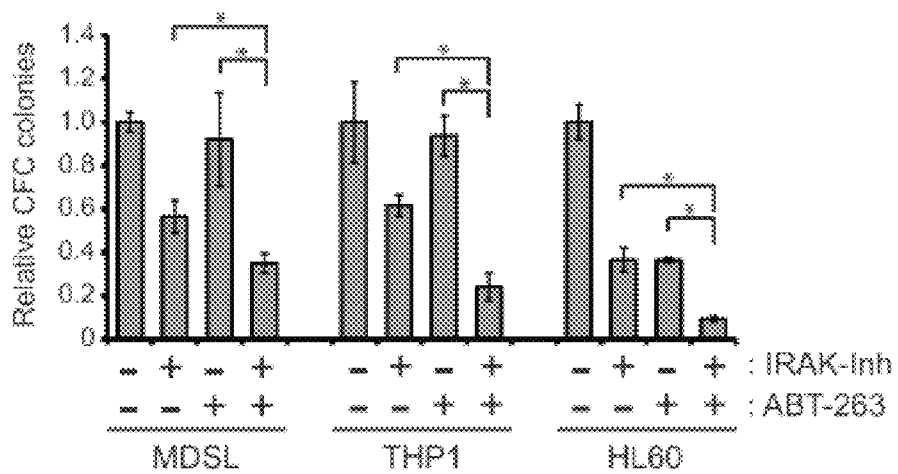
Figure 7D:
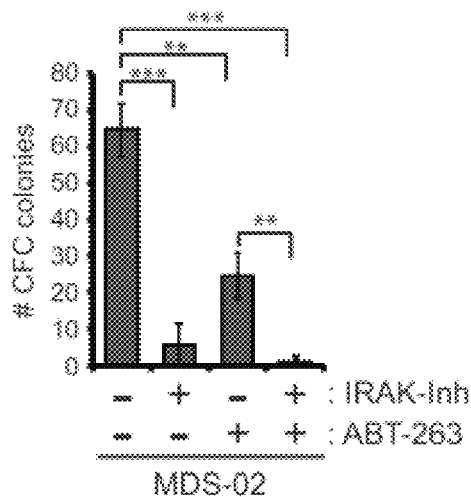
Figure 7E:
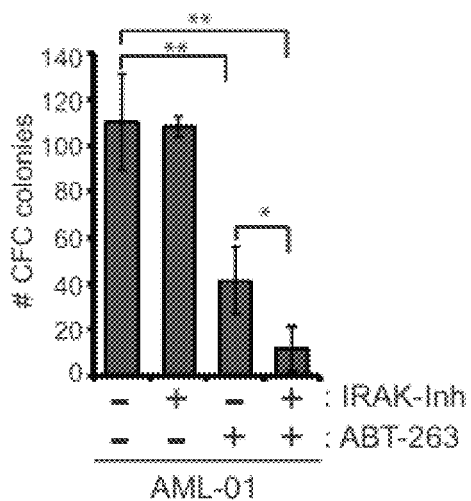
Figure 7F:
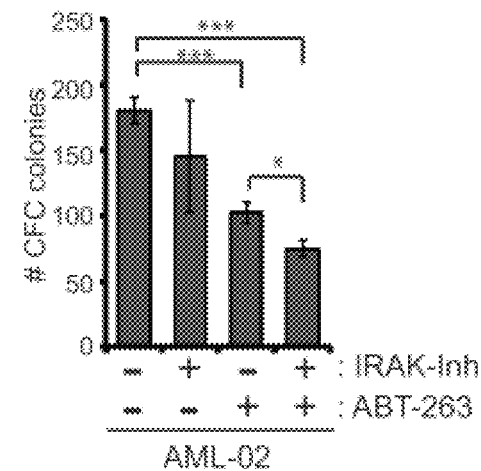

We examined the survival dependence on BCL2 function in IRAK-Inh-treated cells by utilizing a BH3-mimetic (ABT-263, Abbott Laboratories). Administration of IRAK-Inh (10 μM) or ABT-263 (0.1 μM) alone had modest effects in inhibiting MDS/AML cell line growth and survival (FIG. 7A, 7B). Strikingly, co-treatment of the MDS/AML cells with IRAK-Inh and ABT-263 significantly and synergistically inhibited cell growth and survival (FIG. 7A, 7B). In particular, HL60 cells, which were refractory to the inhibitory effects of IRAK-Inh or ABT-263 alone, are extremely sensitive to the combined treatment with ABT-263 (FIG. 7A, 7B). In addition, MDS/AML cell lines and MDS patient progenitor colonies were significantly impaired with the combination treatment of IRAK-Inh and ABT-263 (FIG. 7C, 7D). For AML patient cells that are not sensitive to IRAK-Inh treatment alone, co-treatment with ABT-263 also resulted in reduced leukemic progenitor function (FIG. 7E, 7F). The viability and hematopoietic progenitor function in methylcellulose of normal CD34+ cells was not affected by the individual or combination treatment of IRAK-Inh and ABT-263.

Figure 7G:
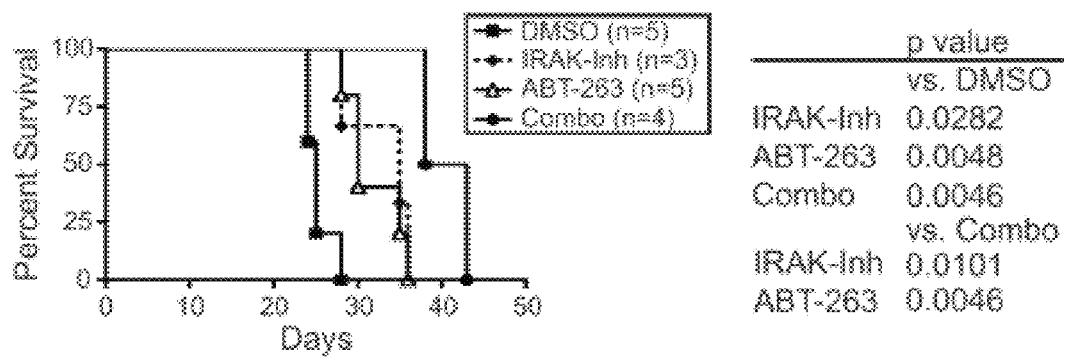
Figure 8A:
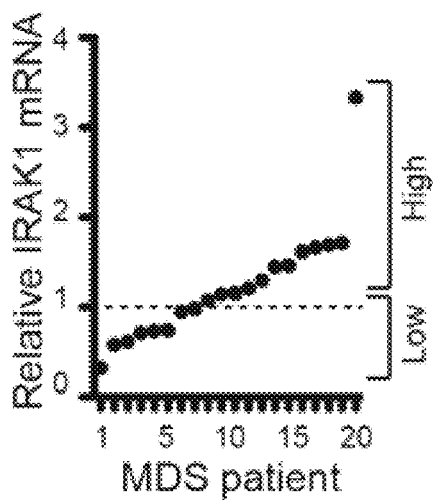
Figure 8B:
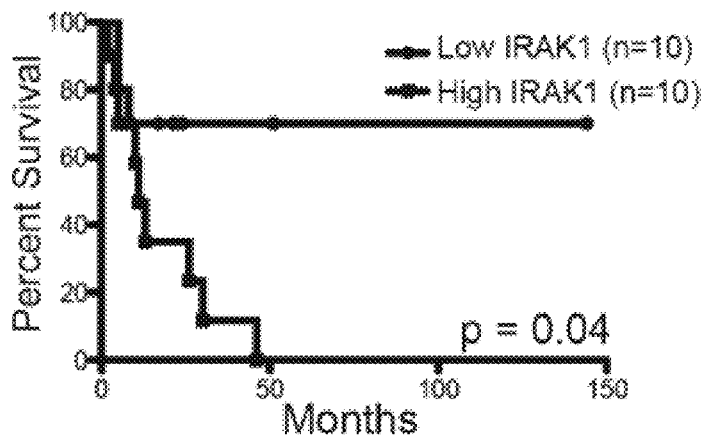
Figure 8D:
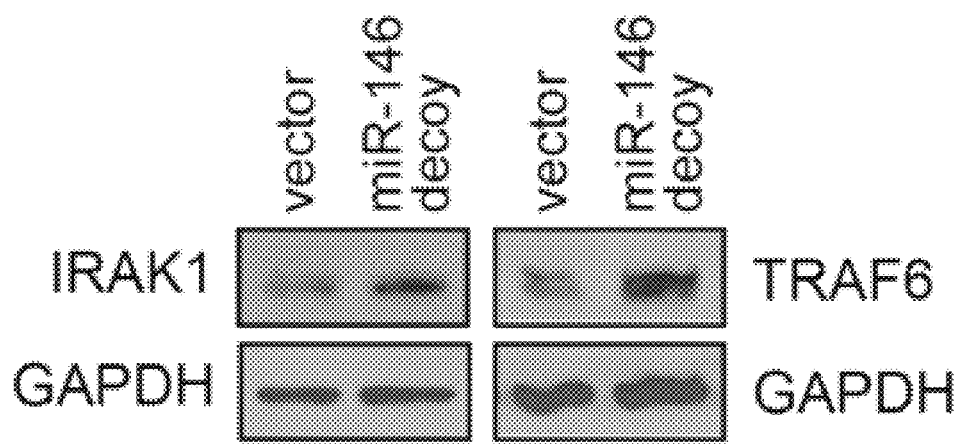
Figure 8E:
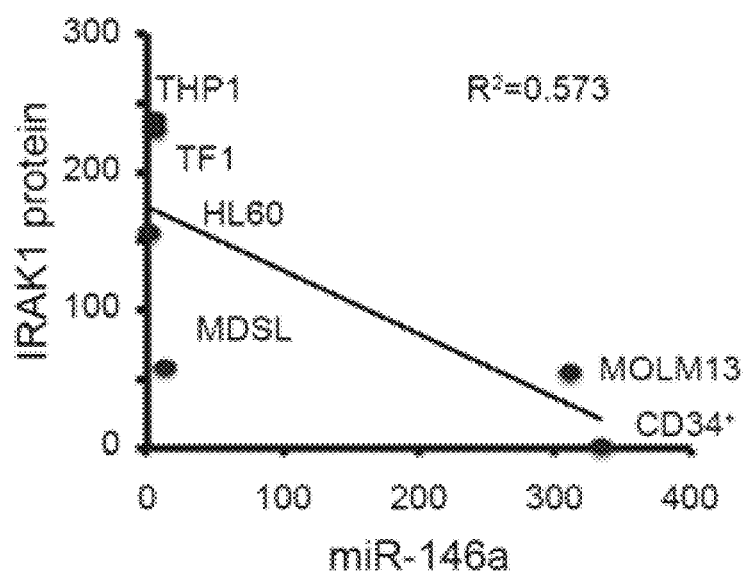
Figure 8F:
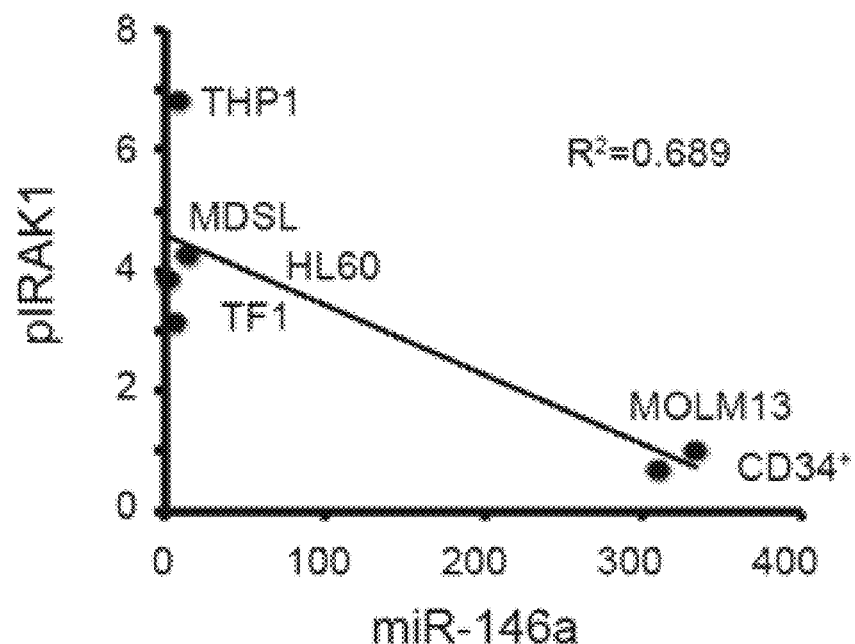
Figure 8G:
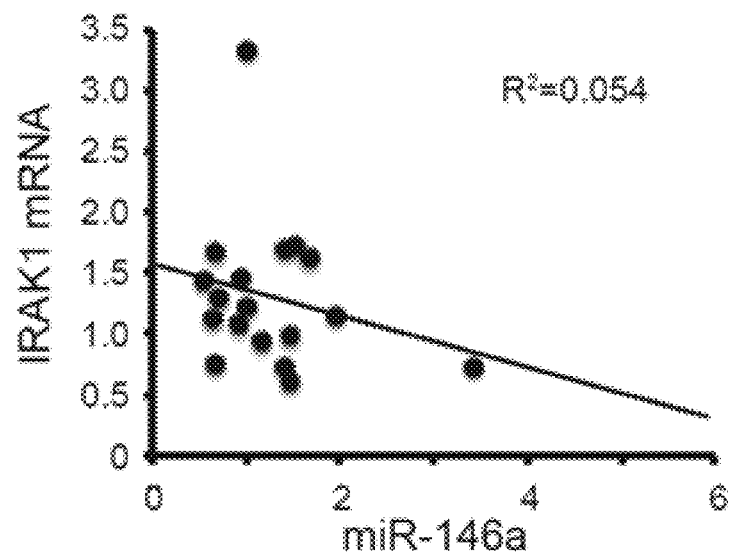
Figure 9A:
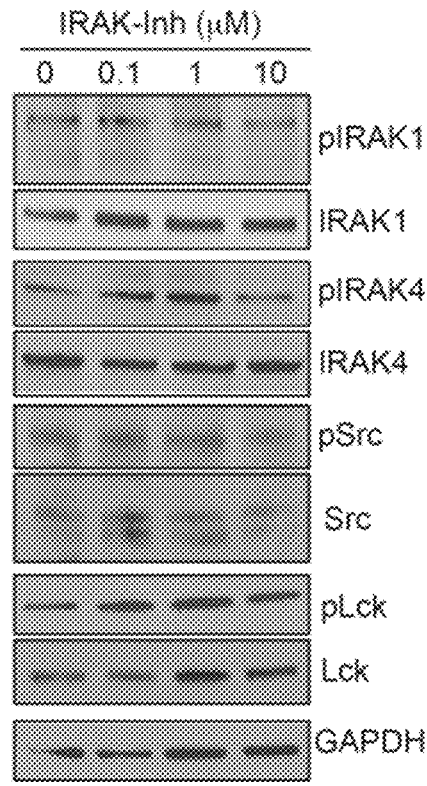
FIG. 9A-C. IRAK-Inh selectively targets IRAK1 in MDS/AML cells and its effects are partially rescued by overexpression of TRAF6.
Figure 9B:
Figure 9B:
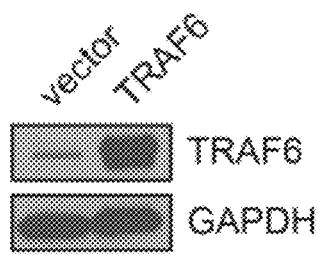
Figure 9C:
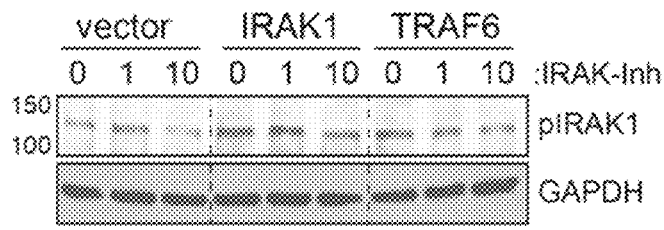
Figure 10A:
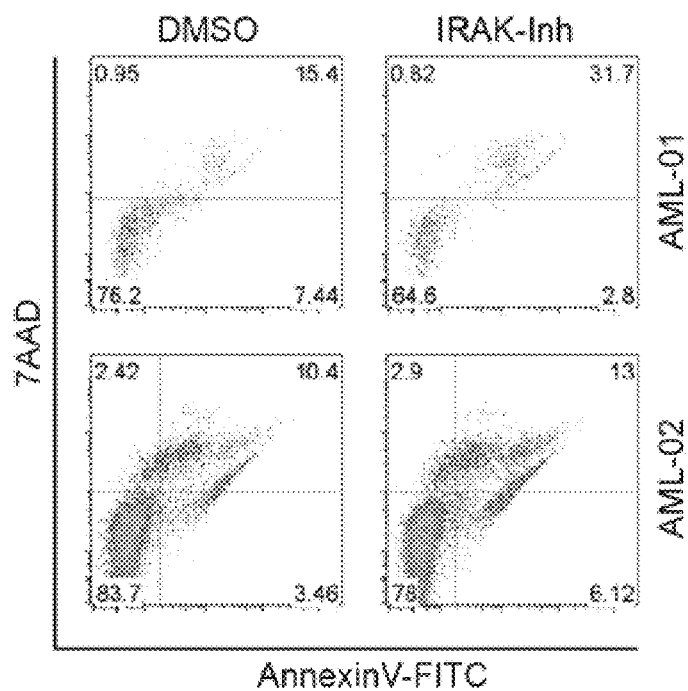
FIG. 10A-K. Effects of IRAK-Inh on primary AML and normal CD34* cells.
Figure 10B:
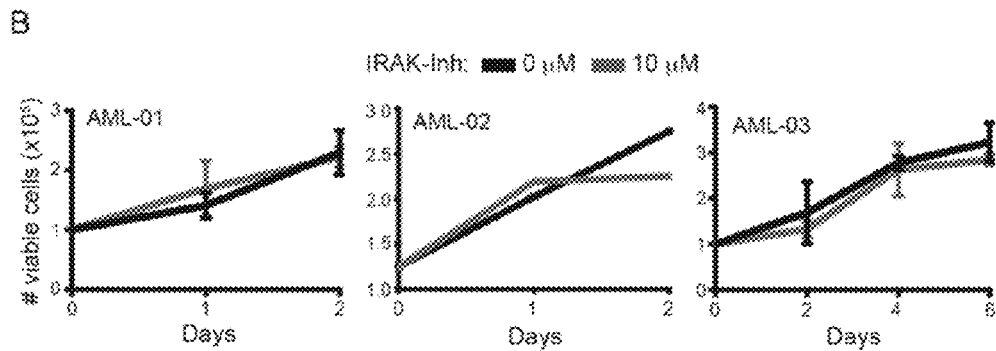
Figure 10C:
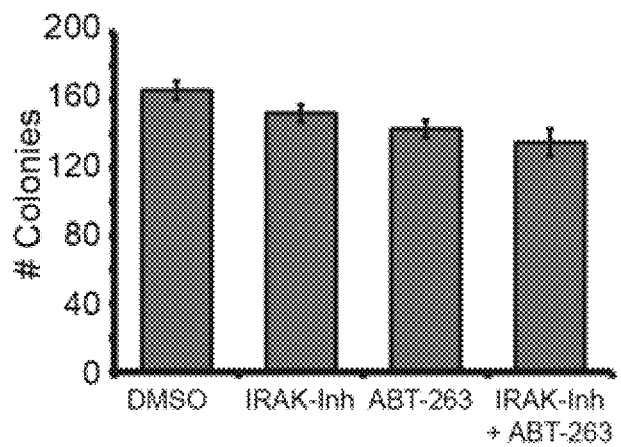
Figure 10D:
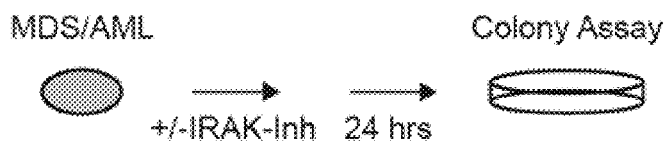
Figure 10E:
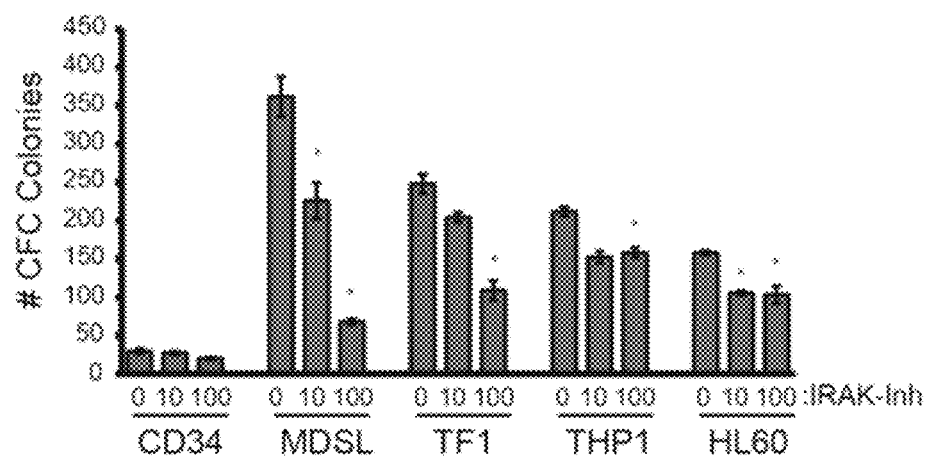
Figure 10F:
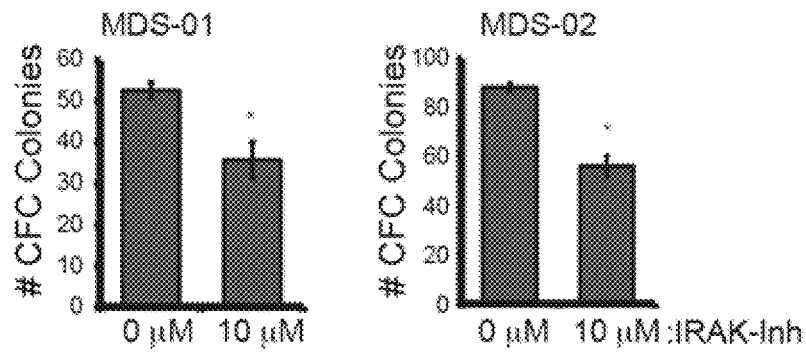
Figure 10G:
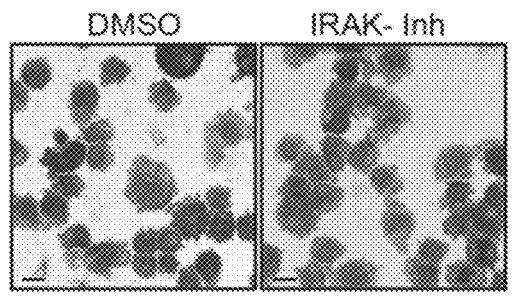
Figure 10H:
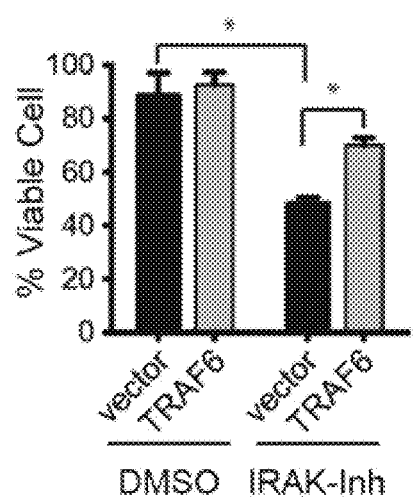
Figure 10I:
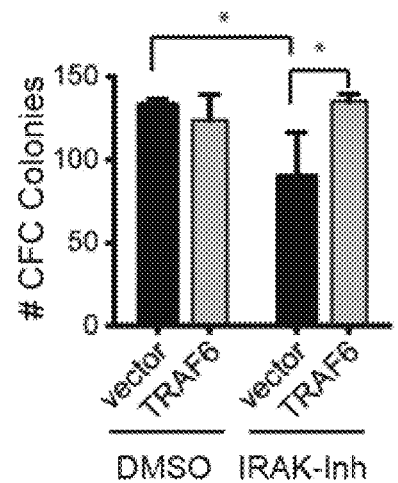
Figure 10J:
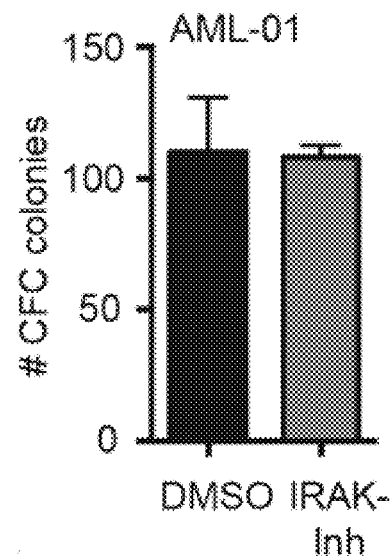
Figure 10K:
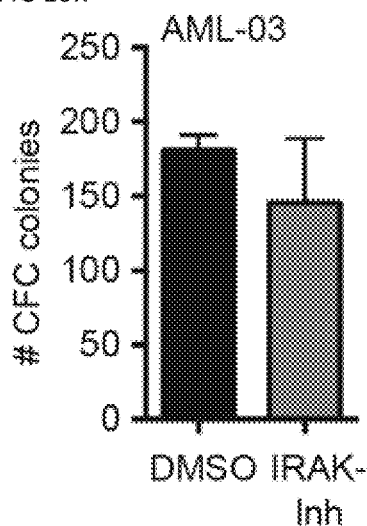
Figure 11A:
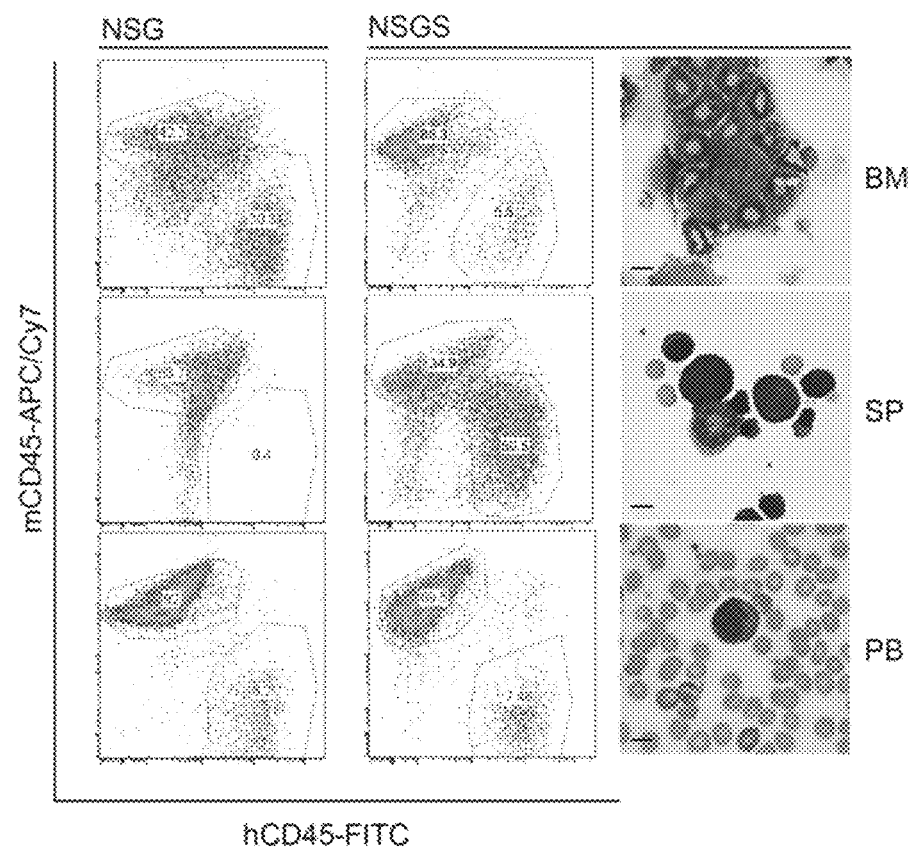
FIG. 11A-D. Characterization of MDSL xenograft model.
Figure 11B:
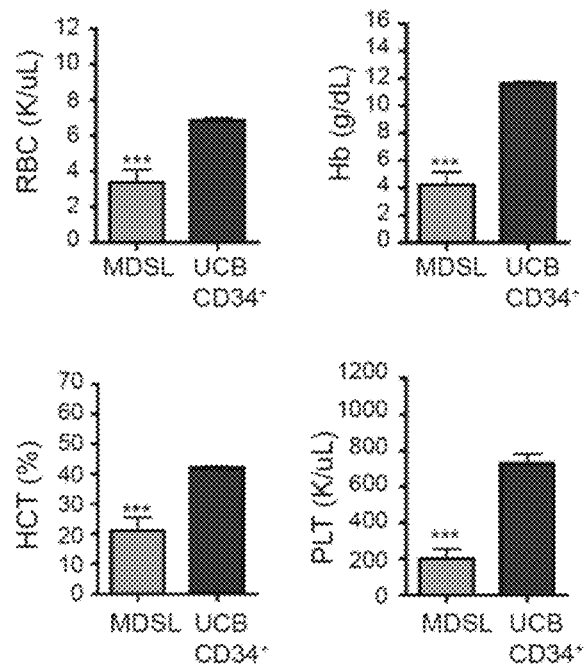
Figure 11C:
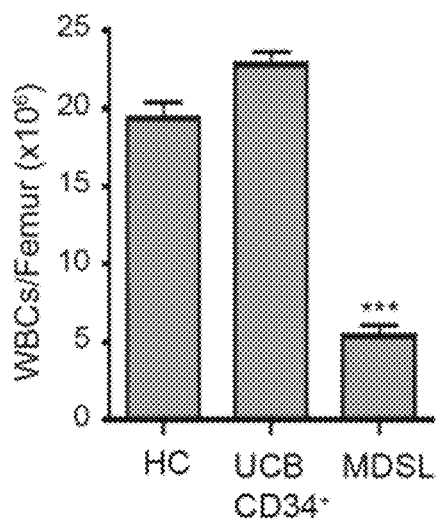
Figure 11D:
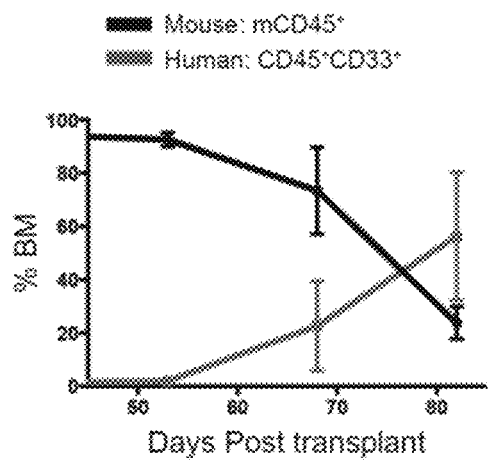
Figure 12A:
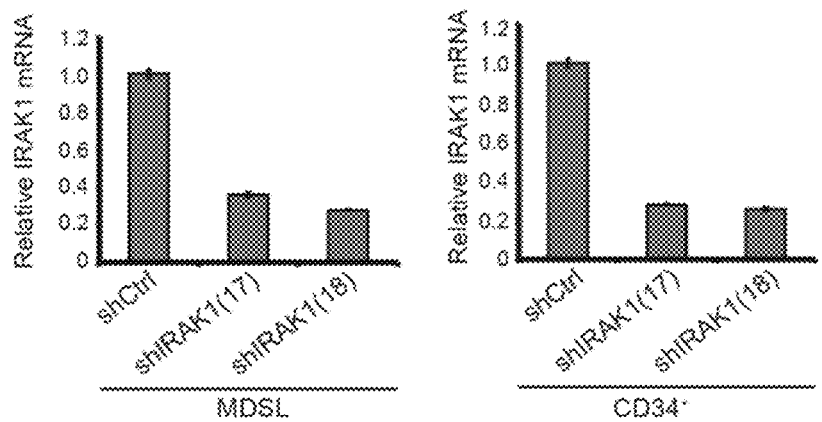
FIG. 12A-J. Lentiviral-mediated knockdown of IRAK1 mRNA and protein.
Figure 12B:
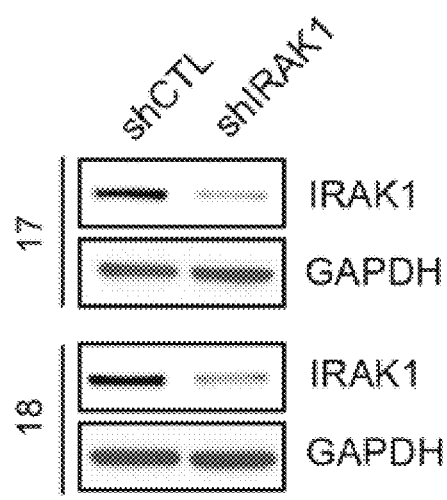
Figure 12C:
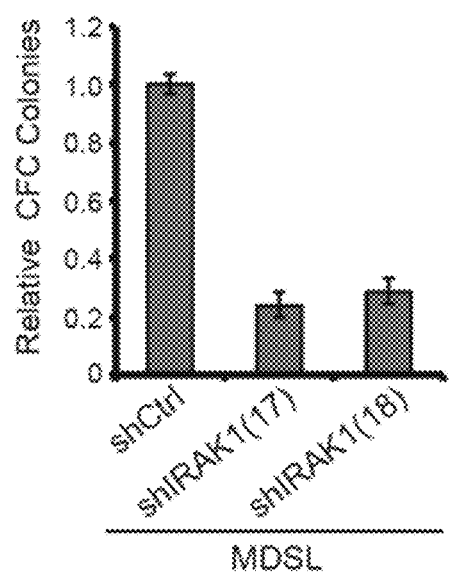
Figure 12D:
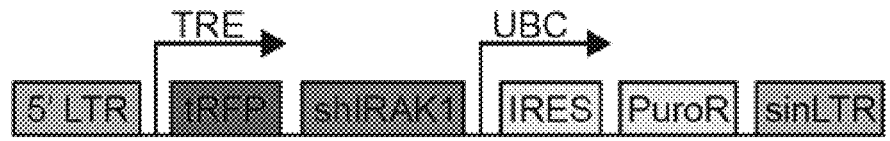
Figure 12E:
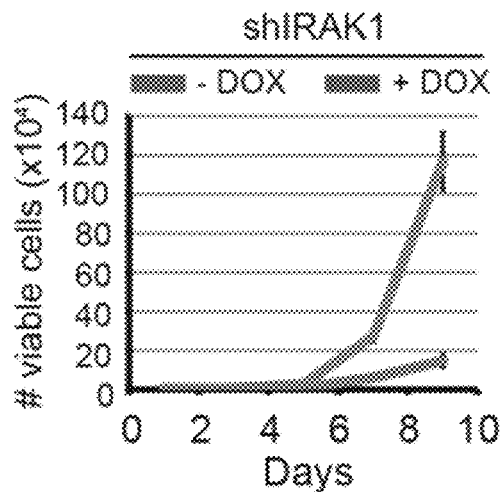
Figure 12F:
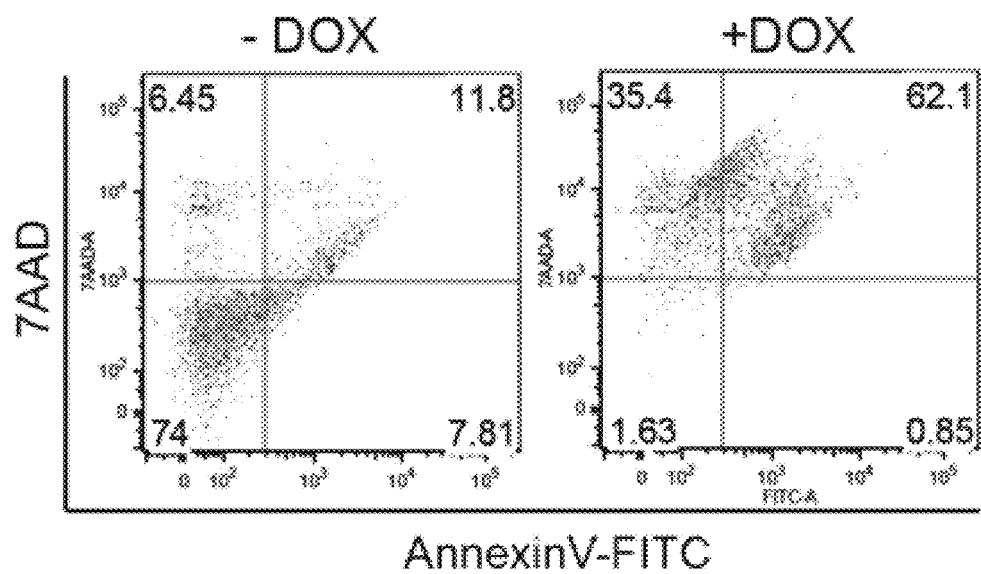
Figure 12G:
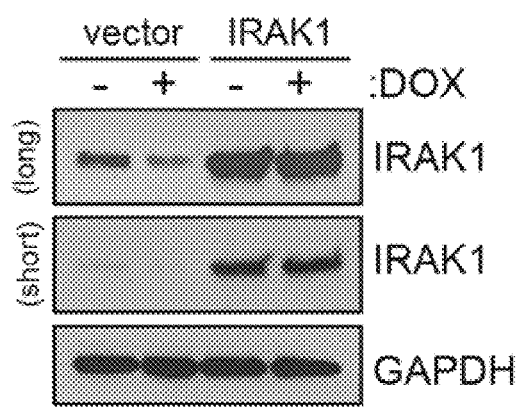
Figure 12H:
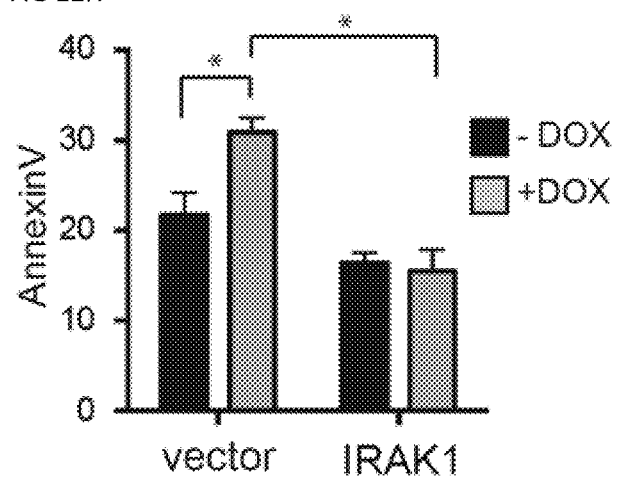
Figure 12I:
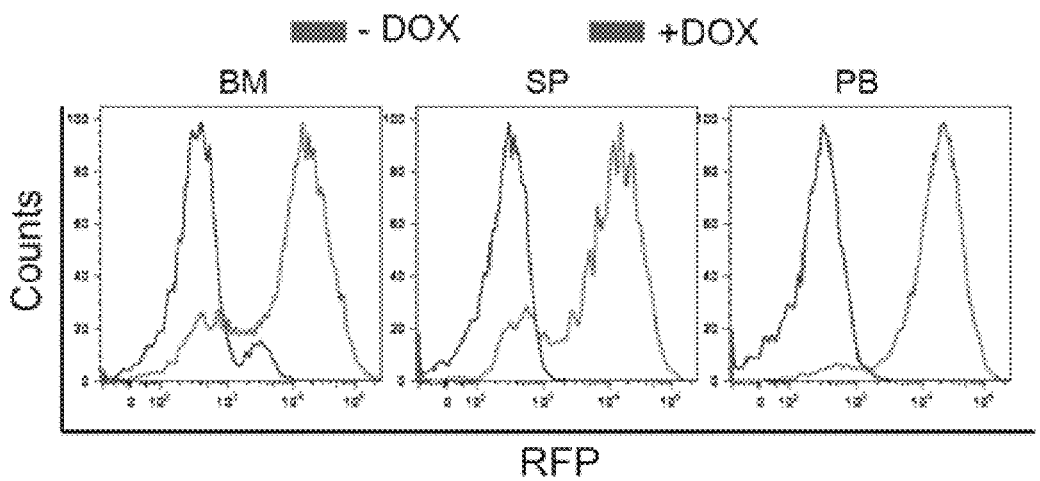
Figure 12J:
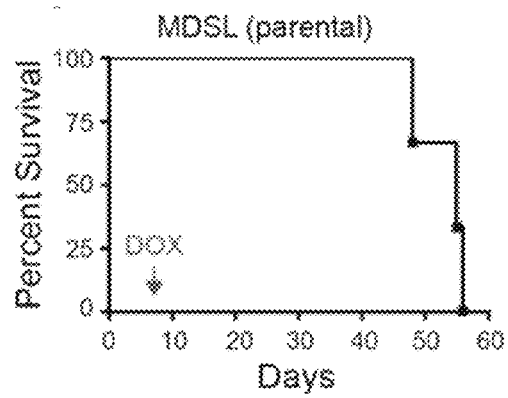
Figure 13A:
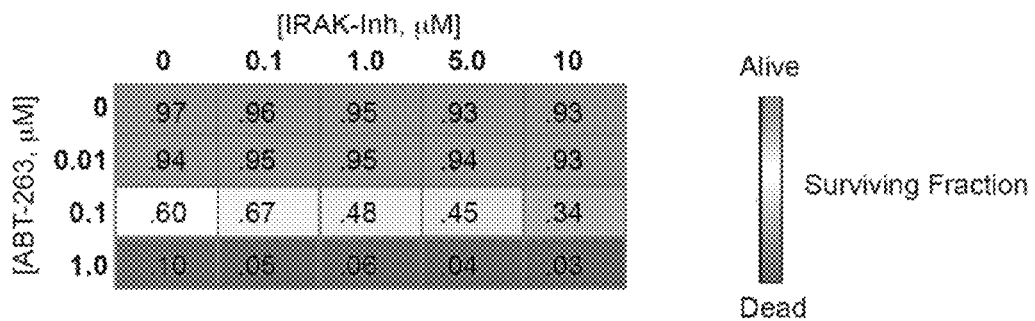
FIG. 13A-C. IRAK-Inh and ABT-263 collaborate to induce cytotoxicity.
Figure 13B:
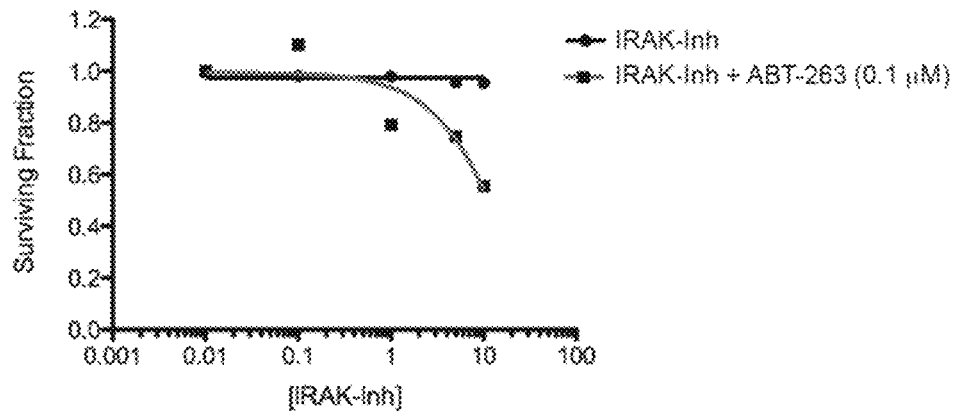
Figure 13C:
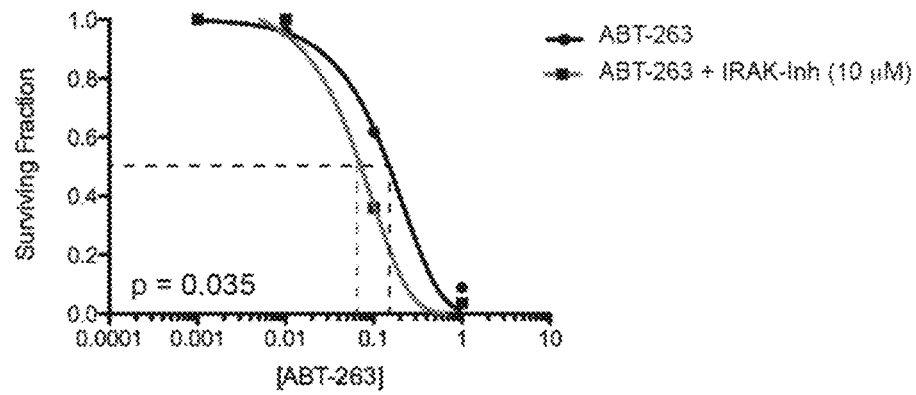

Moreover, we investigated whether combined IRAK1 and BCL2 inhibition could delay human MDS-like disease in vivo. MDSL cells were treated with IRAK-Inh (10 µM) and/or ABT-263 (0.1 µM) for 48 hrs in vitro and subsequently injected i.v. into NSGS mice (FIG. 4A). Treatment with IRAK-Inh or ABT-263 alone significantly delayed the MDS-like disease in NSG mice with a median survival of ~35 days (versus 28 days with DMSO treatment) (FIG. 7G). Mice receiving MDSL co-treated with IRAK-Inh and ABT-263 exhibited a significantly enhanced survival (43 days) as compared to individual drugs or DMSO (FIG. 7G). Not only was survival extended, but mice transplanted with cells pre-treated with the drug combination had improved red blood cell, hemoglobin, and platelet counts (not shown). In conclusion, inhibition of IRAK1 function with a small-molecular inhibitor may represent a treatment to inhibit MDS clone function and viability, while co-treatment with ABT-263 results in enhanced cytotoxicity.

Discussion

IRAK1 is a serine/threonine kinase that mediates signals from TLR/IL1R to NF-κB under normal conditions (Flannery and Bowie, 2011). Following receptor activation, MyD88 recruits IRAK4 and IRAK1, resulting in IRAK1 hyperphosphorylation. IRAK1 phosphorylation at Thr-209, which is mediated by upstream signals or through autophosphorylation, is a key post translational modification and a hallmark of its activation (Kollewe et al., 2004). Once phosphorylated, IRAK1 binds TRAF6 and undergoes K63-linked ubiquitination (Conze et al., 2008). This interaction between IRAK1 and TRAF6 initiates a signaling cascade resulting in NF-κβ nuclear translocation (Conze et al., 2008). Small molecule inhibitors targeting IRAK1 have been originally developed for autoimmune and inflammatory diseases (Durand-Reville et al., 2008; Wang et al., 2009). Given that the TRAF6/IRAK1 signaling complex remains in an activated state in MDS (Fang et al., 2012; Starczynowski and Karsan, 2010; Starczynowski et al., 2010), it is not surprising that inhibiting this complex may have a therapeutic benefit in MDS, and represent a viable approach to inhibit NF-κβ preferentially in malignant clones with activated IRAK1. Notably, most NF-κβ inhibitors to date have been disappointing for the treatment of myeloid malignancies due to toxicity (Breccia and Alimena, 2010).

Although IRAK1 mRNA is overexpressed in a subset of MDS patients, the level of expression rarely exceeds 2-fold. However, deletion and reduced expression of miR-146a is a common event in MDS as it resides within the deleted region on chr 5q and its expression is reduced in a large subset of normal karyotype MDS (Starczynowski et al., 2010; Starczynowski et al., 2011b). TRAF6 and IRAK1 are two targets of miR-146a, and germline knockout of miR-146a results in derepression of TRAF6 and IRAK1 protein (Boldin et al., 2011; Zhao et al., 2011). We confirmed a similar effect in MDS cells. This suggests that IRAK1 is transcriptionally and translationally upregulated in MDS patients making it a relevant molecular target. IRAK1 mRNA/protein is also overexpressed in subsets of AML patients (Camos et al., 2006), supporting our observations that targeting IRAK1 may extend to high-risk MDS and AML with active IRAK1.

Phosphorylation and activation of IRAK1 can also occur by gain-of-function mutations or aberrant expression of upstream signaling molecules. For example, human lymphomas with oncogenically active MyD88 mutations have constitutive IRAK1 phosphorylation and NF-κB activation, and are sensitive to IRAK inhibitors (Ngo et al., 2010). In Fanconi anemia, IRAK1 exists in a hyperphosphorylated (higher-molecular weight) state, potentially as a consequence of aberrant TLR8 signaling (Vanderwerf et al., 2009). Of note, mutations in MyD88 or TLR8 have not been reported in MDS or AML, suggesting that alternate molecular alterations activate IRAK1 in MDS/AML. However, mutations of TLR2 are reported in ~10% of MDS patients (Wei et al., 2012), and a recent finding identified overexpression of interleukin-1 receptor accessory protein (IL1RAP) in HSC from MDS and AML patients (Barreyro et al., 2012). Consistent with the hypothesis that hyperphosphorylation of IRAK1 in MDS may be due to aberrant activation downstream of the TLR/IL1R, a retrospective analysis revealed that chronic immune stimulation acts as a trigger and increases the risk for MDS and AML development (Kristinsson et al., 2011). Collectively, these observations suggest that, in addition to downregulation of miR-146a, multiple other molecular alterations can converge on and activate IRAK1 in MDS.

According to our integrative gene expression analysis, inhibition of IRAK1 revealed that IRAK1 regulates genes involved in survival, cell cycle/proliferation, chromatic assembly/DNA binding, RNA metabolism, cell migration/adhesion, and inflammation (FIG. 6C). These gene signatures are consistent with our observation that inhibiting IRAK1 in primary MDS marrow or cell lines results in delayed proliferation, reduced survival, and impaired progenitor function. IRAK-Inh was inefficient at downregulating pro-survival BCL2 genes, and in some cell lines, resulted in a compensatory increase in BCL2 expression, which is a common cellular response to cytostatic and cytotoxic therapies (Thomadaki and Scorilas, 2008). To overcome this compensatory effect, we combined a BCL2 inhibitor (ABT-263) with IRAK-Inh, which resulted in potent collaborative cytotoxic effects in MDS and AML cells by inducing rapid and profound apoptosis. Notably, this effect was observed even in MDS/AML cells that did not exhibit a compensatory increase in BCL2 expression in response to IRAK-Inh. That IRAK-Inh is effective at suppressing MDS cells, but not AML, can be explained by: (1) an increased apoptotic threshold in high-risk MDS and AML due to higher expression of prosurvival BCL2 family members, thus necessitating co-treatment with a BCL2 inhibitor; (2) the level of activated IRAK1 in AML is lower as compared to MDS, suggesting differences in the molecular circuitry of IRAK1 activation; and/or (3) only select subtypes of AML are sensitive to IRAK-Inh while a larger proportion of MDS are sensitive.

The complexity and heterogeneity of MDS, and the lack of human xenograft models remain as obstacles to identifying and evaluating novel molecular targets for this disease. In addition, primary MDS cells do not efficiently engraft into immunodeficient mice (Martin et al., 2011; Park et al., 2011). To overcome this limitation, we generated a human model using an MDS-derived patient cell line (MDSL). Consistent with phenotypic and cellular characteristics of MDS (Matsuoka et al., 2010; Tohyama et al., 1995), MDSL engraftment into NSG or NSGS immunodeficient mice results in a fatal and progressive anemia, thrombocytopenia, hypocellular marrow, and extramedullary hematopoiesis. Treatment of MDSL cells with IRAK-Inh or in vivo delivery of the inhibitor reduced the number of MDSL cells and delayed disease. This xenograft model represents an alternative to examine the mechanisms of low-risk MDS disease and a tool for preclinical studies using an MDS-derived patient cell line.

In summary, this work implicates IRAK1 as a drugable target for MDS. Inhibition with IRAK-Inh induces combined apoptosis and a cell cycle block, while inhibition with ABT-263 results in collaborative cytotoxicity in MDS cells. Inhibitors targeting IRAK1 reveal an avenue for suppressing altered TLR/IL1R/TRAF6/NF-κB pathway and eliminating the MDS clone.

REFERENCES

Bar, M., Stirewalt, D., Pogosova-Agadjanyan, E., Wagner, V., Gooley, T., Abbasi, N., Bhatia, R., Deeg, H. J., and Radich, J. (2008). Gene expression patterns in myelodyplasia underline the role of apoptosis and differentiation in disease initiation and progression. Translational oncogenomics 3, 137-149.

Barreyro, L., Will, B., Bartholdy, B., Zhou, L., Todorova, T. I., Stanley, R. F., Ben-Neriah, S., Montagna, C., Parekh, S., Pellagatti, A., et al. (2012). Overexpression of interleukin 1 receptor accessory protein in stem and progenitor cells and outcome correlation in AML and MDS. Blood.

Boldin, M. P., Taganov, K. D., Rao, D. S., Yang, L., Zhao, J. L., Kalwani, M., Garcia-Flores, Y., Luong, M., Devrekanli, A., Xu, J., et al. (2011). miR-146a is a significant brake on autoimmunity, myeloproliferation, and cancer in mice. J Exp Med 208, 1189-1201.

Breccia, M., and Alimena, G. (2010). NF-kappaB as a potential therapeutic target in myelodysplastic syndromes and acute myeloid leukemia. Expert opinion on therapeutic targets 14, 1157-1176.

Camos, M., Esteve, J., Jares, P., Colomer, D., Rozman, M., Villamor, N., Costa, D., Carrio, A., Nomdedeu, J., Montserrat, E., and Campo, E. (2006). Gene expression profiling of acute myeloid leukemia with translocation t(8;16)(p11;p13) and MYST3-CREBBP rearrangement reveals a distinctive signature with a specific pattern of HOX gene expression. Cancer Res 66, 6947-6954.

Chen, G., Zeng, W., Miyazato, A., Billings, E., Maciejewski, J. P., Kajigaya, S., Sloand, E. M., and Young, N. S. (2004). Distinctive gene expression profiles of CD34 cells from patients with myelodysplastic syndrome characterized by specific chromosomal abnormalities. Blood 104, 4210-4218.

Chen, J., Bardes, E. E., Aronow, B. J., and Jegga, A. G. (2009). ToppGene Suite for gene list enrichment analysis and candidate gene prioritization. Nucleic Acids Res 37, W305-311.

Conze, D. B., Wu, C. J., Thomas, J. A., Landstrom, A., and Ashwell, J. D. (2008). Lys63-linked polyubiquitination of IRAK-1 is required for interleukin-1 receptor- and toll-like receptor mediated NF-kappaB activation. Mol Cell Biol 28, 3538-3547.

Corey, S. J., Minden, M. D., Barber, D. L., Kantarjian, H., Wang, J. C., and Schimmer, A. D. (2007). Myelodysplastic syndromes: the complexity of stem-cell diseases. Nat Rev Cancer 7, 118-129.

Durand-Reville, T., Jewell, C., Hammond, C., and Chin, D. (2008). IRAK modulators for treating an inflammatory condition, cell proliferation disorder, immune disorder. In, (Biogen Idec).

Ebert, B. L. (2010). Preface. The biology and treatment of myelodysplastic syndrome. Hematology/oncology clinics of North America 24, xiii-xvi.

Fang, J., Rhyasen, G., Bolanos, L., Rasch, C., Varney, M., Wunderlich, M., Goyama, S., Jansen, G., Cloos, J., Rigolino, C., et al. (2012). Cytotoxic effects of bortezomib in myelodysplastic syndrome/acute myeloid leukemia depend on autophagy-mediated lysosomal degradation of TRAF6 and repression of PSMA1. Blood.

Flannery, S., and Bowie, A. G. (2011). The interleukin-1 receptor-associated kinases: critical regulators of innate immune signalling. Biochem Pharmacol 80, 1981-1991.

Gondek, L. P., Tiu, R., O'Keefe, C. L., Sekeres, M. A., Theil, K. S., and Maciejewski, J. P. (2008). Chromosomal lesions and uniparental disomy detected by SNP arrays in MDS, MDS/MPD, and MDS-derived AML. Blood 111, 1534-1542.

Greenberg, P., Cox, C., LeBeau, M. M., Fenaux, P., Morel, P., Sanz, G., Sanz, M., Vallespi, T., Hamblin, T., Oscier, D., et al. (1997). International scoring system for evaluating prognosis in myelodysplastic syndromes. Blood 89, 2079-2088.

Greenberg, P. L. (2010). Current therapeutic approaches for patients with myelodysplastic syndromes. Br J Haematol 150, 131-143.

Hofmann, W. K., de Vos, S., Komor, M., Hoelzer, D., Wachsman, W., and Koeffler, H. P. (2002). Characterization of gene expression of CD34+ cells from normal and myelodysplastic bone marrow. Blood 100, 3553-3560.

Kollewe, C., Mackensen, A. C., Neumann, D., Knop, J., Cao, P., Li, S., Wesche, H., and Martin, M. U. (2004). Sequential autophosphorylation steps in the interleukin-1 receptor-associated kinase-1 regulate its availability as an adapter in interleukin-1 signaling. J Biol Chem 279, 5227-5236.

Kristinsson, S. Y., Bjorkholm, M., Hultcrantz, M., Derolf, A. R., Landgren, O., and Goldin, L. R. (2011). Chronic immune stimulation might act as a trigger for the development of acute myeloid leukemia or myelodysplastic syndromes. J Clin Oncol 29, 2897-2903.

Martin, M. G., Welch, J. S., Uy, G. L., Fehniger, T. A., Kulkarni, S., Duncavage, E. J., and Walter, M. J. (2011). Limited engraftment of low-risk myelodysplastic syndrome cells in NOD/SCID gamma-C chain knockout mice. Leukemia 24, 1662-1664.

Matsuoka, A., Tochigi, A., Kishimoto, M., Nakahara, T., Kondo, T., Tsujioka, T., Tasaka, T., Tohyama, Y., and Tohyama, K. (2010). Lenalidomide induces cell death in an MDS-derived cell line with deletion of chromosome 5q by inhibition of cytokinesis. Leukemia 24, 748-755.

Ngo, V. N., Young, R. M., Schmitz, R., Jhavar, S., Xiao, W., Lim, K. H., Kohlhammer, H., Xu, W., Yang, Y., Zhao, H., et al. (2010). Oncogenically active MYD88 mutations in human lymphoma. Nature 470, 115-119.

Nimer, S. D. (2008). Myelodysplastic syndromes. Blood 111, 4841-4851.

O'Dwyer, M. E., Mauro, M. J., and Druker, B. J. (2003). STI571 as a targeted therapy for CML. Cancer Invest 21, 429-438.

Park, C., Pang, W., Price, E., Pluvinage, J., Schrier, S., and Weissman, I. (2011). Hematopoietic Stem Cells Are the Disease-Initiating Cells in the Myelodysplastic Syndromes. Paper presented at: ASH Annual Meeting (San Diego, Calif.).

Pellagatti, A., Cazzola, M., Giagounidis, A., Perry, J., Malcovati, L., Della Porta, M. G., Jadersten, M., Killick, S., Verma, A., Norbury, C. J., et al. (2010). Deregulated gene expression pathways in myelodysplastic syndrome hematopoietic stem cells. Leukemia 24, 756-764.

Powers, J. P., Li, S., Jaen, J. C., Liu, J., Walker, N. P., Wang, Z., and Wesche, H. (2006). Discovery and initial SAR of inhibitors of interleukin-1 receptor-associated kinase-4. Bioorg Med Chem Lett 16, 2842-2845.

Sekeres, M. A. (2010a). Are we nearer to curing patients with MDS? Best Pract Res Clin Haematol 23, 481-487.

Sekeres, M. A. (2010b). The epidemiology of myelodysplastic syndromes. Hematology/oncology clinics of North America 24, 287-294.

Sokol, L., Caceres, G., Volinia, S., Alder, H., Nuovo, G. J., Liu, C. G., McGraw, K., Clark, J. A., Sigua, C. A., Chen, D. T., et al. (2011). Identification of a risk dependent microRNA expression signature in myelodysplastic syndromes. Br J Haematol 153, 24-32.

Starczynowski, D. T., and Karsan, A. (2010). Innate immune signaling in the myelodysplastic syndromes. Hematol Oncol Clin North Am 24, 343-359.

Starczynowski, D. T., Kuchenbauer, F., Argiropoulos, B., Sung, S., Morin, R., Muranyi, A., Hirst, M., Hogge, D., Marra, M., Wells, R. A., et al. (2010). Identification of miR-145 and miR146a as mediators of the 5q-syndrome phenotype. Nat Med 16, 49-58.

Starczynowski, D. T., Kuchenbauer, F., Wegrzyn, J., Rouhi, A., Petriv, O., Hansen, C. L., Humphries, R. K., and Karsan, A. (2011a). MicroRNA-146a disrupts hematopoietic differentiation and survival. Exp Hematol 39, 167-178 e164.

Starczynowski, D. T., Morin, R., McPherson, A., Lam, J., Chari, R., Wegrzyn, J., Kuchenbauer, F., Hirst, M., Tohyama, K., Humphries, R. K., et al. (2011b). Genome-wide identification of human microRNAs located in leukemia-associated genomic alterations. Blood 117, 595-607.

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005). Gene set enrichment analysis: a knowledge-based approach for interpreting genome-wide expression profiles. Proc Natl Acad Sci USA 102, 15545-15550.

Taganov, K. D., Boldin, M. P., Chang, K. J., and Baltimore, D. (2006). NF-kappaB-dependent induction of microRNA miR-146, an inhibitor targeted to signaling proteins of innate immune responses. Proc Natl Acad Sci USA 103, 12481-12486.

Tehranchi, R., Woll, P. S., Anderson, K., Buza-Vidas, N., Mizukami, T., Mead, A. J., Astrand-Grundstrom, I., Strombeck, B., Horvat, A., Ferry, H., et al. (2010). Persistent malignant stem cells in del(5q) myelodysplasia in remission. N Engl J Med 363, 1025-1037.

Thomadaki, H., and Scorilas, A. (2008). Molecular profile of the BCL2 family of the apoptosis related genes in breast cancer cells after treatment with cytotoxic/cytostatic drugs. Connect Tissue Res 49, 261-264.

Tohyama, K., Tohyama, Y., Nakayama, T., Ueda, T., Nakamura, T., and Yoshida, Y. (1995). A novel factor-dependent human myelodysplastic cell line, MDS92, contains haemopoietic cells of several lineages. Br J Haematol 91, 795-799.

Vanderwerf, S. M., Svahn, J., Olson, S., Rathbun, R. K., Harrington, C., Yates, J., Keeble, W., Anderson, D. C., Anur, P., Pereira, N. F., et al. (2009). TLR8-dependent TNF-(alpha) overexpression in Fanconi anemia group C cells. Blood 114, 5290-5298.

Vasikova, A., Belickova, M., Budinska, E., and Cermak, J. (2010). A distinct expression of various gene subsets in CD34+ cells from patients with early and advanced myelodysplastic syndrome. Leuk Res 34, 1566-1572.

Wang, Z., Wesche, H., Stevens, T., Walker, N., and Yeh, W. C. (2009). IRAK-4 inhibitors for inflammation. Curr Top Med Chem 9, 724-737.

Wei, Y., Chen, R., Dimicoli, S., Bueso-Ramos, C. E., Neuberg, D. S., Pierce, S. A., Yang, H., Jia, Y., Zheng, H., Fang, Z., et al. (2012). Deregulation of TLR2-JMJD3 Innate Immunity Signaling, Including a Rare TLR2 SNP As a Potential Somatic Mutation, in Myelodysplastic Syndromes (MDS). In American Society of Hematology, (Atlanta, Ga.).

Wunderlich, M., Chou, F. S., Link, K. A., Mizukawa, B., Perry, R. L., Carroll, M., and Mulloy, J. C. (2010). AML xenograft efficiency is significantly improved in NOD/SCID-IL2RG mice constitutively expressing human SCF, GM-CSF and IL-3. Leukemia 24, 1785-1788.

Yang, Y. F., Chen, Z., Hu, S. L., Hu, J., Li, B., Li, J. T., Wei, L. J., Qian, Z. M., Lin, J. K., Feng, H., and Zhu, G. (2011). Interleukin-1 receptor associated kinases-1/4 inhibition protects against acute hypoxia/ischemia-induced neuronal injury in vivo and in vitro. Neuroscience 196, 25-34.

Zhao, J. L., Rao, D. S., Boldin, M. P., Taganov, K. D., O'Connell, R. M., and Baltimore, D. (2011). NF-kappaB dysregulation in microRNA-146a-deficient mice drives the development of myeloid malignancies. Proc Natl Acad Sci USA 108, 9184-9189.

Pellagatti, A., Cazzola, M., Giagounidis, A. A., Malcovati, L., Porta, M. G., Killick, S., Campbell, L. J., Wang, L., Langford, C. F., Fidler, C., et al. (2006). Gene expression profiles of CD34+ cells in myelodysplastic syndromes: involvement of interferon-stimulated genes and correlation to FAB subtype and karyotype. Blood 108, 337-345.

Starczynowski, D. T., Lockwood, W. W., Delehouzee, S., Chari, R., Wegrzyn, J., Fuller, M., Tsao, M. S., Lam, S., Gazdar, A. F., Lam, W. L., and Karsan, A. (2011). TRAF6 is an amplified oncogene bridging the RAS and NF-kappaB pathways in human lung cancer. J Clin Invest 121, 4095-4105. Tse, C., Shoemaker, A. R., Adickes, J., Anderson, M. G., Chen, J., Jin, S., Johnson, E. F., Marsh, K. C., Mitten, M. J., Nimmer, P., et al. (2008). ABT-263: a potent and orally bioavailable Bcl-2 family inhibitor. Cancer Res 68, 3421-3428.

Valk, P. J., Verhaak, R. G., Beijen, M. A., Erpelinck, C. A., Barjesteh van Waalwijk van Doorn-Khosrovani, S., Boer, J. M., Beverloo, H. B., Moorhouse, M. J., van der Spek, P. J., Lowenberg, B., and Delwel, R. (2004). Prognostically useful gene-expression profiles in acute myeloid leukemia. N Engl J Med 350, 1617-1628.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method of treating acute myeloid leukemia in an individual comprising the step of administering to said individual a composition comprising an IRAK1/4 inhibitor.

2. The method of claim 1 wherein said IRAK1/4 inhibitor is selected from N-acyl-2-aminobenzimidazoles, imidazo[1,2-a]pyridino-pyrimidine, imidazo[1,2-a]pyridino-pyridine, benzimidazolo-pyridine, N-(2-morpholinylethyl)-2-(3-nitrobenzoylamido)-benzimidazole,

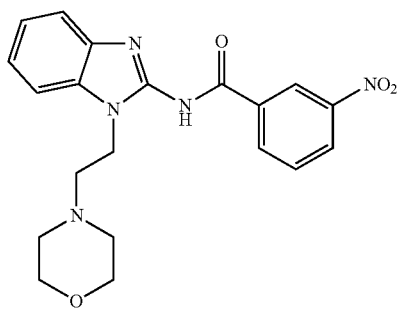 [SMILES: O=C(Nc1nc2ccccc2n1CCN1CCOCC1)c1cccc([N+](=O)[O-])c1]

(IRAK1/4), or combinations thereof.

3. The method of claim 1 wherein said IRAK1/4 inhibitor comprises an RNAi sufficient to inhibit IRAK1 expression.

4. The method of claim 1, further comprising the step of administering to said individual an apoptotic modulator.

5. The method of claim 1, further comprising the step of administering to said individual an apoptotic modulator, wherein said apoptotic modulator comprises a BCL2 inhibitor.

6. The method of claim 1, comprising the step of administering to said individual an apoptotic modulator, wherein said apoptotic modulator comprises a BCL2 inhibitor selected from

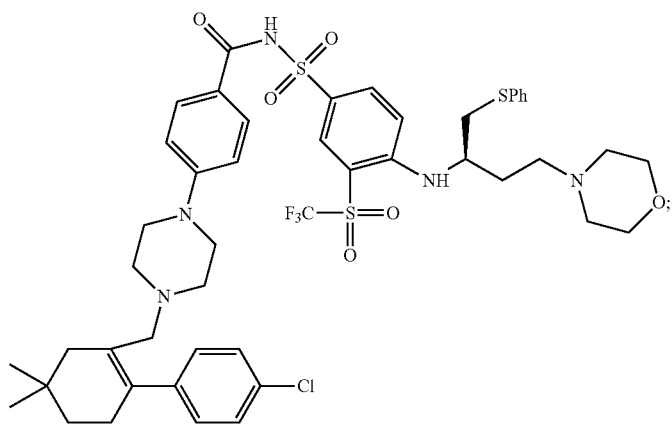

(ABT-263, Navitoclax)

-continued

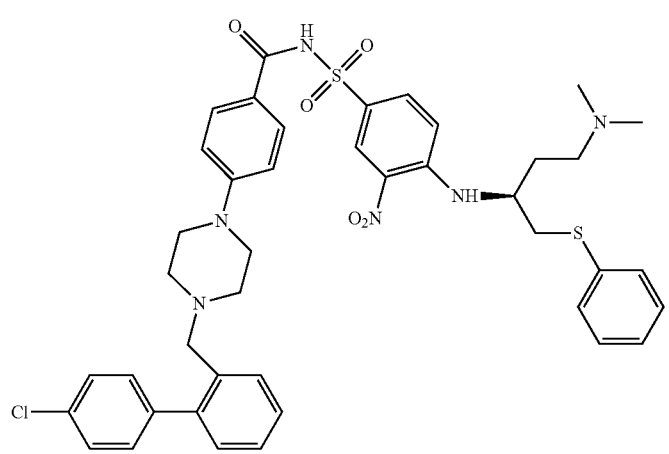

(ABT-737)

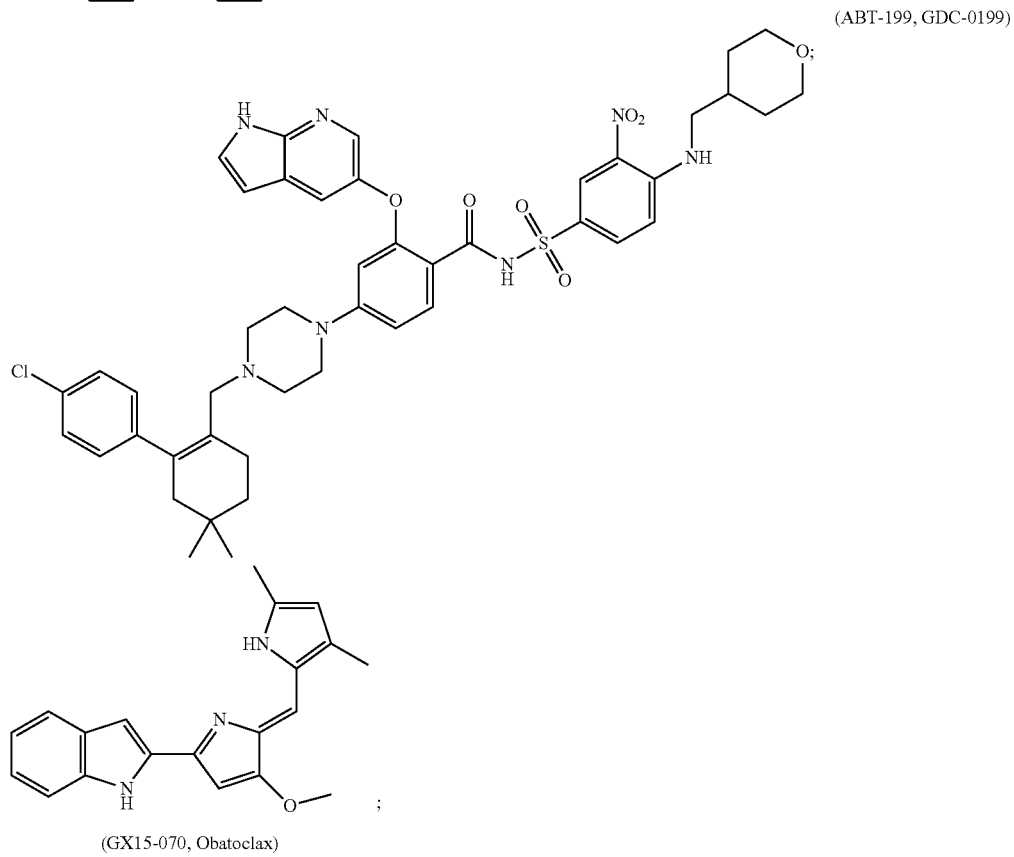

(ABT-199, GDC-0199)

;

(GX15-070, Obatoclax)

and
combinations thereof.

7. The method of claim 1 wherein said administering step is selected from orally, rectally, nasally, topically, parenterally, subcutaneously, intramuscularly, intravenously, transdermally, or a combination thereof.

8. The method of claim 1 wherein said administration decreases the incidence of marrow failure, immune dysfunction, transformation to overt leukemia, or combinations thereof in said individual, as compared to an individual not receiving said composition.

9. The method of claim 1 wherein said method decreases a marker of viability of MDS cells.

10. The method of claim 1, wherein said treatment decreases a marker of viability of MDS and/or AML cells, wherein marker is selected from survival over time, proliferation, growth, migration, formation of colonies, chromatic assembly, DNA binding, RNA metabolism, cell migration, cell adhesion, inflammation, or a combination thereof.

* * * * *

UNITED STATES PATENT AND TRADEMARK OFFICE
CERTIFICATE OF CORRECTION

PATENT NO. : 9,855,273 B2
APPLICATION NO. : 15/288402
DATED : January 2, 2018
INVENTOR(S) : Daniel Starczynowski and Garrett W. Rhyasen It is certified that error appears in the above-identified patent and that said Letters Patent is hereby corrected as shown below:

In the Claims

Column 34, Lines 36-67 - Column 35, Lines 1-55, Claim 6:

After the first structure, reads "(ABT-263, Navitoclax)" which should be deleted and replaced with "(ABT-263, Navitoclax);".

To the right of the second structure, reads "(ABT-737)" which should be deleted and replaced with "(ABT-737);".

Between the second and third structure, delete the floating ";".

To the right of the third structure, reads "(ABT-199, GDC-0199)" which should be deleted and replaced with "(ABT-199, GDC-0199);".

Delete the ";" after "O" in the upper right portion of the fourth structure.

In the lower, right-hand portion of the fourth structure, delete the floating ";".

Below the fourth structure, reads "(GX15-070, Obatoclax)" which should be deleted and replaced with "(GX15-070, Obatoclax);".

Signed and Sealed this
Tenth Day of April, 2018

Andrei Iancu
*Director of the United States Patent and Trademark Office*